United States Patent
Brotherton-Pleiss et al.

(10) Patent No.: US 9,353,096 B2
(45) Date of Patent: May 31, 2016

(54) SUBSTITUTED PHENYLCARBAMATE COMPOUNDS

(71) Applicant: Hoffmann-La Roche Inc., Little Falls, NJ (US)

(72) Inventors: Christine E. Brotherton-Pleiss, Sunnyvale, CA (US); Zhi Chen, Livingston, NJ (US); Shawn David Erickson, Leonia, NJ (US); Kyungjin Kim, Livingston, NJ (US); Hongju Li, Edison, NJ (US); Yimin Qian, Wayne, NJ (US); Sung-Sau So, Verona, NJ (US); Peter Michael Wovkulich, Apalachin, NY (US); Lin Yi, Basking Ridge, NJ (US)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/683,452

(22) Filed: Apr. 10, 2015

(65) Prior Publication Data

US 2015/0218144 A1    Aug. 6, 2015

Related U.S. Application Data

(63) Continuation of application No. PCT/EP2013/070999, filed on Oct. 9, 2013.

(60) Provisional application No. 61/712,836, filed on Oct. 12, 2012.

(51) Int. Cl.

| | |
|---|---|
| *C07D 241/04* | (2006.01) |
| *C07D 265/30* | (2006.01) |
| *C07D 279/12* | (2006.01) |
| *C07D 413/04* | (2006.01) |
| *C07D 413/06* | (2006.01) |
| *C07D 413/12* | (2006.01) |

(52) U.S. Cl.
CPC ............ *C07D 413/12* (2013.01); *C07D 241/04* (2013.01); *C07D 265/30* (2013.01); *C07D 279/12* (2013.01); *C07D 413/04* (2013.01); *C07D 413/06* (2013.01)

(58) Field of Classification Search
CPC .. C07D 241/04; C07D 265/30; C07D 279/12; C07D 413/04; C07D 413/06; C07D 413/12
See application file for complete search history.

(56) References Cited

U.S. PATENT DOCUMENTS

2009/0105259 A1    4/2009    Jeong et al.

FOREIGN PATENT DOCUMENTS

| EP | 0903349 A2 | 3/1999 | |
|---|---|---|---|
| WO | 01/98269 A2 | 12/2001 | |
| WO | 2005/121100 A1 | 12/2005 | |
| WO | 2008/124849 A2 | 10/2008 | |
| WO | 2011/132017 A1 | 10/2011 | |
| WO | WO 2011/132017 | * 10/2011 | ........... C07D 471/04 |

OTHER PUBLICATIONS

Database CA [Online] Chemical Abstracts Service, Columbus, Ohio, US; Akhmedov, SH. T. et al., "Synthesis and study of some morpholinoand chloroprolyl carbamates", XP002717687, retrieved from STN Database accession No. 1982:85483; & Akhmedov, SH. T. et al., "Synthesis and study of some morpholino- and chloropropyl carbamates", Izvestiya Vysshikh Uchebnykh Zavedenii, Khimiya I Khimicheskaya Tekhnologiya, 24(11), 1446-7 Coden: Ivukar; ISSN: 0579-2991, 1981, in 11 pages.
International Preliminary Report on Patentability issued in International Application No. PCT/EP2013/070999, dated Apr. 14, 2015, in 7 pages.
International Preliminary Report on Patentability issued in International Application No. PCT/EP2013/071402, dated Apr. 21, 2015, in 6 pages.
International Preliminary Report on Patentability issued in International Application No. PCT/EP2013/073129, dated May 12, 2015, in 6 pages.
International Search Report issued in International Application No. PCT/EP2013/070999, dated Jan. 1, 2014, in 4 pages.
International Search Report issued in International Application No. PCT/EP213/0701402, dated Nov. 22, 2013, in 4 pages.
International Search Report issued in International Application No. PCT/EP213/073129, dated Dec. 11, 2013, in 3 pages.

(Continued)

*Primary Examiner* — Erich A Leeser
(74) *Attorney, Agent, or Firm* — Lily J. Ackerman

(57) ABSTRACT

The invention is concerned with the compounds of formula (I):

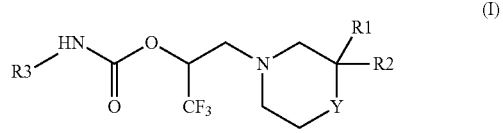

and pharmaceutically acceptable salts thereof, wherein Y, R1, R2 and R3 are defined in the detailed description and claims. In addition, the present invention relates to methods of manufacturing and using the compounds of formula (I) as well as pharmaceutical compositions containing such compounds. The compounds of formula (I) are antagonists of the TRPA1 channel and may be useful in treating inflammatory diseases and disorders associated with that channel.

17 Claims, No Drawings

(56) References Cited

OTHER PUBLICATIONS

Preti et al., "TRP channels as therapeutic targets in airway disorders: a patent review" Expert Opin. Ther. Patents 22(6):663-695 ( 2012).

Wang et al., "Synthesis and evaluation of 3-aryl piperidine analogs as potent and efficacious dopamine D4 receptor agonists" Bioorg. Med. Chem. 13:4667-4678 ( 2005).

* cited by examiner

SUBSTITUTED PHENYLCARBAMATE COMPOUNDS

CROSS REFERENCE TO RELATED APPLICATIONS

This application is a continuation of International Application No. PCT/EP2013/070999 having an international filing date of Oct. 9, 2013, the entire contents of which are incorporated herein by reference, and which claims benefit under 35 U.S.C. §119 to U.S. Provisional Patent Application No. 61/712,836 filed Oct. 12, 2012, the entire contents of which are incorporated herein by reference.

FIELD OF THE INVENTION

The present invention relates to organic compounds useful for therapy and/or prophylaxis in a mammal of an inflammatory disease or disorder, and in particular to substituted phenylcarbamate compounds, their manufacture, pharmaceutical compositions containing them and their use as Transient Receptor Potential (TRP) channel antagonists.

All documents cited to or relied upon below are expressly incorporated herein by reference.

BACKGROUND OF THE INVENTION

TRP channels are a class of ion channels found on the plasma membrane of a variety of human (and other animal) cell types. There are at least 28 known human TRP channels which are broken into a number of families or groups based upon sequence homology and function. TRPA1 is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a 'chemosensor'. Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress, e.g. 4-hydroxynonenal and related compounds, activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation.

SUMMARY OF THE INVENTION

The invention provides for a compound of formula (I):

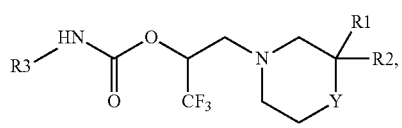

(I)

wherein:
Y is —O—, —NH—, —SO$_2$—, —N(CH$_3$)— or —N(C(O)CH$_3$)—;
R1 is hydrogen;
R2 is hydrogen or —X-A;
X is —CH$_2$— or a single bond;
A is unsubstituted phenyl,
  phenyl mono- or bi-substituted independently with halogen, CF$_3$, alkoxy or lower alkyl,
  unsubstituted heteroaryl, or
  heteroaryl mono-substituted with CF$_3$, lower alkyl or alkoxy; and
R3 is unsubstituted phenyl,
  phenyl mono- or bi-substituted independently with halogen or lower alkyl,
  unsubstituted pyridinyl, or
  pyridinyl mono-substituted with halogen,
or a pharmaceutically acceptable salt thereof.

The invention also provides for pharmaceutical compositions comprising the compounds, methods of using the compounds and methods of preparing the compounds.

All documents cited to or relied upon below are expressly incorporated herein by reference.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables R1 to R6 of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

The term "alkoxy" denotes a group of the formula —O—R', wherein R' is an alkyl group. Examples of alkoxy moieties include methoxy, ethoxy, isopropoxy, and tert-butoxy.

"Aryl" means a monovalent cyclic aromatic hydrocarbon moiety having a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "halo", "halogen" and "halide", which may be used interchangeably, refer to a substituent fluoro, chloro, bromo, or iodo.

"Cycloalkyl" means a monovalent saturated carbocyclic moiety having mono- or bicyclic rings. The cycloalkyl moiety can optionally be substituted with one or more substituents. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

Unless otherwise indicated, the term "hydrogen" or "hydro" refers to the moiety of a hydrogen atom (—H) and not $H_2$.

In the present description and claims, the representation of hydrogen may be omitted according to the IUPAC convention in the representation of chemical structures. The person skilled in the art therefore understands that when the valence of an atom is not fully represented (e.g. a carbon or nitrogen atom) on a chemical structure, said atom is in fact substituted with one or more hydrogen atoms. For example, "—N—" means "—NH—".

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers" and fall within the scope of the invention. Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention provides for compounds of formula (I):

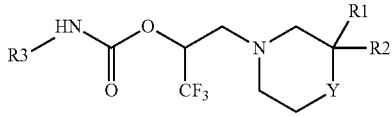

wherein:
Y is —O—, —NH—, —SO₂—, —N(CH₃)— or —N(C(O) CH₃)—;
R1 is hydrogen;
R2 is hydrogen or —X-A;
X is —CH₂— or a single bond;
A is unsubstituted phenyl,
    phenyl mono- or bi-substituted independently with halogen, CF₃, alkoxy or lower alkyl,
    unsubstituted heteroaryl, or
    heteroaryl mono-substituted with CF₃, lower alkyl or alkoxy; and R3 is unsubstituted phenyl,
    phenyl mono- or bi-substituted independently with halogen, or lower alkyl
    unsubstituted pyridinyl, or
    pyridinyl mono-substituted with halogen,
or a pharmaceutically acceptable salt thereof.

In another embodiment of the invention, provided are compounds according to formula (I) wherein Y is —O—.

In another embodiment of the invention, provided are compounds according to formula (I) wherein Y is —NH—, —N(CH₃)— or —N(C(O)CH₃)—.

In another embodiment of the invention, provided are compounds according to formula (I) wherein Y is —SO₂—.

In another embodiment of the invention, provided are compounds according to formula (I) wherein R1 is hydrogen.

In another embodiment of the invention, provided are compounds according to formula (I) wherein R2 is hydrogen.

In another embodiment of the invention, provided are compounds according to formula (I) wherein R2 is —X-A.

In another embodiment of the invention, provided are compounds according to formula (I) wherein X is a single bond.

In another embodiment of the invention, provided are compounds according to formula (I) wherein A is unsubstituted phenyl or phenyl mono- or bi-substituted independently with halogen, CF₃, alkoxy or lower alkyl.

In another embodiment of the invention, provided are compounds according to formula (I) wherein A is unsubstituted heteroaryl or heteroaryl mono-substituted with CF₃, lower alkyl or alkoxy.

In another embodiment of the invention, provided are compounds according to formula (I) wherein said heteroaryl is unsubstituted pyridinyl, unsubstituted pyrimidinyl or unsubstituted thiophene.

In another embodiment of the invention, provided are compounds according to formula (I) wherein said heteroaryl is mono-substituted pyridinyl, mono-substituted pyrimidinyl or monosubstituted thiophene, wherein said mono-substituent is CF₃, lower alkyl or alkoxy.

In another embodiment of the invention, provided are compounds according to formula (I) wherein R3 is unsubstituted phenyl or phenyl mono- or bi-substituted independently with halogen or lower alkyl.

In another embodiment of the invention, provided are compounds according to formula (I) wherein R3 is unsubstituted pyridinyl or pyridinyl mono-substituted with halogen.

In another embodiment of the invention, provided are compounds according to formula (I) wherein the compound is:
(4-Chlorophenyl)-carbamic acid (S)-2,2,2-trifluoro-1-[(R)-2-(4-fluoro-3-trifluoromethylphenyl)-morpholin-4-ylmethyl]-ethyl ester hydrochloride;
(4-Chlorophenyl)-carbamic acid (S)-2,2,2-trifluoro-1-[2-(4-fluoro-3-trifluoromethylphenyl)-morpholin-4-ylmethyl]-ethyl ester hydrochloride;
(4-Chloro-3-fluorophenyl)-carbamic acid (S)-2,2,2-trifluoro-1-[(R)-2-(4-fluoro-3-trifluoromethylphenyl)-morpholin-4-ylmethyl]-ethyl ester hydrochloride;
(4-Chloro-3-fluorophenyl)-carbamic acid (S)-1-[(R)-2-(4-chloro-3-fluorophenyl)-morpholin-4-ylmethyl]-2,2,2-trifluoroethyl ester hydrochloride;
(4-Chloro-3-fluorophenyl)-carbamic acid (S)-1-[(R)-2-(3-chloro-4-fluorophenyl)-morpholin-4-ylmethyl]-2,2,2-trifluoroethyl ester hydrochloride;
(4-Chloro-3-fluorophenyl)-carbamic acid (S)-1-[(R)-2-(3-chlorophenyl)-morpholin-4-ylmethyl]-2,2,2-trifluoroethyl ester hydrochloride;

(4-Chloro-3-fluorophenyl)-carbamic acid (S)-1-[(S)-2-(3-chlorophenyl)-morpholin-4-ylmethyl]-2,2,2-trifluoroethyl ester hydrochloride;

(4-Chlorophenyl)-carbamic acid (S)-1-((R)-2-benzyl-morpholin-4-ylmethyl)-2,2,2-trifluoroethyl ester hydrochloride;

(4-Chlorophenyl)-carbamic acid (S)-1-((S)-2-benzyl-morpholin-4-ylmethyl)-2,2,2-trifluoroethyl ester hydrochloride;

(4-Chlorophenyl)-carbamic acid (S)-2,2,2-trifluoro-1-[(R)-2-(3-trifluoromethylphenyl)-morpholin-4-ylmethyl]-ethyl ester hydrochloride;

(4-Chlorophenyl)-carbamic acid (S)-2,2,2-trifluoro-1-[(S)-2-(3-trifluoromethylphenyl)-morpholin-4-ylmethyl]-ethyl ester hydrochloride;

(4-Chloro-3-fluorophenyl)-carbamic acid (S)-2,2,2-trifluoro-1-[(R)-2-(3-trifluoromethylphenyl)-morpholin-4-ylmethyl]-ethyl ester hydrochloride;

(4-Chlorophenyl)-carbamic acid (S)-2,2,2-trifluoro-1-[(R)-2-(3-methoxyphenyl)-morpholin-4-ylmethyl]-ethyl ester;

(4-Chlorophenyl)-carbamic acid (S)-2,2,2-trifluoro-1-[(S)-2-(3-methoxyphenyl)-morpholin-4-ylmethyl]-ethyl ester;

(4-Chlorophenyl)-carbamic acid (S)-2,2,2-trifluoro-1-[(R)-2-(3-methoxyphenyl)-1,1-dioxo-1$\lambda^6$-thiomorpholin-4-ylmethyl]-ethyl ester;

(4-Chlorophenyl)-carbamic acid (S)-2,2,2-trifluoro-1-[2-(3-methoxyphenyl)-1,1-dioxo-1$\lambda^6$-thiomorpholin-4-ylmethyl]-ethyl ester;

(4-Chlorophenyl)-carbamic acid (S)-1-[(R)-1,1-dioxo-2-(3-trifluoromethylphenyl)-1$\lambda^6$-thiomorpholin-4-ylmethyl]-2,2,2-trifluoroethyl ester;

(4-Chlorophenyl)-carbamic acid (S)-1-[(S)-1,1-dioxo-2-(3-trifluoromethylphenyl)-1$\lambda^6$-thiomorpholin-4-ylmethyl]-2,2,2-trifluoroethyl ester;

(4-Chloro-3-fluorophenyl)-carbamic acid (S)-1-[(R)-1,1-dioxo-2-(3-trifluoromethylphenyl)-1$\lambda^6$-thiomorpholin-4-ylmethyl]-2,2,2-trifluoroethyl ester;

(4-Chloro-3-fluorophenyl)-carbamic acid (S)-1-[(S)-1,1-dioxo-2-(3-trifluoromethylphenyl)-1$\lambda^6$-thiomorpholin-4-ylmethyl]-2,2,2-trifluoroethyl ester;

(4-Chloro-3-fluorophenyl)-carbamic acid (S)-2,2,2-trifluoro-1-[(R)-2-(6-trifluoromethylpyridin-3-yl)-morpholin-4-ylmethyl]-ethyl ester;

(4-Chloro-3-fluorophenyl)-carbamic acid (S)-2,2,2-trifluoro-1-[(S)-2-(6-trifluoromethylpyridin-3-yl)-morpholin-4-ylmethyl]-ethyl ester hydrochloride;

(4-Chloro-3-fluorophenyl)-carbamic acid (S)-2,2,2-trifluoro-1-[(S)-2-(2-trifluoromethylpyrimidin-4-yl)-morpholin-4-ylmethyl]-ethyl ester hydrochloride;

(4-Chloro-3-fluorophenyl)-carbamic acid (S)-2,2,2-trifluoro-1-[(S)-2-(2-isopropylpyrimidin-4-yl)-morpholin-4-ylmethyl]-ethyl ester hydrochloride;

(4-Chloro-3-fluorophenyl)-carbamic acid (S)-2,2,2-trifluoro-1-[(R)-2-(2-isopropylpyrimidin-4-yl)-morpholin-4-ylmethyl]-ethyl ester hydrochloride;

(4-Chlorophenyl)-carbamic acid (S)-2,2,2-trifluoro-1-(4-methyl-3-phenylpiperazin-1-ylmethyl)-ethyl ester hydrochloride;

(4-Chlorophenyl)-carbamic acid (S)-1-(4-acetyl-3-phenylpiperazin-1-ylmethyl)-2,2,2-trifluoroethyl ester hydrochloride;

(4-Chlorophenyl)-carbamic acid (S)-2,2,2-trifluoro-1-[(R)-2-(4-trifluoromethylphenyl)-morpholin-4-ylmethyl]-ethyl ester hydrochloride;

(4-Chlorophenyl)-carbamic acid (S)-2,2,2-trifluoro-1-[(S)-2-(4-trifluoromethylphenyl)-morpholin-4-ylmethyl]-ethyl ester hydrochloride;

(4-Chloro-3-fluorophenyl)carbamic acid (S)-2,2,2-trifluoro-1-[(R)-2-(4-trifluoromethylphenyl)-morpholin-4-ylmethyl]-ethyl ester hydrochloride;

(4-Chloro-3-fluorophenyl)-carbamic acid (S)-2,2,2-trifluoro-1-[(S)-2-(4-trifluoromethylphenyl)-morpholin-4-ylmethyl]-ethyl ester hydrochloride;

(3-Chloro-4-methylphenyl)-carbamic acid (S)-2,2,2-trifluoro-1-[2-(4-trifluoromethylphenyl)-morpholin-4-ylmethyl]-ethyl ester hydrochloride;

(4-Chloro-3-fluorophenyl)-carbamic acid (S)-1-[(R)-2-(3,4-difluorophenyl)-morpholin-4-ylmethyl]-2,2,2-trifluoroethyl ester hydrochloride;

(4-Chloro-3-fluorophenyl)-carbamic acid (S)-1-[(S)-2-(3,4-difluorophenyl)-morpholin-4-ylmethyl]-2,2,2-trifluoroethyl ester hydrochloride;

(4-Chloro-3-fluorophenyl)carbamic acid (S)-1-[(R)-2-(4-fluorophenyl)-morpholin-4-ylmethyl]-2,2,2-trifluoroethyl ester hydrochloride;

p-Tolylcarbamic acid (S)-1-[2-(3,4-difluorophenyl)-morpholin-4-ylmethyl]-2,2,2-trifluoroethyl ester hydrochloride;

(6-Chloropyridin-3-yl)carbamic acid (S)-2,2,2-trifluoro-1-[2-3-trifluoromethylphenyl]-morpholin-4-ylmethyl]-ethyl ester hydrochloride;

(S)—N-(4-chloro-3-fluorophenyl)-4,4,4-trifluoro-3-[(R)-2-(3-trifluoromethylphenyl)-morpholin-4-ylmethyl]-butyramide;

(S)—N-(4-chloro-3-fluorophenyl)-4,4,4-trifluoro-3-[(S)-2-(3-trifluoromethylphenyl)-morpholin-4-ylmethyl]-butyramide;

(4-Chlorophenyl)-carbamic acid 2,2,2-trifluoro-1-morpholin-4-ylmethyl-ethyl ester;

(4-Chlorophenyl)carbamic acid (S)-2,2,2-trifluoro-1-[2-(4-fluorophenyl)-morpholin-4-ylmethyl]-ethyl ester hydrochloride;

(4-Chlorophenyl)-carbamic acid (S)-2,2,2-trifluoro-1-[2-(3-chlorophenyl)-morpholin-4-ylmethyl]-ethyl ester hydrochloride;

(4-Chlorophenyl)-carbamic acid (S)-2,2,2-trifluoro-1-[2-(3,5-dichlorophenyl)-morpholin-4-ylmethyl]-ethyl ester hydrochloride;

(4-Chlorophenyl)carbamic acid (S)-1-[(R)-2-(3,5-dichlorophenyl)-morpholin-4-ylmethyl]-2,2,2-trifluoroethyl ester hydrochloride;

(4-Chloro-3-fluorophenyl)carbamic acid (S)-1-[(R)-2-(3,5-dichlorophenyl)-morpholin-4-ylmethyl]-2,2,2-trifluoroethyl ester hydrochloride;

(4-Chlorophenyl)-carbamic acid (S)-2,2,2-trifluoro-1-[2-(3-fluorophenyl)-morpholin-4-ylmethyl]-ethyl ester hydrochloride;

(4-Chlorophenyl)-carbamic acid (S)-1-(1,1-dioxo-1$\lambda^6$-thiomorpholin-4-ylmethyl)-2,2,2-trifluoroethyl ester hydrochloride;

(4-Chlorophenyl)-carbamic acid (S)-2,2,2-trifluoro-1-((R)-2-thiophen-2-ylmethylmorpholin-4-ylmethyl)-ethyl ester hydrochloride;

(4-Chlorophenyl)-carbamic acid (S)-2,2,2-trifluoro-1-[(R)-2-(6-methoxypyridin-3-ylmethyl)-morpholin-4-ylmethyl] ethyl ester; or (4-Chlorophenyl)-carbamic acid (S)-2,2,2-trifluoro-1-[(R)-2-(6-methoxypyridin-2-ylmethyl)-morpholin-4-ylmethyl] ethyl ester.

Representative compounds of the invention have been shown to modulate TRPA1 activity. Accordingly, the compounds of the invention are useful for treating diseases and conditions mediated by TRPA1 activity. Such diseases and conditions include but are not limited to: pain (acute, chronic, inflammatory, or neuropathic pain); itch or various inflammatory disorders; inner ear disorders; fever or other disorders of thermoregulation; tracheobronchial or diaphragmatic dysfunction; gastrointestinal or urinary tract disorders; chronic obstructive pulmonary disease; incontinence; and disorders associated with reduced blood flow to the CNS or CNS hypoxia.

In a specific embodiment, compounds of the invention can be administered to treat pain, including but not limited to neuropathic and inflammatory pain, among others. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. Exp. Mol. Pathol. 2006, 81(2), 166-170), fibromyalgia, migraine and headache (e.g. cluster headache, sinus headache, or tension headache; see, Goadsby Curr. Pain Headache Reports 2004, 8, 393), sinusitis, oral mucositis, toothache, dental trauma, dental extractions, dental infections, burn (Bolcskei et al., Pain 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, GI tract disorders, cystitis, interstitial cystitis, cholecystitis, urinary tract infection, urethral colic, renal colic, pharyngitis, cold sores, stomatitis, external otitis, otitis media (Chan et al., Lancet, 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., J Pharmacal Exp Ther., 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barre syndrome, Raynaud's syndrome, coronary artery spasm (Printzmetal's or variant angina), visceral hyperalgesia (Pomonis, J. D. et al. J. Pharmacal. Exp. Ther. 2003, 306, 387; Walker, K. M. et al., J. Pharmacal. Exp. Ther. 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., Neurosci. Lett. 2005, 393 (1), 70-73; Asai, H. et al., Pain 2005, 117, 19-29), or bone destruction pain (see, Ghilardi, J. R. et al., J. Neurosci. 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another specific embodiment, compounds of the invention can be administered to treat itch, which may arise from various sources, such as dermatological or inflammatory disorders.

In another specific embodiment, compounds of the invention can be administered to treat inflammatory disorders, including disorders selected from the group consisting of: renal or hepatobiliary disorders, immunological disorders, medication reactions and unknown/idiopathic conditions. Inflammatory disorders treatable with an inventive agent include, for example, inflammatory bowel disease (IBO), Crohn's disease, and ulcerative colitis (Geppetti, P. et al., Br. J. Pharmacal. 2004, 141, 1313-20; Yiangou, Y. et al., Lancet 2001, 357, 1338-39; Kimball, E. S. et al., Neurogastroenterol. Motif., 2004, 16, 811), osteoarthritis (Szabo, A. et al., J. Pharmacal. Exp. Ther. 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another specific embodiment, compounds of the invention can be administered to treat inner ear disorders. Such disorders include, for example, hyperacusis, tinnitus, vestibular hypersensitivity, and episodic vertigo.

In another specific embodiment, compounds of the invention can be administered to treat tracheobronchial and diaphragmatic dysfunctions including, for example, asthma and allergy-related immune responses (Agopyan, N. et al., Am. J. Physiol. Lung Cell Mol. Physiol. 2004, 286, L563-72; Agopyan, N. et al., Toxicol. Appl. Pharmacal. 2003, 192, 21-35), cough (e.g., acute or chronic cough, or cough caused by irritation from gastroesophageal reflux disease; see, Lalloo, U. G. et al., J. Appl. Physiol. 1995, 79(4), 1082-7), bronchospasm, chronic obstructive pulmonary disease, chronic bronchitis, emphysema, and hiccups (hiccoughs, singultus).

In another specific embodiment, compounds of the invention can be administered to treat gastrointestinal and urinary tract disorders such as, bladder overactivity, inflammatory hyperalgesia, visceral hyperreflexia of the urinary bladder, hemorrhagic cystitis (Dinis, P. et al., J Neurosci., 2004, 24, 11253-11263), interstitial cystitis (Sculptoreanu, A. et al., Neurosci Lett., 2005, 381, 42-46), inflammatory prostate disease, prostatitis (Sanchez, M. et al., Eur J Pharmacal., 2005, 515, 20-27), nausea, vomiting, intestinal cramping, intestinal bloating, bladder spasms, urinary urgency, defecation urgency and urge incontinence.

In another specific embodiment, compounds of the invention can be administered to treat disorders associated with reduced blood flow to the CNS or CNS hypoxia. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, compounds of the invention can be administered to treat other diseases, disorders, or conditions mediated through TRPA1 activity, such as: anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In one specific embodiment, compounds of the invention are administered to treat pain (including but not limited to acute, chronic, neuropathic and inflammatory pain), arthritis, itch, cough, asthma, or inflammatory bowel disease.

In another embodiment, the invention provides for a method for treating neurpathic pain or inflammatory pain, comprising the step of administering a therapeutically effective amount of a compound according to formula (I) to a subject in need thereof.

In another embodiment, the invention provides for a pharmaceutical composition, comprising a therapeutically effective amount of a compound according to formula (I) and a pharmaceutically acceptable carrier.

In another embodiment, the invention provides for a compound according to formula (I) for use as a therapeutically active substance.

In another embodiment, the invention provides for the use of a compound according to formula (I) for the treatment or prophylaxis of a respiratory disorder.

In another embodiment, the invention provides for the use of a compound according to formula (I) for the preparation of a medicament for the treatment or prophylaxis of a respiratory disorder.

In another embodiment, the invention provides for a compound according to formula (I) for the treatment or prophylaxis of a respiratory disorder.

Examples of respiratory disorders are chronic obstructive pulmonary disorder (COPD), asthma, allergic rhinitis and bronchospasm.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound according to formula (I) to a subject in need thereof.

In another embodiment, provided is an invention as hereinbefore described.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Compounds of the invention may be made by any number of conventional means. For example, they may be made according to the processes outlined in Schemes 1 to 4 below.

Scheme 1

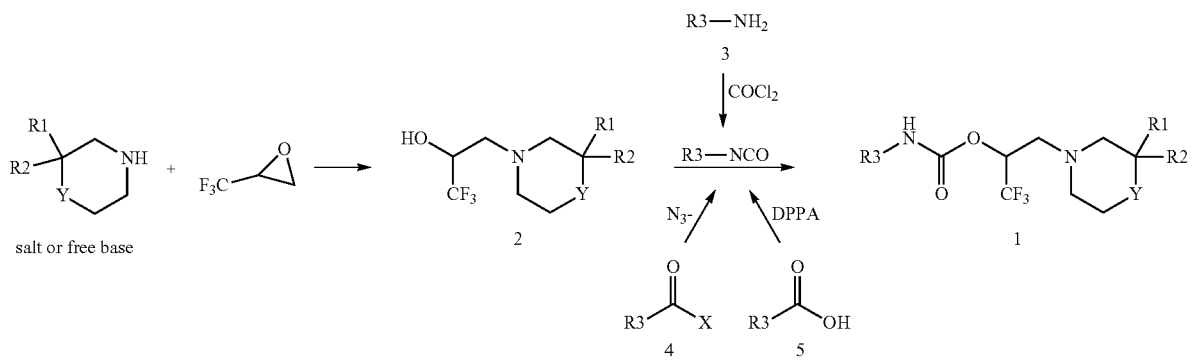

According to Scheme 1, a substituted cyclic amine as a free base or a salt may be reacted with 2-trifluoromethyloxirane to yield a substituted cyclic amino-1,1,1-trifluoropropan-2-ol of formula 2. This transformation is well-documented in the chemical literature and familiar to those skilled in the art. It proceeds under various reactions conditions, for example, the cyclic amine free base and an epoxide can be combined in an aprotic solvent such as dichloromethane or acetonitrile or neat at room temperature or with heating. Alternatively, a common salt of the cyclic amine can be combined in an aprotic solvent such as dichlormethane, tetrahydrofuran or acetonitrile in the presence of a base such as diisoproplyethylamine, triethylamine or cesium carbonate and may be followed by addition of trifluoromethyloxirane. The reaction can proceed at room temperature or with heat. Starting 2-trifluoromethyloxirane is commercially available. A large variety and number of R1,R2-substituted cyclic amines may be purchased from commercial sources or prepared by known procedures. Examples of commercially available cyclic amines include 2-(3,5-dichlorophenyl)morpholine oxalate, 2-(3-chlorophenyl)-morpholine hydrochloride, 2-(3-chloment affords the isocyanate. The corresponding carboxylic acid 5 may also be subjected to Curtius-type rearrangements using diphenylphosphoryl azide (DPPA) or a similar reagent.

Scheme 2

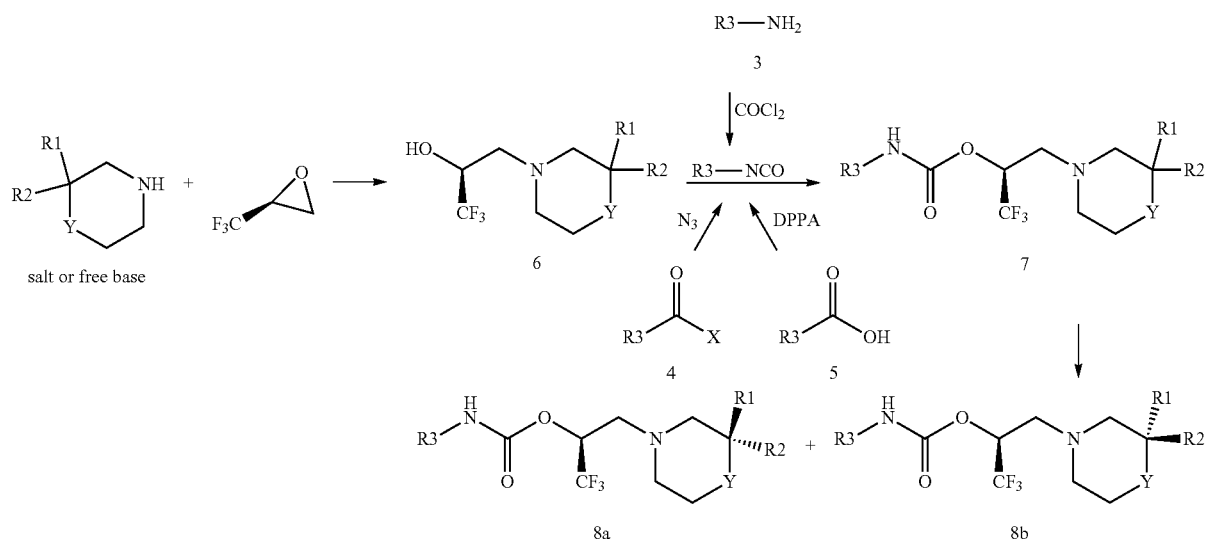

rophenyl)morpholine, 2-(3-chloro-4-fluorophenyl)morpholine, 2-(3,5-dichlorophenyl)-morpholine, 2-benzylmorpholine, 2-(3-trifluoromethylphenyl)-morpholine hydrochloride, 2-(3-methoxyphenyl)morpholine, 2-[4-(trifluoromethyl) phenyl]morpholine oxalate, 2-(3,4-difluorophenyl)morpholine, 2-(4-fluorophenyl)morpholine, morpholine, and thiomorpholine 1,1-dioxide. Substituted morpholines and thiomorpholine dioxides can be prepared using published procedures [example: Iwema Bakker, Wouter I.; Coolen, Hein K. A. C.; Mons, Harmen; Stoit, Axel; Ronken, Eric Van der Kam, Elizabeth; Frankena, Jurjen; US 2009-238518P; Lee, Eun Kyung; Schoenfeld, Ryan Craig; Weikert, Robert James US2008-80875P (example 18)]. Intermediate of formula 2 can then be reacted with isocyanates (R3NCO) by well-established methods to yield compounds of formula 1. For example, the alcohol and the isocyanate (R3NCO) can be combined in an aprotic solvent such as dichloromethane, toluene or acetonitrile at room temperature or with heating. Alternatively the alcohol and the isocyanate (R3NCO) can be combined in an aprotic solvent such as dichloromethane, toluene or acetonitrile followed by the addition of a base such as N,N-diisopropylethylamine or triethylamine at room temperature or with heating. A large variety and number of isocyanates may be purchased from commercial sources or prepared by known procedures. Examples of commercially available isocyanates include 1-isocyanato-4-methyl-benzene and 1-chloro-4-isocyanatobenzene. Isocyanates can be prepared using published procedures. The isocyanates may be synthesized from an amine 3 by treatment with phosgene or a phosgene equivalent, such as trichloromethylchloroformate (diphosgene), bis(trichloromethyl)-carbonate (triphosgene), or N,N'-carbonyldiimidazole (CDI). The isocyanate may also be derived from a heterocyclic or aromatic carboxylic acid derivative, such as an ester, an acid halide or an anhydride by a Curtius-type rearrangement. Thus, reaction of acid derivative 4 with an azide source, followed by rearrange- Alternatively, compounds of the invention may be made according to the processes outlined in Scheme 2. A substituted cyclic amine as a free base or a salt may be reacted with a chiral (S)-2-trifluoromethyloxirane to yield a diastereomeric mixture of substituted cyclic amino-1,1,1-trifluoropropan-2-ol of formula 6. This transformation is well-documented in the chemical literature and familiar to those skilled in the art. It proceeds under various reactions conditions, for example, the cyclic amine free base and a chiral epoxide can be combined in an aprotic solvent such as dichloromethane or acetonitrile or neat at room temperature or with heating. Alternatively, a common salt of the cyclic amine can be combined in an aprotic solvent such as dichlormethane, tetrahydrofuran or acetonitrile in the presence of a base such as diisoproplyethylamine, triethylamine or cesium carbonate and may be followed by addition of (S)-2-trifluoromethyloxirane. The reaction can proceed at room temperature or with heat. Starting (S)-2-trifluoromethyloxirane is commercially available. A large variety and number of R1, R2-substituted cyclic amines may be purchased from commercial sources or prepared by known procedures. Examples of commercially available cyclic amines include 2-(3,5-dichlorophenyl)morpholine oxalate, 2-(3-chloro-phenyl)-morpholine hydrochloride, 2-(3-chlorophenyl)morpholine, 2-(3-chloro-4-fluorophenyl)morpholine, 2-(3,5-dichlorophenyl)-morpholine, 2-benzylmorpholine, 2-(3-trifluoromethylphenyl)-morpholine hydrochloride, 2-(3-methoxyphenyl)morpholine, 2-[4-(trifluoromethyl)phenyl]morpholine oxalate, 2-(3,4-difluorophenyl)morpholine, 2-(4-fluorophenyl)morpholine, morpholine, and thiomorpholine 1,1-dioxide. Substituted morpholines and thiomorpholine dioxides can be prepared using published procedures (example: Iwema Bakker, Wouter I.; Coolen, Hein K. A. C. Mons, Harmen; Stoit, Axel;

Ronken, Eric; Van der Kam, Elizabeth; Frankena, Jurjen: US 2009-23851P; Lee, Eun Kyung; Schoenfeld, Ryan Craig; Weikert, Robert James US2008-80875P (example 18)). Intermediate of formula 6 can then be reacted with isocyanates (R3NCO) by well-established methods to yield compounds of formula 7. For example, the alcohol and the isocyanate (R3NCO) can be combined in an aprotic solvent such as dichloromethane, toluene or acetonitrile at room temperature or with heating. Alternatively the alcohol and the isocyanate (R3NCO) can be combined in an aprotic solvent such as dichloromethane, toluene or acetonitrile followed by the addition of a base such as N,N-diisopropylethylamine or triethylamine at room temperature or with heating. A large variety and number of isocyanates may be purchased from commercial sources or prepared by known procedures. Examples of commercially available isocyanates include 1-isocyanato-4-methyl-benzene and 1-chloro-4-isocyanatobenzene. Isocyanates can be prepared using published procedures. The isocyanates may be synthesized from an amine 3 by treatment with phosgene or a phosgene equivalent, such as trichloromethylchloroformate(diphosgene), bis(trichloromethyl)-carbonate(triphosgene), or N,N'-carbonyldiimidazole (CDI). The isocyanate may also be derived from a heterocyclic or aromatic carboxylic acid derivative, such as an ester, an acid halide or an anhydride by a Curtius-type rearrangement. Thus, reaction of acid derivative 4 with an azide source, followed by rearrangement affords the isocyanate. The corresponding carboxylic acid 5 may also be subjected to Curtius-type rearrangements using diphenylphosphoryl azide (DPPA) or a similar reagent. The diasteromeric mixture (intermediate 7) can also be separated to yield 8a and 8b by known chromatographic methods of purification such as flash chromatography on silica and/or by reverse-phase preparative HPLC (high performance liquid chromatography) or super critical fluid chromatography. Chromatographic columns can be purchased from commercial sources. Examples of commercially-available columns are SF-15 silica columns, SF-25 silica columns, Prep $C_{18}$ reverse-phase column, Pirkel's Whelk chiral column and Diacel AD chiral column.

According to Scheme 3, a chiral substituted cyclic amine as a free base or a salt may be reacted with (S)-2-trifluoromethyloxirane to yield a chiral substituted cyclic amino-1,1,1-trifluoropropan-2-ol of formula 9. This transformation is well-documented in the chemical literature and familiar to those skilled in the art. It proceeds under various reactions conditions, for example, the cyclic amine free base and an epoxide can be combined in an aprotic solvent such as dichloromethane or acetonitrile or neat at room temperature or with heating. Alternatively, a common salt of the cyclic amine can be combined in an aprotic solvent such as dichlormethane, tetrahydrofuran or acetonitrile in the presence of a base such as diisoproplyethylamine, triethylamine or cesium carbonate and may be followed by addition of (S)-2-trifluoromethyloxirane. The reaction can proceed at room temperature or with heat. Starting (S)-2-trifluoromethyloxirane is commercially available. Chiral substituted morpholines can be prepared using published procedures or variations thereof [example: Stamos, Dean et al. US2009/0131440]. Intermediate of formula 9 can then be reacted with isocyanates (R3NCO) by well-established methods to yield compounds of formula 10. For example, the alcohol and the isocyanate (R3NCO) can be combined in an aprotic solvent such as dichloromethane, toluene or acetonitrile at room temperature or with heating. Alternatively the alcohol and the isocyanate (R3NCO) can be combined in an aprotic solvent such as dichloromethane, toluene or acetonitrile followed by the addition of a base such as N,N-diisopropylethylamine or triethylamine at room temperature or with heating. A large variety and number of isocyanates may be purchased from commercial sources or prepared by known procedures. Examples of commercially available isocyanates include 1-isocyanato-4-methyl-benzene and 1-chloro-4-isocyanatobenzene. Isocyanates can be prepared using published procedures. The isocyanates may be synthesized from an amine 3 by treatment with phosgene or a phosgene equivalent, such as trichloromethylchloroformate (diphosgene), bis(trichloromethyl)-carbonate (triphosgene), or N,N'-carbonyldiimidazole (CDI). The isocyanate may also be derived from a heterocyclic or aromatic carboxylic acid derivative, such as an ester, an acid halide or an anhydride by a Curtius-type rearrangement. Thus, reaction of acid derivative 4 with an azide source, followed by rearrangement affords the isocyanate. The corresponding carboxylic acid 5 may also be subjected to Curtius-type rearrangements using diphenylphosphoryl azide (DPPA) or a similar reagent.

Scheme 3

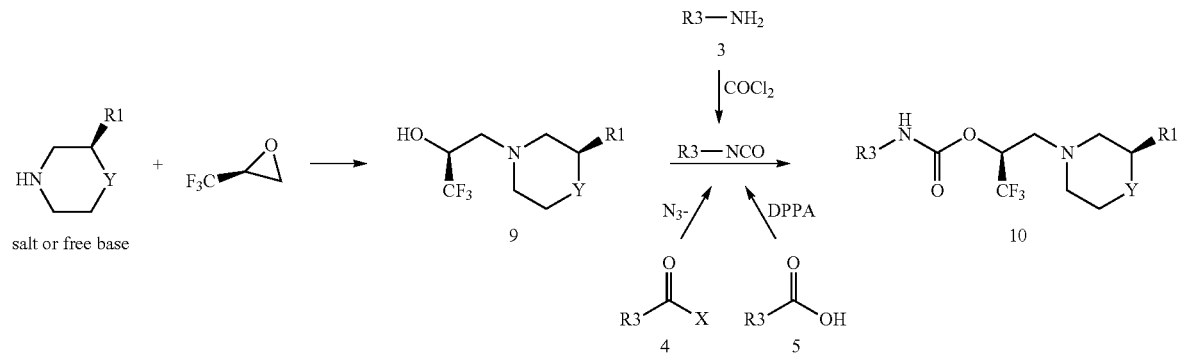

Scheme 4

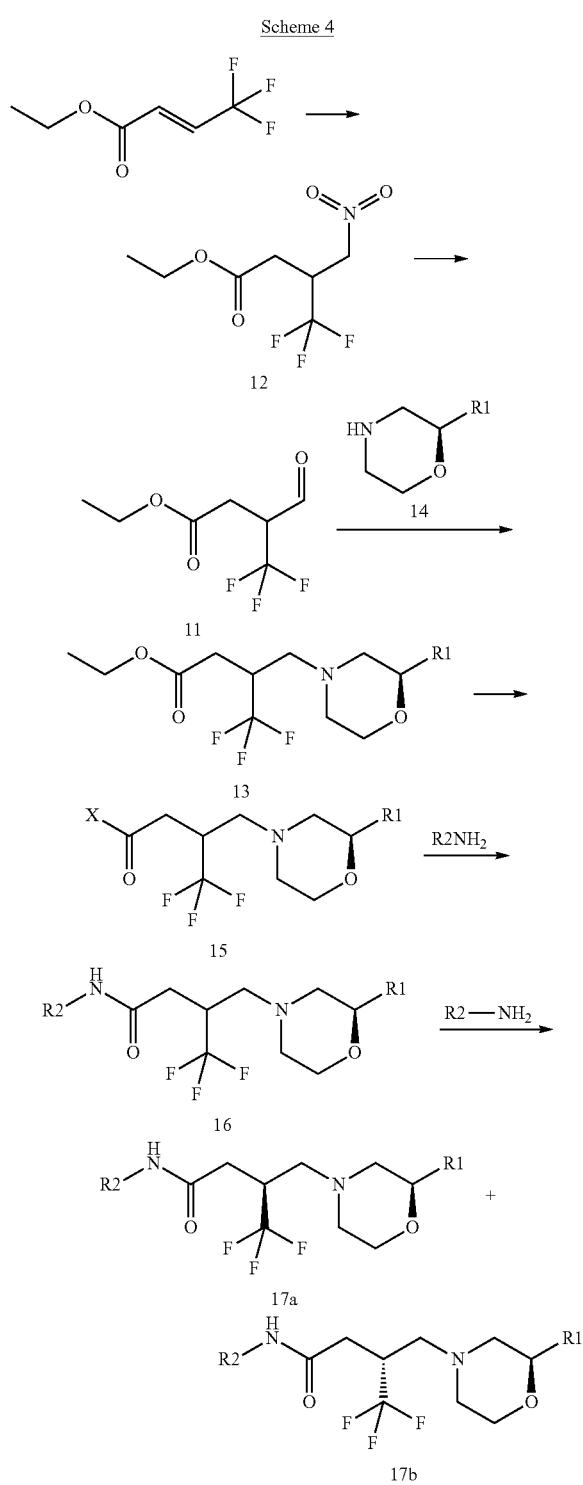

Alternatively, compounds of the invention may be made according to the processes outlined in Scheme 4. Intermediate of formula 11 could be prepared from commercially available (E)-4,4,4-trifluoro-but-2-enoic acid ethyl ester by reaction with nitromethane under Michael reaction conditions. This transformation is well-documented in the chemical literature and familiar to those skilled in the art. It proceeds under various reactions conditions, for example, nitromethane and an α,β-unsaturated ester can be combined in a solvent such as ethanol, ethyl acetate, toluene or acetonitrile or neat at room temperature or with heating in the presence of a base such as DBU, tetramethylguanidine, triethylamine, N,N-diisopropylethylamine or Triton B. Intermediate of formula 11 can then be converted to the aldehyde intermediate 12 by a sequence such as a modified Nef reaction that is described in the literature [for example: Steliou, K. and Poupart, M. A. J. Organic Chem. 1985, 50, 4971]. Intermediate of formula 12 can then be reacted with morpholines to yield γ-aminoesters of formula 13. This transformation is well-documented in the chemical literature and familiar to those skilled in the art. It proceeds under various reductive amination reaction conditions, for example, the aldehyde and the morpholine 14 can be combined in an aprotic solvent such as dichloromethane, dichloroethane, tetrahydrofuran and treated with a reducing agent such as sodium triacetoxyborohydride. Alternatively the aldehyde and the morpholine 14 could be combined in an alcoholic solvent such as ethanol and treated with a reducing agent such as sodium cyanoborohydride. Chiral substituted morpholines can be prepared using published procedures or variations thereof [example: Stamos, Dean et al. US2009/0131440]. Intermediate of formula 13 can then be reacted under hydrolysis conditions to yield intermediate of formula 15. This transformation is well-documented in the chemical literature and familiar to those skilled in the art. It proceeds under various reactions conditions, for example, the ester is combined in a solvent such as methanol, ethanol, isopropanol, tetrahydrofuran, dioxane and water and treated with a base such as sodium hydroxide or potassium hydroxide with heating or at room temperature. Intermediate of formula 15 (X=OH) can then be coupled to aromatic amines or heteroaromatic amines (R2-NH$_2$) by a variety of well-established methods to yield compounds of formula 16. For example, the acid and amine can be combined in a solvent such as dimethylformamide and treated with any number of peptide coupling reagents such as 2-(1H-7-azabenzotriazol-1-yl)-1,1,3,3-tetramethyl uronium hexafluorophosphate methanaminium or bromo-tris-pyrrolidino phosphonium-hexafluorophosphate or dicyclohexyl carbodiimide. Alternatively, intermediate of formula 15 (X=OH) can be converted to the acid chloride of formula 15 (X=Cl) using reagents such as oxalyl chloride or thionyl chloride in a solvent such as dichloromethane with dimethyl formamide and then the intermediate of formula 15 (X=Cl) can converted to the intermediate of formula 16 by reaction with aromatic amines or heteroaromatic amines (R2-NH$_2$). The diasteromeric mixture (intermediate 16) can be separated to yield 17a and 17b by known chromatographic methods of purification such as flash chromatography on silica and/or by reverse-phase preparative HPLC (high performance liquid chromatography) or super critical fluid chromatography. Chromatographic columns can be purchased from commercial sources. Examples of commercially-available columns are SF-15 silica columns, SF-25 silica columns, Prep C$_{18}$ reverse-phase column, Pirkel's Whelk chiral column and Diacel AD chiral column.

EXAMPLES

Although certain exemplary embodiments are depicted and described herein, the compounds of the present invention can be prepared using appropriate starting materials according to the methods described generally herein and/or by methods available to one of ordinary skill in the art.

Intermediates and final compounds were purified by either flash chromatography and/or by reverse-phase preparative HPLC (high performance liquid chromatography). Unless otherwise noted, flash chromatography was performed using (1) the Biotage SP1™ system and the Quad 12/25 Cartridge module (from Biotage AB), (2) the ISCO CombiFlash® chromatography instrument (from Teledyne Isco, Inc.), or (3) an Analogix® IntelliFlash280™ chromatography instrument (from Analogix Inc., a subsidiary of Varian Inc.). Unless otherwise noted, the silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Reverse-phase preparative HPLC was performed using a Waters® Delta-Prep™ 3000 HPLC system from Waters Corporation using one or more of the following columns: a Varian Pursuit® C-18 column (10 μm, 20×150 mm) from Varian, Inc., an Xbridge™ Prep $C_{18}$ column (5 μm, OBD™ 20×100 mm) from Waters Corporation, or a SunFire™ Prep $C_{18}$ column (5 μm, OBD™ 30×100 mm) from Waters Corporation.

Mass spectrometry (MS) or high resolution mass spectrometry (HRMS) was performed using a Waters® ZQ™ 4000 (from Waters Corporation), a Waters® Quattro Micro™ API (from Waters Corporation), a Micromass® Platform II (from Micromass, a division of Waters Corporation), a Bruker® Apex® II FTICR with a 4.7 Tesla magnet (from Bruker Corporation), a Waters® Alliance® 2795-ZQ™2000 (from Waters Corporation), or an MDS Sciex™ API-2000™n API (from MDS Inc.). Mass spectra data generally only indicates the parent ions unless otherwise stated. MS or HRMS data is provided for a particular intermediate or compound where indicated.

Nuclear magnetic resonance spectroscopy (NMR) was performed using a Varian® Mercury300 NMR spectrometer (for the $^1$H NMR spectra acquired at 300 MHz) and a Varian® Inova400 NMR spectrometer (for the $^1$H NMR spectra acquired at 400 MHz) both from Varian Inc. NMR data is provided for a particular intermediate or compound where indicated.

All reactions involving air-sensitive reagents were performed under an inert atmosphere. Reagents were used as received from commercial suppliers unless otherwise noted.

Absolute stereochemistry, where assigned, is based on comparison of biological potency and/or relative retention time on silica gel TLC and chromatography to analogs prepared from chiral building blocks of known absolute configuration, described in Examples 1-6 as evidenced by Example 7.

I. Preparation of Certain Intermediates

Intermediate A

1-Chloro-2-fluoro-4-isocyanatobenzene

4-Chloro-3-fluoroaniline (2 g, 13.7 mmol) was dissolved in 60 mL of dichloromethane. Under ice bath, saturated sodium bicarbonate solution (60 mL) was added. The mixture was stirred at 0° C. and triphosgene (1.36 g, 4.58 mmol) was added. The mixture was stirred at 0° C. for 1 h and then extracted with dichloromethane and water. The organic layer was dried with sodium sulfate and filtered. The filtrate solution was concentrated and the residue was treated with 50 mL of hexanes. The hexane solution was concentrated to remove all solvents. The residue was taken up in 12 mL of hexanes and filtered. The solution was concentrated and dried to give 1-chloro-2-fluoro-4-isocyanatobenzene as an off white solid (1.69 g). $^1$H NMR (400 MHz, CHLOROFORM-d) δ ppm 6.82-6.90 (m, 1H) 6.93 (dd, J=9.22, 2.65 Hz, 1H) 7.31-7.41 (m, 1H).

Intermediate B 1-(2-Trifluoromethylpyrimidin-4-yl)-ethanone

In a 350 mL sealed tube, 4-chloro-2-(trifluoromethyl)pyrimidine (4 g, 21.9 mmol) and tributyl(1-ethoxyvinyl)stannane (8.55 g, 23.7 mmol) were combined with DMF (75 ml) to give a light yellow solution. The tube was placed under argon and the solution degassed with argon. Bis(triphenylphosphine)palladium(II) dichloride (308 mg, 438 μmol) was added. The solution was degassed with argon for 5 min. The tube was sealed and warmed at 85° C. (bath temperature) overnight (protected from light). Complete by LCMS.

Reaction mixture was cooled to room temperature and then poured into an aqueous solution of KF (18 g in 180 mL). Ether (300 mL) was added and the grey/white precipitate was filtered off. Solid was washed several times with ether. The biphasic mixture of filtrate and washes were poured onto water and extracted 3 times with ether. The combined ethereal layers were washed with brine, dried over $MgSO_4$ and concentrated in vacuo. The crude product was taken on to the next step without further purification.

The product from the previous step was taken up in 120 mL acetone. Aqueous HCl (18 mL of 2 N) was added. The reaction mixture was warmed at 60° C. for 2 h. No starting material was present by LCMS. The solvent was evaporated to reduced volume, poured onto saturated $NaHCO_3$ and extracted 3 times with dichloromethane. The combined organic extracts were dried over $Na_2SO_4$ and concentrated in vacuo. The crude material was purified by flash chromatography (silica gel, 40 g, 7% ethyl acetate (EtOAc) in hexanes). Product fractions were combined and concentrated under reduced pressure to afford 1-(2-trifluoromethyl-pyrimidin-4-yl)-ethanone (3.4 g, 82%) as an amber liquid. $^1$H NMR (400 MHz, CHLOROFORM-d) δ ppm 2.80 (s, 3H) 8.09 (d, J=5.05 Hz, 1H) 9.17 (d, J=5.05 Hz, 1H).

Intermediate C (R)-2-(3-Trifluoromethylphenyl)-oxirane

Solutions of 4.006 g (15 mmol) of 2-bromo-1-(3-trifluoromethylphenyl)-ethanone, 15 mL of anhydrous tetrahydrofuran and 15 mL of 1M borane-THF in tetrahydrofuran were added simultaneously to a stirring solution of 1.5 mL of 1M (R)-(3aR)-tetrahydro-1-methyl-3,3-diphenyl-1H,3H-pyrrolo[1,2-c][1,3,2]oxazaborole in toluene and 15 mL of anhydrous tetrahydrofuran, cooled in an ice water bath at ca. 15 degrees, over 12.5 minutes. The cooling bath was removed and the mixture stirred at room temperature. After 1.5 h, ca. 0.48 g of methanol was added dropwise (gas evolution) and the mixture stirred for 5 minutes, then 15 mL of 2 M sodium hydroxide was added over 3 minutes. The mixture was stirred at room temperature. After 1.5 h, the mixture was concentrated under reduced pressure to remove the tetrahydrofuran, and the remaining aqueous phase was extracted twice with diethyl ether. The combined ether extracts were dried over anhydrous magnesium sulfate, filtered and concentrated under reduced pressure to give 2.553 g (90%) of (R)-2-(3-trifluoromethyl-phenyl)oxirane as a light amber liquid. $^1$H NMR (400 MHz, DMSO-$d_6$) δ ppm 2.87 (dd, J=5.27, 2.51

Hz, 1H) 3.12 (dd, J=5.27, 4.02 Hz, 1H) 4.04 (dd, J=4.27, 2.51 Hz, 1H) 7.54-7.58 (m, 2H) 7.60 (s, 1H) 7.62-7.67 (m, 1H).

II. Preparation of Certain Embodiments of the Invention

Example 1

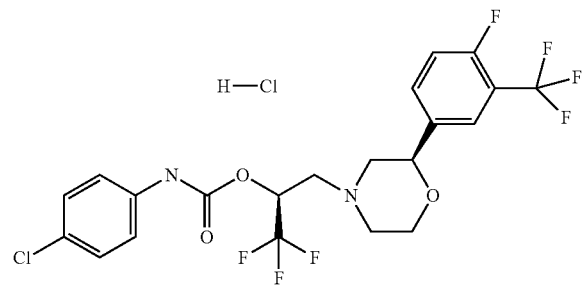 [SMILES: O=C(Nc1ccc(Cl)cc1)O[C@@H](CN1CCO[C@H](c2ccc(F)c(C(F)(F)F)c2)C1)C(F)(F)F ; Cl]

(4-Chlorophenyl)-carbamic acid (S)-2,2,2-trifluoro-1-[(R)-2-(4-fluoro-3-trifluoromethylphenyl)-morpholin-4-ylmethyl]-ethyl ester hydrochloride Step a 1-(4-fluoro-3-(trifluoromethyl)phenyl)ethanone (5.38 g, 26. mmole) and hydroxy(tosyloxy)iodo]benzene (10.2 g, 26.1 mmol) were combined in 80 mL of acetonitrile. The mixture was heated at reflux with stirring for 5 h. The mixture was kept at room temperature overnight. The mixture was decanted to remove the trace amount of solid. The clear solution was concentrated to remove the solvent. The residue was treated with ether (15 mL) and the white solid was filtered to give the first batch of toluene-4-sulfonic acid 2-(4-fluoro-3-trifluoromethyl-phenyl)-2-oxo-ethyl ester (4.0 g). The mother liquor was concentrated and treated with ether and hexanes (1:1 ratio) to give the second batch of toluene-4-sulfonic acid 2-(4-fluoro-3-trifluoromethyl-phenyl)-2-oxo-ethyl ester as a white solid (1.3 g). $^1$H NMR (400 MHz, CHLOROFORM-d) δ ppm 2.48 (s, 3H) 5.22 (s, 2H) 7.31-7.43 (m, 3H) 7.85 (d, J=8.34 Hz, 2H) 8.05-8.18 (m, 2H).

Step b

To a solution of (R)-(3aR)-tetrahydro-1-methyl-3,3-diphenyl-1H,3H-pyrrolo[1,2-c][1,3,2]oxazaborole (295 mg, 1.06 mmol) in THF (10 mL) was added borane in THF (1M, 11 mL, 11 mmol). The resulting solution was stirred and 2-(4-fluoro-3-(trifluoromethyl)phenyl)-2-oxoethyl 4-methylbenzenesulfonate (4.0 g, 10.6 mmol) in THF (30 mL) was added through a dropping funnel over 45 min. The solution was stirred at room temperature for 45 min. The mixture was quenched with methanol (5 mL) and concentrated. The resulting residue was extracted with ethyl acetate and 0.5N hydrochloric acid. The organic layer was dried and concentrated to give toluene-4-sulfonic acid (R)-2-(4-fluoro-3-trifluoromethyl-phenyl)-2-hydroxyethyl ester (3.85 g). $^1$H NMR (400 MHz, CHLOROFORM-d) δ ppm 2.46 (s, 3H) 3.99-4.19 (m, 2H) 5.03 (dd, J=8.08, 3.54 Hz, 1H) 7.11-7.22 (m, 1H) 7.35 (dd, J=8.59, 0.76 Hz, 2H) 7.49-7.55 (m, 1H) 7.57 (dd, J=6.69, 1.89 Hz, 1H) 7.76 (d, J=8.34 Hz, 2H).

Step c (R)-2-(4-Fluoro-3-(trifluoromethyl)phenyl)-2-hydroxyethyl 4-methylbenzenesulfonate (3.5 g, 9.25 mmol) was dissolved in 20 mL of DMSO. Sodium azide (1.2 g, 18.5 mmol) was added and the mixture was stirred at 80° C. for 3 h. The clear solution was cooled to room temperature and extracted with ethyl acetate and water. The organic layer was dried and concentrated to give (R)-2-azido-1-(4-fluoro-3-trifluoromethylphenyl)-ethanol as a pale brown oil (2.27 g) which was used as is in the next step.

$^1$H NMR (300 MHz, CHLOROFORM-d) δ ppm 3.47 (d, J=3.02 Hz, 1H) 3.49 (s, 1H) 4.92 (dd, J=6.80, 4.91 Hz, 1H) 7.23 (t, J=9.25 Hz, 1H) 7.53-7.62 (m, 1H) 7.65 (dd, J=6.61, 2.08 Hz, 1H).

Step d (R)-2-Azido-1-(4-fluoro-3-(trifluoromethyl)phenyl)ethanol (2.20 g, 8.83 mmol) was dissolved in methanol (25 mL) and 10% Pd on carbon (200 mg) was added. The mixture was stirred under hydrogen balloon for 20 h. LC/MS indicated desired compound. TLC indicated complete consumption of the starting material. The mixture was filtered through a pad of Celite and rinsed with methanol. Solvents were evaporated to give (R)-2-amino-1-(4-fluoro-3-trifluoromethyl-phenyl)-ethanol as a white crystalline material (1.97 g). (M+H)$^+$=224 m/e.

Step e (R)-2-amino-1-(4-fluoro-3-(trifluoromethyl)phenyl)ethanol (2.27 g, 10.2 mmol) was dissolved in 50 mL of dichloromethane. Water (50 mL) containing sodium bicarbonate (1.11 g, 13.2 mmol) was added. The mixture was stirred under ice bath and 2-chloroacetyl chloride (1.38 g, 12.2 mmol) in dichloromethane (10 mL) was added dropwise. The mixture was stirred for 20 min. The pH value was checked and concentrated sodium bicarbonate solution was added (15 mL) to adjust pH to basic. The ice bath was removed and the mixture was stirred for 15 min. TLC indicated consumption of the starting material. The mixture was extracted with dichloromethane and sodium bicarbonate solution. The organic layer was washed with brine and dried. Solvents were evaporated and the resulting material was purified through ISCO flash column chromatography (40 g silica gel, 20% to 90% ethyl acetate in hexanes gradient) to give 2-chloro-N—[(R)-2-(4-fluoro-3-trifluoromethylphenyl)-2-hydroxy-ethyl]-acetamide as an oily material, which gradually solidified (2.64 g). $^1$H NMR (300 MHz, CHLOROFORM-d) δ ppm 3.18 (br. s., 1H) 3.40 (ddd, J=14.07, 8.21, 5.29 Hz, 1H) 3.72 (ddd, J=14.16, 6.99, 3.40 Hz, 1H) 4.09 (s, 2H) 4.95 (dd, J=7.93, 3.02 Hz, 1H) 7.03 (br. s., 1H) 7.16-7.26 (m, 1H) 7.54-7.62 (m, 1H) 7.66 (dd, J=6.61, 2.08 Hz, 1H).

Step f (R)-2-Chloro-N-(2-(4-fluoro-3-(trifluoromethyl)phenyl)-2-hydroxyethyl)acetamide (2.45 g, 8.2 mmol) was dissolved in dry THF (30 mL). Under ice bath, sodium hydride (330 mg, 60% in mineral oil, 8.2 mmol) was added. The mixture was stirred at room temperature for 1 h and then warmed to room temperature and further stirred for 2 h. TLC indicated complete consumption of the starting material. The mixture was concentrated and extracted with ethyl acetate and water. The organic layer was dried and concentrated. The oily residue was dried in vacuum (2.25 g). This material was purified through ISCO flash column chromatography (80 g silica gel, methanol in dichloromethane, 0% to 5% gradient). The desired fraction was concentrated and crystallized from ether and hexanes to give (R)-6-(4-fluoro-3-trifluoromethyl-phenyl)-morpholin-3-one as a white solid (492 mg). $^1$H NMR (300 MHz, CHLOROFORM-d) δ ppm 3.41-3.64 (m, 2H) 4.24-4.59 (m, 2H) 4.81 (dd, J=9.06, 4.53 Hz, 1H) 6.51 (br. s., 1H) 7.17-7.27 (m, 1H) 7.51-7.62 (m, 1H) 7.66 (dd, J=6.61, 2.08 Hz, 1H). The mother liquor was concentrated to give a waxy material (230 mg), which TLC indicated it was mostly desired compound.

Step g (R)-6-(4-Fluoro-3-(trifluoromethyl)phenyl)morpholin-3-one (486 mg, 1.85 mmol) was dissolved in 2 mL of THF and 10 mL of ether. To this solution under ice bath was added powder LiAlH$_4$ (72 mg, 1.85 mmol). The mixture was stirred at 0° C. for 1 h and then at room temperature overnight. LC/MS indicated only the starting material. To this mixture was added LiAlH$_4$ (1M) in THF (2 mL, 2 mmol) under ice bath. The mixture was stirred at room temperature for 15 h. LC/MS indicated complete consumption of the starting material and the formation of the desired MW (250, M+1). Under ice bath, 2.5 mL of water was added and the mixture was stirred for 30 min. The top solution was decanted and concentrated. The slurry residue was treated with methylene chloride and water. The organic layer was combined with the dichloromethane solution from the decanted top solution, washed and dried. Solvents were evaporated to give (R)-2-(4-fluoro-3-(trifluoromethyl)phenyl)morpholine as a pale green oil (460 mg). $^1$H NMR (400 MHz, CHLOROFORM-d) δ ppm 2.74 (dd, J=12.13, 10.36 Hz, 1H) 2.86-2.96 (m, 1H) 2.96-3.03 (m, 1H) 3.08 (dd, J=12.38, 2.53 Hz, 1H) 3.80 (td, J=11.37, 3.03 Hz, 1H) 4.06 (dd, J=11.37, 3.03 Hz, 1H) 4.52 (dd, J=10.36, 2.53 Hz, 1H) 7.14-7.23 (m, 1H) 7.50-7.58 (m, 1H) 7.64 (dd, J=6.69, 2.15 Hz, 1H).

Step h (R)-2-(4-fluoro-3-(trifluoromethyl)phenyl)morpholine (455 mg, 1.83 mmol) and (S)-2-(trifluoromethyl)oxirane (245 mg, 2.19 mmol) were combined and stirred at 60° C. overnight. The mixture was purified through ISCO flash column chromatography (ethyl acetate in hexanes 0% to 40% gradient) to give the desired compound (S)-1,1,1-trifluoro-3-[(R)-2-(4-fluoro-3-trifluoromethyl-phenyl)-morpholin-4-yl]-propan-2-ol as the major component as a colorless oil (430 mg). (M+H)$^+$=362 m/e.

Step i (S)-1,1,1-Trifluoro-3-((R)-2-(4-fluoro-3-(trifluoromethyl)phenyl)morpholino)propan-2-ol (427 mg, 1.18 mmol) was mixed with 1-chloro-4-isocyanatobenzene (180 mg, 1.17 mmol) in toluene (5 mL). The mixture was stirred at 90° C. for 2 h. TLC indicated still significant amount of the starting material. So a second batch of 1-chloro-4-isocyanatobenzene (180 mg, 1.17 mmol) was added and the mixture was further stirred at 95° C. for 2 h. TLC indicated still significant amount of starting material. A second batch of isocyanate was added and the mixture was stirred at 90° C. for 2 h. The mixture was concentrated and the residue was extracted with ethyl acetate and water, washed with sodium bicarbonate solution and brine, dried and concentrated. The residue was purified through ISCO flash column chromatography (ethyl acetate in hexanes 0% to 40% gradient in 16 min). The desired fraction was concentrated to give (4-chlorophenyl)-carbamic acid (S)-2,2,2-trifluoro-1-[(R)-2-(4-fluoro-3-trifluoromethyl-phenyl)-morpholin-4-ylmethyl]-ethyl ester a colorless oil, which was dissolved in ether and 1N HCl in ether (1 mL) was added. Solvent was evaporated and the residue was dissolved in ether. Hexane was added and solvents were evaporated to give a white solid 241 mg. LC/MS indicated 13% des-fluoro ((M+H)$^+$=497 m/e) and 87% desired compound ((M+H)$^+$=515 m/e).

This batch (200 mg) was further purified by chiral supercritical fluid chromatography (SFC) using a chiral AD column, 8% MeOH in carbon dioxide containing 0.2% triethylamine (TEA) to give a major fraction, which was converted to hydrochloride salt, (4-chlorophenyl)-carbamic acid (S)-2,2,2-trifluoro-1-[(R)-2-(4-fluoro-3-trifluoromethylphenyl)-morpholin-4-ylmethyl]-ethyl ester hydrochloride, as a white solid (100 mg). (M+H)$^+$=515 m/e.

Example 2

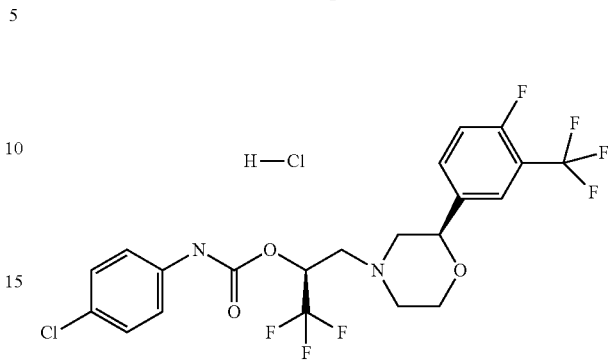

(4-Chlorophenyl)-carbamic acid (S)-2,2,2-trifluoro-1-[2-(4-fluoro-3-trifluoromethylphenyl)-morpholin-4-ylmethyl]-ethyl ester hydrochloride This batch (200 mg) that was further purified by chiral SFC as described in Example 1 (step i) using chiral AD column, 8% MeOH in carbon dioxide containing 0.2% TEA afforded an additional front-running minor fraction, which was converted to hydrochloride salt, (4-chloro-phenyl)-carbamic acid (S)-2,2,2-trifluoro-1-[2-(4-fluoro-3-trifluoromethyl-phenyl)-morpholin-4-ylmethyl]-ethyl ester hydrochloride, as a white solid. The product was a 1:1 mixture of epimers as determined by 1H NMR. (M+H)$^+$=515 m/e.

Example 3

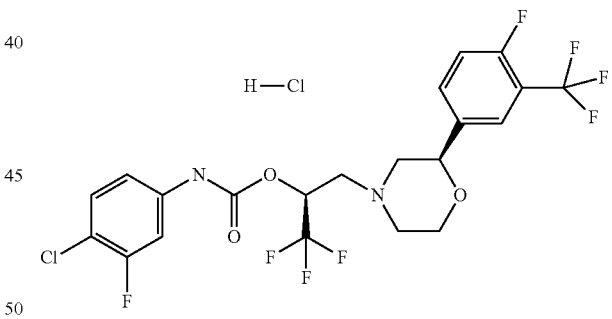

(4-Chloro-3-fluorophenyl)-carbamic acid (S)-2,2,2-trifluoro-1-[(R)-2-(4-fluoro-3-trifluoromethylphenyl)-morpholin-4-ylmethyl]-ethyl ester hydrochloride (S)-1,1,1-trifluoro-3-((R)-2-(4-fluoro-3-(trifluoromethyl)phenyl)morpholino)propan-2-ol was prepared as previously described in Example 1 (steps a-g) to afford 150 mg of a green oil, determined by LCMS and $^1$H NMR to be a 2:1 mixture of (S)-1,1,1-trifluoro-3-((R)-2-(4-fluoro-3-(trifluoromethyl)phenyl)morpholino)propan-2-ol and (S)-1,1,1-trifluoro-3-((R)-2-(3-(trifluoromethyl)phenyl)morpholino)propan-2-ol, which was used as is. This mixture (150 mg, 0.41 mmol) was mixed with 1-chloro-2-fluoro-4-isocyanatobenzene (78.4 mg, 0.45 mmol) in 4 mL of dichloromethane. The solution was stirred and N,N-diisopropylethylamine (DIPEA) (0.1 mL, 0.45 mmol) was added. The reaction tube was sealed and the solution was stirred at 60° C. overnight. Solvents were evaporated and the residue was purified by flash column chromatography (0% to 30% ethyl acetate in hexanes gradient) to give an oily material. LC/MS indicated two component as 2:1 ratio (4-chloro-3-fluoro-phenyl)-carbamic acid (S)-2,2,2-trifluoro-1-[(R)-2-(4-fluoro-3-trifluoromethyl-phenyl)-morpholin-4-ylmethyl]-ethyl ester hydrochloride and (4-chloro-3-fluoro-phenyl)-carbamic acid (S)-2,2,2-trifluoro-1-[(R)-2-(3-trifluoromethyl-phenyl)-morpholin-4-ylmethyl]-ethyl ester. The material was purified by chiral SFC (DAICEL OJ column, 10% methanol in carbon dioxide, 70 mL/min). The major fraction was the front peak, which concentrated and dissolved in ether. 1N HCl in ether was added and solvents were evaporated to afford (4-chloro-3-fluoro-phenyl)-carbamic acid (S)-2,2,2-trifluoro-1-[(R)-2-(4-fluoro-3-trifluoromethyl-phenyl)-morpholin-4-ylmethyl]-ethyl ester hydrochloride as a white powder (63 mg). (M+H)$^+$=533 m/e.

Example 4

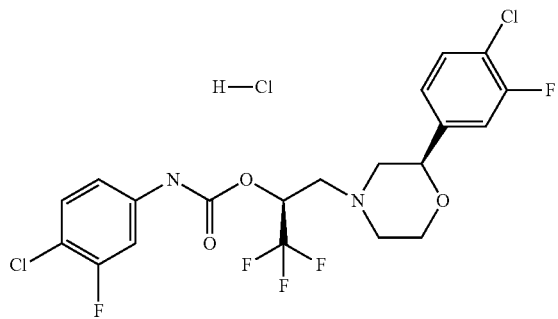 [SMILES: O=C(Nc1ccc(Cl)c(F)c1)O[C@@H](CN1CCO[C@H](c2ccc(Cl)c(F)c2)C1)C(F)(F)F ; Cl]

(4-Chloro-3-fluorophenyl)-carbamic acid (S)-1-[(R)-2-(4-chloro-3-fluorophenyl)-morpholin-4-ylmethyl]-2,2,2-trifluoroethyl ester hydrochloride Step a (R)-2-(4-chloro-3-fluorophenyl)-2-hydroxyethyl 4-methylbenzenesulfonate (prepared as previously described in Example 1 (steps a-b) except substituting 1-(3-chloro-4-fluorophenyl)ethanone for 1-(4-fluoro-3-(trifluoromethyl)phenyl)ethanone, 3.35 g, 9.72 mmol) was dissolved in ether (80 mL) and 2N NaOH solution (25 mL) was added. The mixture was stirred at room temperature for 6 h until all starting material was consumed. The mixture was separated and the ether layer was washed with water. The organic layer was dried with sodium sulfate and solvents were removed to afford (R)-2-(4-chloro-3-fluorophenyl)oxirane as a colorless oil which was dried in vacuum (1.66 g). $^1$H NMR (400 MHz, CHLOROFORM-d) δ ppm 2.71-2.80 (m, 1H) 3.18 (dd, J=5.31, 4.04 Hz, 1H) 3.82-3.89 (m, 1H) 7.01-7.12 (m, 2H) 7.39 (dd, J=8.46, 7.45 Hz, 1H).

Step b (R)-2-(4-chloro-3-fluorophenyl)oxirane (1.66 g, 9.62 mmol) was added dropwise to ethanolamine (3.5 mL, 53.9 mmol). The (R)-2-(4-chloro-3-fluorophenyl)oxirane residue was rinsed with 4 mL of THF and this was added to the reaction mixture. The clear solution was stirred at room temperature for 48 h. TLC indicated complete consumption of the starting material. The mixture was treated with water (30 mL) under ice bath and then extracted with ethyl acetate (40 mL). The aqueous layer was extracted with ethyl acetate (30 mL). The combined organic phase was washed with water and brine, dried and concentrated in vacuo to afford (R)-1-(4-chloro-3-fluorophenyl)-2-(2-hydroxyethylamino)ethanol (2.06 g) as a colorless oil. $^1$H NMR (300 MHz, CHLOROFORM-d) δ ppm 2.54 (br. s., 3H) 2.64-2.77 (m, 1H) 2.84 (td, J=5.00, 3.59 Hz, 2H) 2.93 (dd, J=12.27, 3.59 Hz, 1H) 3.72 (t, J=5.10 Hz, 2H) 4.72 (dd, J=8.88, 3.59 Hz, 1H) 7.08 (dd, J=8.31, 1.89 Hz, 1H) 7.20 (dd, J=9.82, 1.89 Hz, 1H) 7.31-7.43 (m, 1H).

Step c (R)-1-(4-chloro-3-fluorophenyl)-2-(2-hydroxyethylamino)ethanol (2.06 g, 8.82 mmol) was dissolved in 50 mL of dichloromethane. To this stirred solution was added di-tert-butyl dicarbonate (1.92 g, 8.82 mmol) in dichloromethane (6 mL). The solution was stirred at room temperature overnight. Solvents were evaporated and the residue was purified by ISCO flash column chromatography (0% to 60% ethyl acetate in hexanes gradient) to afford (R)-tert-butyl 2-(4-chloro-3-fluorophenyl)-2-hydroxyethyl(2-hydroxyethyl)carbamate a colorless oil (2.50 g). Product was used as is in the next step.

Step d (R)-tert-butyl 2-(4-chloro-3-fluorophenyl)-2-hydroxyethyl(2-hydroxyethyl)carbamate (2.5 g, 7.49 mmol) was dissolved in methyl-t-butylether (20 mL) and triphenylphosphine (2.36 g, 8.99 mmol) was added. To this mixture was added diisopropyl azodicarboxylate (1.8 mL, 8.99 mmol) by dropwise addition. The solution was stirred at room temperature for 1 h. The white solid was filtered off and the filtrate was concentrated. The residue was purified by ISCO flash column chromatography (220 g silica gel, 0% to 20% ethyl acetate in hexanes) to afford (R)-tert-butyl 2-(4-chloro-3-fluorophenyl)morpholine-4-carboxylate as a white solid (1.02 g). $^1$H NMR (300 MHz, CHLOROFORM-d) δ ppm 1.49 (s, 9H) 2.75 (t, J=11.71 Hz, 1H) 2.94-3.11 (m, 1H) 3.67 (td, J=11.71, 3.02 Hz, 1H) 3.86-4.17 (m, 3H) 4.40 (dd, J=10.58, 2.64 Hz, 1H) 7.09 (dd, J=8.31, 1.51 Hz, 1H) 7.21 (dd, J=9.82, 1.89 Hz, 1H) 7.38 (t, J=7.93 Hz, 1H).

Step e (R)-tert-butyl 2-(4-chloro-3-fluorophenyl)morpholine-4-carboxylate (990 mg) was dissolved in 2 mL of dichloromethane and TFA (2 mL) was added. The solution was stirred at room temperature for 2 h. Solvents were evaporated. The residue was extracted with dichloromethane and 1N NaOH solution. The organic layer was dried and concentrated. The residue was dried in vacuum to afford (R)-2-(4-chloro-3-fluorophenyl)morpholine an oil (669 mg). $^1$H NMR (400 MHz, CHLOROFORM-d) δ ppm 2.11 (br. s., 1H) 2.72 (dd, J=12.38, 10.36 Hz, 1H) 2.86-3.04 (m, 2H) 3.07 (dd, J=12.38, 2.53 Hz, 1H) 3.79 (td, J=11.37, 3.03 Hz, 1H) 4.05 (dd, J=11.49, 2.40 Hz, 1H) 4.48 (dd, J=10.36, 2.53 Hz, 1H) 7.02-7.13 (m, 1H) 7.15-7.23 (m, 1H) 7.33-7.42 (m, 1H).

Step f (R)-2-(4-chloro-3-fluorophenyl)morpholine (230 mg, 1.07 mmol) was mixed with (S)-2-(trifluoromethyl)oxirane (180 mg, 1.6 mmol) in 1 mL of dichloromethane in a tube. The tube was sealed and stirred at 60° C. overnight. The solution was evaporated to dryness to afford (S)-3-((R)-2-(4-chloro-3-fluorophenyl)morpholino)-1,1,1-trifluoropropan-2-ol as an oil (340 mg), which was used as is in the next step. (M+H)$^+$=328 m/e.

Step g (S)-3-((R)-2-(4-chloro-3-fluorophenyl)morpholino)-1,1,1-trifluoropropan-2-ol (338 mg, 1.03 mmol) was combined with 1-chloro-2-fluoro-4-isocyanatobenzene (212 mg, 1.24 mmol) in 4 mL of dichloromethane. DIPEA (160 mg, 1.24 mmol) was added. The reaction tube was sealed and reaction mixture stirred at 60° C. for 5 h. TLC indicated complete consumption of the starting material. The mixture was evaporated and the residue was extracted with ether/hexanes (1:2 ratio) and water. The organic layer was washed with brine and water. Solvents were evaporated and the residue was purified by ISCO flash column chromatography (0% to 25% ethyl acetate in hexanes gradient). The desired fraction was concentrated and dissolved in ether/hexanes (1:2 ratio) and treated with 1N HCl in ether. Solvents were evaporated the residue was triturated with ether/hexanes (1:2 ratio) and the clear top layer solution was decanted. The resultant white solid residue was dried under heated vacuum to provide (4-chloro-3-fluoro-phenyl)-carbamic acid (S)-1-[(R)-2-(4-chloro-3-fluoro-phenyl)-morpholin-4-ylmethyl]-2,2,2-trifluoro-ethyl ester hydrochloride as a white solid (330 mg). $(M+H)^+=499$ m/e.

Example 5

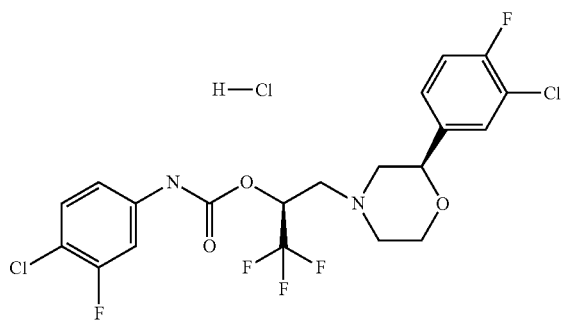 [SMILES: O=C(Nc1ccc(Cl)c(F)c1)O[C@@H](CN1CCO[C@H](c2ccc(F)c(Cl)c2)C1)C(F)(F)F ; Cl]

(4-Chloro-3-fluorophenyl)-carbamic acid (S)-1-[(R)-2-(3-chloro-4-fluorophenyl)-morpholin-4-ylmethyl]-2,2,2-trifluoroethyl ester hydrochloride Prepared by a similar procedure to Example 4 except substituting (R)-2-(3-chloro-4-fluorophenyl)-2-hydroxyethyl 4-methylbenzenesulfonate for (R)-2-(4-chloro-3-fluorophenyl)-2-hydroxyethyl 4-methylbenzenesulfonate afforded 131 mg of the title compound as an oil. $(M+H)^1=499, 501$ m/e.

Example 6

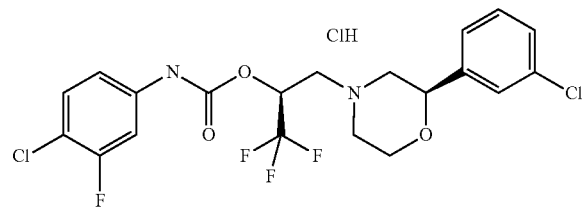 [SMILES: O=C(Nc1ccc(Cl)c(F)c1)O[C@@H](CN1CCO[C@H](c2cccc(Cl)c2)C1)C(F)(F)F ; Cl]

(4-Chloro-3-fluorophenyl)-carbamic acid (S)-1-[(R)-2-(3-chlorophenyl)-morpholin-4-ylmethyl]-2,2,2-trifluoroethyl ester hydrochloride (R)-2-(3-Chlorophenyl)-morpholine-4-carboxylic acid tert-butyl ester was prepared using a similar procedure as that described in Example 4 (steps b-d). (R)-2-(3-Chloro-phenyl)-morpholine-4-carboxylic acid tert-butyl ester (2.7 g, 9.07 mmol) was dissolved in HCl in dioxane (4M, 11.3 mL, 45.3 mmol) and the resulting mixture was heated at 55° C. for 2 h and then stirred at room temperature overnight. The solvent was removed by concentration in vacuo. The crude product was purified by reverse phase column chromatography (5-80% acetonitrile containing 0.1% TFA in water containing 0.1% TFA). The desired fractions were pooled and concentrated in vacuo. The product was dissolved in acetonitrile and water and 0.1 mL of concentrated HCl was added. The resultant solution was lyophilized to afford (R)-2-(3-chlorophenyl)-morpholine hydrochloride (0.71 g), as a white solid. $^1$H NMR (400 MHz, DEUTERIUM OXIDE) δ ppm 3.18 (dd, J=12.80, 11.54 Hz, 1H) 3.30 (dd, J=12.17, 3.89 Hz, 1H) 3.34-3.51 (m, 2H) 3.99 (ddd, J=13.11, 12.11, 2.64 Hz, 1H) 4.22 (dd, J=13.18, 3.64 Hz, 1H) 4.82 (dd, J=11.42, 2.38 Hz, 1H) 7.26-7.33 (m, 1H) 7.34-7.42 (m, 2H) 7.44 (d, J=1.76 Hz, 1H).

To a solution of (R)-2-(3-chloro-phenyl)-morpholine hydrochloride (45 mg, 192 μmol) and triethylamine (134 μL, 961 μmole) in 4 mL of acetonitrile was added (S)-2-(trifluoromethyl)oxirane (43.1 mg, 384 μmol). The mixture was stirred at 50° C. for 3 h, followed by evaporation in vacuo to afford (S)-3-((R)-2-(3-chlorophenyl)morpholino)-1,1,1-trifluoropropan-2-ol (59.5 mg), which was used directly for next step.

(S)-3-((R)-2-(3-chlorophenyl)morpholino)-1,1,1-trifluoropropan-2-ol (59.5 mg, 192 μmol), TEA (26.8 μL, 192 μmol) and 1-chloro-2-fluoro-4-isocyanatobenzene (32.9 mg, 192 μmol) were combined in 2 mL of acetonitrile and stirred at room temperature overnight. The solution was purified by reverse phase column chromatography (50-100% acetonitrile in water). The desired fractions were pooled, treated with 5 drops of conc. HCl and the solution lyophilized to afford (4-chloro-3-fluoro-phenyl)-carbamic acid (S)-1-[(R)-2-(3-chlorophenyl)-morpholin-4-ylmethyl]-2,2,2-trifluoro-ethyl ester hydrochloride (56 mg, 56%) as a white solid. $(M+H)^+=481$ m/e. $^1$H NMR (300 MHz, CHLOROFORM-d) δ ppm 2.81 (t, J=11.14 Hz, 1H) 3.00 (t, J=10.39 Hz, 1H) 3.16 (d, J=13.22 Hz, 1H) 3.44 (d, J=11.71 Hz, 1H) 3.56-3.79 (m, 2H) 4.20 (dd, J=13.22, 3.02 Hz, 1H) 4.36-4.59 (m, 1H) 5.55 (d, J=9.82 Hz, 1H) 5.70 (d, J=3.02 Hz, 1H) 7.17 (d, J=8.69 Hz, 1H) 7.29-7.44 (m, 5H) 7.50 (dd, J=10.77, 2.08 Hz, 1H) 8.82 (br. s., 1H).

Example 7

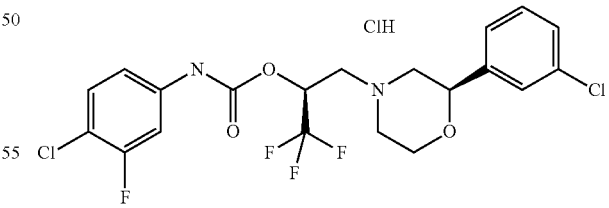

Alternative Synthesis of (4-Chloro-3-fluorophenyl)-carbamic acid (S)-1-[(R)-2-(3-chlorophenyl)-morpholin-4-ylmethyl]-2,2,2-trifluoroethyl ester hydrochloride In a 50 mL round-bottomed flask, 2-(3-chlorophenyl)morpholine hydrochloride (OChem., Lot #100301A1, 200 mg, 854 μmol) and DIEA (265 mg, 358 μl, 2.05 mmol) were combined with acetonitrile (2.5 ml) to give an off-white suspension. (S)-2-(trifluoromethyl)oxirane (287 mg, 2.56 mmol) was added. The reaction mixture was stirred at room temperature for 48 h. The reaction was complete by LCMS (MH+ =310). The reaction mixture was poured into 50 mL H₂O and extracted with diethyl ether/dichloromethane 10:1 (3×50 mL). The organic layers were combined, washed with saturated NaCl (1×50 mL), dried over MgSO₄ and concentrated in vacuo to afford 218 mg (82% yield) of (2S)-3-(2-(3-chlorophenyl)morpholino)-1,1,1-trifluoropropan-2-ol as an amber oil. (MH+=310).

In a 50 mL round-bottom flask, (2S)-3-(2-(3-chlorophenyl)morpholino)-1,1,1-trifluoropropan-2-ol (218 mg, 704 μmol) was combined with dichloromethane (12 ml) to give a colorless solution. triethylamine (71.2 mg, 98.1 μl, 704 μmol) was added. 1-chloro-2-fluoro-4-isocyanatobenzene (157 mg, 915 μmol) was added. The reaction mixture was heated to 50° C. and stirred for 3 h and filtered. The solid was washed with dichloromethane (2×). The combined filtrate and washes were concentrated to a reduced volume and loaded onto a silica column. The crude material was purified by flash chromatography (silica gel, 40 g, 0% to 20% EtOAc in hexanes gradient). The fractions that contained product were re-purified by flash chromatography (silica gel, 40 g, 10% to 20% (2:1 dichlormethane:EtOAc) in hexanes gradient). The front peak was collected and pooled and concentrated in vacuo. TLC corresponded to the free base of (4-chloro-3-fluorophenyl)-carbamic acid (S)-1-[(R)-2-(3-chlorophenyl)-morpholin-4-ylmethyl]-2,2,2-trifluoro-ethyl ester hydrochloride prepared in Example 6. The resulting colorless film was dissolved in 2:1 hexanes ether and treated with 1M HCl in ether (1 mL). The resulting sticky solid was concentrated in vacuo to afford the salt, which was foamed to a white solid with ether to give 107 mg of (4-chloro-3-fluoro-phenyl)-carbamic acid (S)-1-[(R)-2-(3-chlorophenyl)-morpholin-4-ylmethyl]-2,2,2-trifluoro-ethyl ester hydrochloride. LCMS: M+1=481;
¹H NMR (300 MHz, CHLOROFORM-d) δ ppm 2.83 (br. s., 1H) 3.03 (br. s., 1H) 3.16 (br. s., 1H) 3.48 (t, J=6.99 Hz, 1H) 3.68 (br. s., 2H) 4.21 (d, J=11.71 Hz, 1H) 4.52 (br. s., 1H) 5.61 (br. s., 1H) 5.71 (br. s., 1H) 7.17 (d, J=7.55 Hz, 1H) 7.29-7.45 (m, 5H) 7.50 (d, J=10.58 Hz, 1H) 8.83 (br. s., 1H).

Example 8

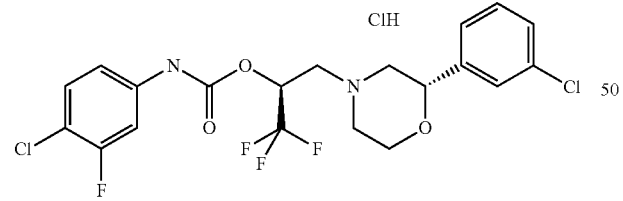

(4-Chloro-3-fluorophenyl)-carbamic acid (S)-1-[(S)-2-(3-chlorophenyl)-morpholin-4-ylmethyl]-2,2,2-trifluoroethyl ester hydrochloride In a 50 mL round-bottomed flask, 2-(3-chlorophenyl)morpholine hydrochloride (OChem., Lot #100301A1, 200 mg, 854 μmol) and DIEA (265 mg, 358 μl, 2.05 mmol) were combined with acetonitrile (2.5 ml) to give an off-white suspension. (S)-2-(trifluoromethyl)oxirane (287 mg, 2.56 mmol) was added. The reaction mixture was stirred at room temperature for 48 h. Reaction was complete by LCMS (MH+=310). The reaction mixture was poured into 50 mL H₂O and extracted with diethyl ether/dichloromethane 10:1 (3×50 mL). The organic layers were combined, washed with saturated NaCl (1×50 mL), dried over MgSO₄ and concentrated in vacuo to afford 218 mg (82% yield) of (2S)-3-(2-(3-chlorophenyl)morpholino)-1,1,1-trifluoropropan-2-ol as an amber oil. (MH+=310).

In a 50 mL round-bottom flask, (2S)-3-(2-(3-chlorophenyl)morpholino)-1,1,1-trifluoropropan-2-ol (218 mg, 704 μmol) was combined with dichloromethane (12 ml) to give a colorless solution. TEA (71.2 mg, 98.1 μl, 704 μmol) was added. 1-Chloro-2-fluoro-4-isocyanatobenzene (157 mg, 915 μmol) was added. The reaction mixture was heated to 50° C. and stirred for 3 h and filtered. The solid was washed with dichloromethane (2×). The combined filtrate and washes were concentrated to a reduced volume and loaded onto a silica column. The crude material was purified by flash chromatography (silica gel, 40 g, 0% to 20% EtOAc in hexanes). The fractions that contained product were re-purified by flash chromatography (silica gel, 40 g, 10% to 20% (2:1 dichlormethane:EtOAc) in hexanes). The fractions from the back peak were pooled and concentrated and the resulting colorless film was dissolved in 2:1 hexanes ether and treated with 1M HCl in ether (1 mL). The resulting sticky solid was concentrated in vacuo to afford the salt, which was foamed to a white solid with ether (120 mg). The foam was triturated with ether/hexanes to afford ca. 90% pure (4-chloro-3-fluorophenyl)-carbamic acid (S)-1-[(S)-2-(3-chlorophenyl)-morpholin-4-ylmethyl]-2,2,2-trifluoro-ethyl ester hydrochloride. LCMS: M+1=481;
¹H NMR (300 MHz, CHLOROFORM-d) δ ppm 2.38-3.62 (m, 6H) 4.14 (br. s., 1H) 4.72 (br. s., 1H) 5.21 (br. s., 1H) 5.61 (br. s., 1H) 6.97-7.16 (m, 2H) 7.21-7.35 (m, 5H) 7.43 (d, J=10.20 Hz, 1H).

Example 9

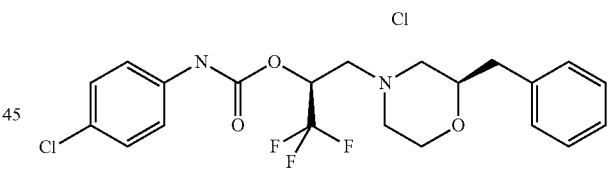

(4-Chlorophenyl)-carbamic acid (S)-1-((R)-2-benzyl-morpholin-4-ylmethyl)-2,2,2-trifluoroethyl ester hydrochloride In a 25 mL round-bottom flask was placed 2-benzylmorpholine (354 mg, 2 mmol), followed by (S)-2-(trifluoromethyl)oxirane (224 mg, 2 mmol). The mixture was stirred for 30 min. Another 100 uL of (S)-2-(trifluoromethyl)oxirane was added. Reaction mixture was continued at room temperature overnight, then concentrated in vacuo to afford (S)-3-(2-benzyl-morpholin-4-yl)-1,1,1-trifluoro-propan-2-ol a colorless oil (600 mg).

In a 150 mL round-bottomed flask, (S)-3-(2-benzyl-morpholin-4-yl)-1,1,1-trifluoro-propan-2-ol (595 mg, 2.06 mmol) was combined in acetonitrile (25 ml) to give a colorless solution. 1-chloro-4-isocyanatobenzene (316 mg, 2.06 mmol) was added. The resulting reaction mixture was warmed at 85° C. for 3 h. An additional 100 mg of 1-chloro- 4-isocyanatobenzene was added and the reaction mixture was warmed at 85° C. with stirring overnight.

Two major close-running spots of similar intensity could be seen by TLC (silica 20% EtOAc in hexanes eluent), a front-running spot and a later-running spot.

The crude reaction mixture was concentrated in vacuo, dissolved in dichloromethane and methanol and silica was added. The suspension was concentrated in vacuo. The resulting residue was dry-loaded onto a 40 g column. The crude material was purified by flash chromatography (silica gel, 10% ethyl acetate in hexanes) to afford the front-running peak, assigned as (4-chlorophenyl)-carbamic acid (S)-1-((R)-2-benzyl-morpholin-4-ylmethyl)-2,2,2-trifluoro-ethyl ester, as a white foam (300 mg, 26%). (M+H)$^+$=459 m/e. The resultant white foam was dissolved in ether and 0.5 mL of 1 M HCl in ether was added.

Hexane was added to the resulting suspension and the solid was washed with ether/hexanes and dried under vacuum to yield (4-chlorophenyl)-carbamic acid (S)-1-((R)-2-benzyl-morpholin-4-ylmethyl)-2,2,2-trifluoro-ethyl ester hydrochloride (127 mg, 13%) as an off-white solid. (M+H)$^+$=443 m/e.

Example 10

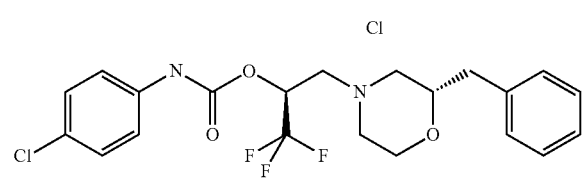 [SMILES: Cl ; O=C(Nc1ccc(Cl)cc1)O[C@@H](CN1CCO[C@@H](Cc2ccccc2)C1)C(F)(F)F]

(4-Chlorophenyl)-carbamic acid (S)-1-((S)-2-benzyl-morpholin-4-ylmethyl)-2,2,2-trifluoroethyl ester hydrochloride In a 25 mL round-bottom flask was placed 2-benzylmorpholine (354 mg, 2 mmol,), followed by (S)-2-(trifluoromethyl)oxirane (224 mg, 2.00 mmol). The mixture was stirred for 30 min. Another 100 uL of (S)-2-(trifluoromethyl)oxirane was added. Reaction mixture was continued at room temperature overnight, then concentrated in vacuo to afford (S)-3-(2-benzyl-morpholin-4-yl)-1,1,1-trifluoro-propan-2-ol a colorless oil (600 mg).

In a 150 mL round-bottomed flask, (S)-3-(2-benzyl-morpholin-4-yl)-1,1,1-trifluoro-propan-2-ol (595 mg, 2.06 mmol) was combined in acetonitrile (25 ml) to give a colorless solution. 1-chloro-4-isocyanatobenzene (316 mg, 2.06 mmol) was added. The resulting reaction mixture was warmed at 85° C. for 3 h. An additional 100 mg of 1-chloro-4-isocyanatobenzene was added and the reaction mixture was warmed at 85° C. with stirring overnight.

Two major close-running spots of similar intensity could be seen by TLC (silica 20% EtOAc in hexanes eluent), a front-running spot and a later-running spot.

The crude reaction mixture was concentrated in vacuo, dissolved in dichloromethane and methanol and silica was added. The suspension was concentrated in vacuo. The resulting residue was dry-loaded onto a 40 g column. Flash chromatography (90/10 hexanes/ethyl acetate) afforded the late-running spot, assigned as (4-chloro-phenyl)-carbamic acid (S)-1-((S)-2-benzyl-morpholin-4-ylmethyl)-2,2,2-trifluoro-ethyl ester, as a white foam. The resulting white foam was dissolved in ether and 0.5 mL of 1 M HCl in ether was added. Hexane was added to the resulting suspension and the solid was washed with ether/hexanes and dried under vacuum to yield (4-chloro-phenyl)-carbamic acid (S)-1-((S)-2-benzyl-morpholin-4-ylmethyl)-2,2,2-trifluoro-ethyl ester hydrochloride (242 mg, 24%) as an off-white solid. (M+H)$^+$=443 m/e.

Example 11

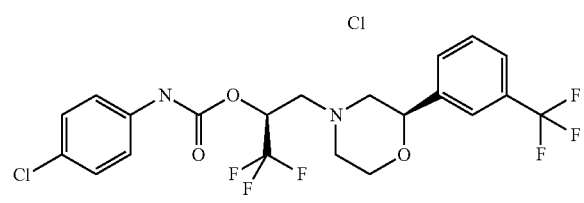 [SMILES: Cl ; O=C(Nc1ccc(Cl)cc1)O[C@@H](CN1CCO[C@H](c2cccc(C(F)(F)F)c2)C1)C(F)(F)F]

(4-Chlorophenyl)-carbamic acid (S)-2,2,2-trifluoro-1-[(R)-2-(3-trifluoromethylphenyl)-morpholin-4-ylmethyl]-ethyl ester hydrochloride Prepared by a similar procedure to Example 9 except substituting 2-(3-trifluoromethylphenyl)-morpholine for 2-benzylmorpholine afforded 62 mg of the title compound as a white solid. (M+H)$^+$=497 m/e.

Example 12

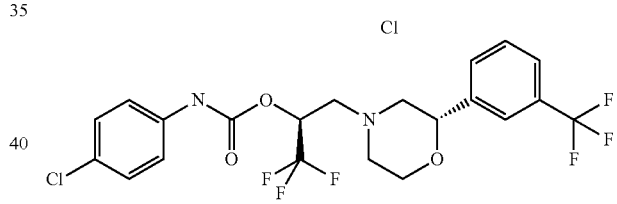

(4-Chlorophenyl)-carbamic acid (S)-2,2,2-trifluoro-1-[(S)-2-(3-trifluoromethylphenyl)-morpholin-4-ylmethyl]-ethyl ester hydrochloride Prepared by a similar procedure to Example 10 except substituting 2-(3-trifluoromethylphenyl)-morpholine for 2-benzylmorpholine afforded 55 mg of the title compound as a white solid. (M+H)$^+$=497 m/e.

Example 13

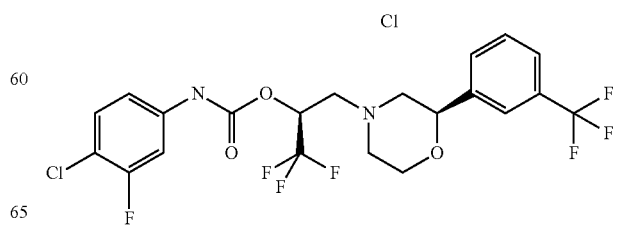

(4-Chloro-3-fluorophenyl)-carbamic acid (S)-2,2,2-trifluoro-1-[(R)-2-(3-trifluoromethylphenyl)-morpholin-4-ylmethyl]-ethyl ester hydrochloride In a 50 mL round-bottomed flask, 2-(3-(trifluoromethyl)phenyl)morpholine hydrochloride (515 mg, 1.92 mmol) and DIPEA (249 mg, 336 µl, 1.92 mmol) were combined with acetonitrile (10 ml) to give a white suspension. (S)-2-(trifluoromethyl)oxirane (323 mg, 2.89 mmol) was added. The reaction mixture was stirred at room temperature for 3 days and then was concentrated in vacuo. The reaction mixture was taken up in 100 mL dilute aqueous NaHCO₃ and extracted with dichloromethane (3×50 mL). The organic layers were dried over Na₂SO₄ and concentrated in vacuo to afford 528 mg (80%) of (2S)-1,1,1-trifluoro-3-(2-(3-(trifluoromethyl)phenyl)morpholino)propan-2-ol, which was used as is in the next step. (M+H)⁺=344 m/e.

In a 25 mL round-bottom flask, (2S)-1,1,1-trifluoro-3-(2-(3-(trifluoromethyl)phenyl)morpholino)-propan-2-ol (522 mg, 1.52 mmol) was combined with dichloromethane (12 ml) to give a colorless solution. TEA (154 mg, 212 µl, 1.52 mmol) was added. 1-chloro-2-fluoro-4-isocyanatobenzene (287 mg, 1.67 mmol) was added. The reaction mixture was warmed at 50° C. overnight. Reaction was complete as indicated by LCMS. Two major close-running spots of similar intensity could be seen by TLC (silica 15% EtOAc in hexanes eluent), a front-running spot and a later-running spot. The reaction mixture was concentrated in vacuo. The crude material was purified by flash chromatography (silica gel, 40 g, 0% to 15% EtOAc in hexanes gradient). Mixed fractions were re-purified by flash chromatography (silica gel, 40 g, 0% to 15% EtOAc in hexanes gradient).

Combined pure fractions from front peak were concentrated to give 311 mg of a colorless oil. The resultant oil was dissolved in 15 mL of ether. To that was added 2 mL of 1M HCl in ether. The mixture was stirred for a few min, then allowed to sit for 6 h with slow evaporation of ether to about 1-2 mL. A white solid that crystallized out was collected by filtration, washed twice with small volumes of ether and dried overnight on the vacuum pump to afford (4-chloro-3-fluorophenyl)-carbamic acid (S)-2,2,2-trifluoro-1-[(R)-2-(3-trifluoromethyl-phenyl)-morpholin-4-ylmethyl]-ethyl ester hydrochloride (260 mg) as a white crystalline solid. (M+H)⁺=515 m/e.

Example 14

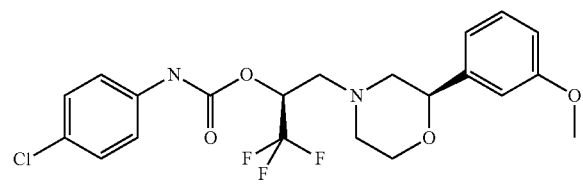 [SMILES: COc1cccc([C@@H]2CN(C[C@H](OC(=O)Nc3ccc(Cl)cc3)C(F)(F)F)CCO2)c1]

(4-Chlorophenyl)-carbamic acid (S)-2,2,2-trifluoro-1-[(R)-2-(3-methoxyphenyl)-morpholin-4-ylmethyl]-ethyl ester Step a In a 250 mL round-bottomed flask, 2-bromo-1-(3-methoxyphenyl)ethanone (3 g, 13.1 mmol) was combined in CHCl₃ (55.0 ml) and ethanol (11.0 ml) to give a colorless solution. The solution was cooled to 0° C. Benzylamine (5.61 g, 5.72 ml, 52.4 mmol) was added. After stirring for 0.5 h at 0° C. and then 2 h at room temperature, LCMS indicated that the reaction was mostly complete. (M+H)⁺=256 m/e. The reaction was cooled again to 0° C. and NaBH₄ (743 mg, 19.6 mmol) was added. The reaction was allowed to warm to room temperature and was stirred at this temperature for 2.5 h until reaction was complete. The reaction mixture was quenched with 1M HCl (25 mL) at 0° C. followed by stirring at room temperature for 1 h. The reaction mixture was poured into 150 mL 1 M NaOH and extracted with ethyl acetate (3×150 mL). Combined organic phase was washed with brine, dried over MgSO₄ and concentrated in vacuo. The crude material was purified by flash chromatography (silica gel, 80 g, 100% ethyl acetate) to yield 2-Benzylamino-1-(3-methoxy-phenyl)-ethanol (1.95 g, 58%). (M+H)⁺=258 m/e.

Step b

In a 250 mL round-bottomed flask, 2-(benzylamino)-1-(3-methoxyphenyl)ethanol (1.92 g, 7.46 mmol,) and TEA (831 mg, 1.14 ml, 8.21 mmol) were combined with dichloromethane (60 ml) to give a colorless solution. To this chloroacetyl chloride (927 mg, 657 µl, 8.21 mmol) in 10 mL dichloromethane was added dropwise at 0° C. After 1 h at 0° C. the reaction mixture was quenched with 1M aqueous HCl. The layers were separated, the aqueous layer extracted with dichloromethane. The combined organic layers were washed with 5% aqueous NaHCO₃, dried over Na₂SO₄ and concentrated in vacuo. The crude intermediate N-benzyl-2-chloro-N-[2-hydroxy-2-(3-methoxy-phenyl)-ethyl]-acetamide (2.61 g, 7.82 mmol) was combined with isopropanol (50 ml) to give a light yellow solution. KOH (526 mg, 9.38 mmol) was added and the resulting solution was stirred at room temperature overnight. The reaction mixture was concentrated in vacuo. The crude product was partitioned between ethyl acetate and 0.5M aqueous HCl. The layers were separated and the aqueous phase was extracted with ethyl acetate. The combined ethyl acetate extracts were washed with brine, dried over MgSO₄ and concentrated in vacuo to give 4-benzyl-6-(3-methoxyphenyl)-morpholin-3-one (2.3 g, 99%) which was directly used for next step without further purification. (M+H)⁺=298 m/e.

Step c

In a 500 mL round-bottomed flask, 4-benzyl-6-(3-methoxyphenyl)morpholin-3-one (2.3 g, 7.74 mmol) was combined with THF (75 ml) to give a light yellow solution. The reaction was cooled to 0° C. LiAlH₄ (9.67 ml of 2M solution in THF, 19.3 mmol) was added by dropwise addition. The resulting reaction mixture was allowed to warm to room temperature and then stirred at this temperature overnight. Reaction was complete as determined by LCMS. The crude reaction mixture was cooled to 0° C. and quenched carefully by sequential addition of H₂O (0.75 mL), 2M NaOH (1.5 mL) and then H₂O (1.5 mL). Additional THF was added during the addition of NaOH because mixture got too thick for stirring. The mixture was stirred for 1 h and filtered through Celite. The filtercake was washed several times with ethyl acetate. The combined filtrate and washes were concentrated in vacuo. The residue was purified by flash chromatography (silica gel, 80 g, 1.5% to 2% MeOH in dichloromethane) to yield 4-benzyl-2-(3-methoxy-phenyl)-morpholine (1.32 g, 60%) as an oil. (M+H)⁺=284 m/e. ¹H NMR (400 MHz, CHLOROFORM-d) δ ppm 2.14 (dd, J=11.37, 10.36 Hz, 1H) 2.31 (td, J=11.43, 3.41 Hz, 1H) 2.77 (dd, J=11.37, 1.77 Hz, 1H) 2.94 (dt, J=11.62, 2.02 Hz, 1H) 3.57 (s, 2H) 3.83 (s, 3H) 3.84-3.92 (m, 1H) 3.98-4.09 (m, 1H) 4.58 (dd, J=10.11, 2.27 Hz, 1H) 6.84 (ddd, J=8.21, 2.53, 1.14 Hz, 1H) 6.91-7.00 (m, 2H) 7.21-7.42 (m, 6H).

Step d

In a 250 mL round-bottomed flask, 4-benzyl-2-(3-methoxyphenyl)morpholine (2.3 g, 8.12 mmol) and palladium hydroxide on carbon (285 mg, 406 μmol) were combined in methanol (15 ml). The suspension was stirred at room temperature under a balloon of hydrogen overnight. The system was evacuated with argon 3 times. The reaction mixture was filtered through Celite, and the filtercake washed several times with methanol. The combined filtrate and washes were concentrated in vacuo to afford 2-(3-methoxy-phenyl)-morpholine (0.88 g, 56%) which was directly used for next step. $(M+H)^+=194$ m/e.

Step e

In a 25 mL round-bottom flask was placed 2-(3-methoxyphenyl)morpholine (0.88 g, 4.55 mmol), followed by (S)-2-(trifluoromethyl)oxirane (510 mg, 4.55 mmol). Some dichloromethane was added to wash down the side of the flask. Reaction progression was followed by LCMS. After 2 h an additional 150 uL of (S)-2-(trifluoromethyl)oxirane was added and the reaction mixture was stirred at room temperature overnight. Reaction did not go to completion. The crude material was purified by flash chromatography (silica gel, 40 g, 1% to 2% methanol in dichloromethane) to afford recovered starting 2-(3-methoxyphenyl)morpholine (320 mg, 36%) and (S)-1,1,1-trifluoro-3-[2-(3-methoxyphenyl)-morpholin-4-yl]-propan-2-ol (760 mg, 55%), which was directly used for next step. $(M+H)^+=306$ m/e.

Step f

In a 150 mL round-bottomed flask, (2S)-1,1,1-trifluoro-3-(2-(3-methoxyphenyl)morpholino)propan-2-ol (760 mg, 2.49 mmol) was combined in acetonitrile (25.0 ml) to give a colorless solution. 1-chloro-4-isocyanatobenzene (382 mg, 2.49 mmol) was added. The resulting reaction mixture was warmed at 85° C. for 2 h, cooled to room temperature and concentrated in vacuo. Two major close-running spots of similar intensity could be seen by TLC (silica 15% EtOAc in hexanes eluent), a front-running spot and a later-running spot. The crude material was purified by flash chromatography (silica gel, 160 g, 10% to 20% ethyl acetate in hexanes) to afford the front-running peak, assigned as (4-chloro-phenyl)-carbamic acid (S)-2,2,2-trifluoro-1-[(R)-2-(3-methoxy-phenyl)-morpholin-4-ylmethyl]-ethyl ester as a white foam (300 mg, 26%). $(M+H)^+=459$ m/e.

Example 15

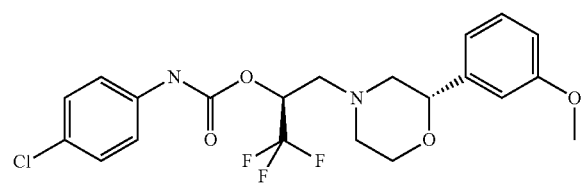 [SMILES: COc1cccc([C@H]2CN(C[C@H](OC(=O)Nc3ccc(Cl)cc3)C(F)(F)F)CCO2)c1]

(4-Chlorophenyl)-carbamic acid (S)-2,2,2-trifluoro-1-[(S)-2-(3-methoxyphenyl)-morpholin-4-ylmethyl]-ethyl ester (4-Chlorophenyl)-carbamic acid (S)-2,2,2-trifluoro-1-[(S)-2-(3-methoxyphenyl)-morpholin-4-ylmethyl]-ethyl ester was prepared according to the methods described for Example 14 except isolating the late-running peak from the flash chromatography as a white foam (207 mg, 18%). $(M+H)^+=459$ m/e.

Example 16

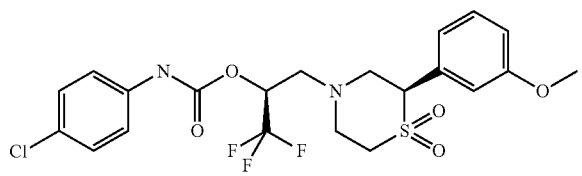 [SMILES: COc1cccc([C@@H]2CN(C[C@H](OC(=O)Nc3ccc(Cl)cc3)C(F)(F)F)CCS2(=O)=O)c1]

(4-Chlorophenyl)-carbamic acid (S)-2,2,2-trifluoro-1-[(R)-2-(3-methoxyphenyl)-1,1-dioxo-1$\lambda^6$-thiomorpholin-4-ylmethyl]ethyl ester Step a A mixture of 5 g (27.74 mmol) of methyl(3-methoxyphenyl)acetate, 5.2 g (29.14 mmol) of N-bromosuccinimide and a catalytic amount of AIBN in tetrachloromethane (50 ml) was heated under reflux with stirring for 2 h. The cooled reaction solution was filtered and washed with a small volume of dichloromethane. The combined filtrate and wash was concentrated in vacuo to afford methyl 2-bromo-2-(3-methoxyphenyl)acetate as an oil. Used as is in the next step.

$^1$H NMR (400 MHz, CHLOROFORM-d) δ ppm 3.81 (s, 3H) 3.85 (s, 3H) 5.36 (s, 1H) 6.91 (ddd, J=8.27, 2.34, 1.26 Hz, 1H) 7.10-7.15 (m, 2H) 7.27-7.32 (m, 1H).

Step b

In a 500 mL round-bottomed flask, methyl 2-bromo-2-(3-methoxyphenyl)acetate (5.2 g, 20.1 mmol), 2-aminoethanethiol (1.55 g, 20.1 mmol) and potassium carbonate (5.55 g, 40.1 mmol) were combined with ethanol (150 ml) to give a light yellow suspension. The resultant mixture was stirred at 85° C. (bath temp.) for 2.5 h. No starting material remained. The intermediate, [2-amino-1-(3-methoxy-phenyl)-ethylsulfanyl]-acetic acid methyl ester, was the major product with 25% of the cyclized product. The mixture was further heated at reflux for an additional 4.5 h. Complete by LCMS. Reaction mixture was allowed to cool to room temperature and sit overnight. The reaction mixture was poured into 500 mL H$_2$O and extracted with EtOAc (3×300 mL). The combined organic layers were washed with brine, dried over MgSO$_4$ and concentrated in vacuo. The resulting pale yellow solid was triturated with cold ether and dried under vacuum to afford 2-(3-methoxyphenyl)thiomorpholin-3-one (3.7 g, 83%) as a yellow solid. $(M+H)^+=224$ m/e. $^1$H NMR (400 MHz, CHLOROFORM-d) δ ppm 2.88 (td, J=5.81, 2.78 Hz, 2H) 3.67 (td, J=5.81, 3.54 Hz, 2H) 3.82 (s, 3H) 4.63 (s, 1H) 6.42 (br. s., 1H) 6.85 (ddd, J=8.34, 2.53, 0.76 Hz, 1H) 7.00 (t, J=2.15 Hz, 1H) 7.01-7.05 (m, 1H) 7.29 (t, J=7.93, 1H).

Step c

In a 500 mL round-bottomed flask, 2-(3-methoxyphenyl)thiomorpholin-3-one (3.7 g, 16.6 mmol) and sodium borohydride (627 mg, 16.6 mmol) were combined with dioxane (75 ml). The reaction mixture was cooled to 0° C. To that was added dropwise acetic acid (995 mg, 949 μl, 16.6 mmol) in 20 mL dry dioxane. The resultant mixture was warmed at reflux overnight and then allowed to cool to room temperature. The crude reaction mixture was diluted with water and 10% NaHCO$_3$ and extracted 3 times into EtOAc. The combined organic layer was washed with water, then washed with brine, dried over Na$_2$SO$_4$ and concentrated in vacuo.

The resultant crude intermediate was taken up in 25 mL methanol and 25 mL of 10% aqueous HCl was added. The mixture was stirred at room temperature overnight. The mixture was neutralized with NaHCO$_3$ and extracted with dichloromethane (3×). The combined organic layer was washed with water, dried over Na$_2$SO$_4$ and concentrated in vacuo. The crude product, 2-(3-methoxyphenyl)thiomorpholine, was used as is in the next step. (M+H)$^+$=210 m/e.

Step d

The crude 2-(3-methoxyphenyl)thiomorpholine was taken up in 75 mL acetonitrile and treated with di-tert-butyl dicarbonate (952 mg, 4.36 mmol). The reaction mixture was stirred at room temperature for 36 h. The reaction stopped and did not go to completion. The reaction mixture was concentrated in vacuo. The crude material was purified by flash chromatography (silica gel, 80 g, 0% to 5% MeOH in dichloromethane) to afford 420 mg of recovered starting 2-(3-methoxyphenyl)thiomorpholine and 425 mg of the desired product, tert-butyl 2-(3-methoxyphenyl)thiomorpholine-4-carboxylate, which was used as is for the next step.

Step e

In a 250 mL round-bottomed flask, tert-butyl 2-(3-methoxyphenyl)thiomorpholine-4-carboxylate (415 mg, 1.34 mmol) was combined with dichloromethane (20 ml) to give a light yellow solution. m-chloroperbenzoic acid (601 mg, 2.68 mmol) in 4 mL dichloromethane was added dropwise. The reaction mixture was stirred at room temperature for 1.5 h, poured onto 5% NaOH and extracted 3 times with dichloromethane. The combined organic extracts were dried over Na$_2$SO$_4$ and concentrated in vacuo. The crude material was purified by flash chromatography (silica gel, 40 g, 1% to 2% MeOH in dichloromethane) to afford 2-(3-methoxyphenyl)-1,1-dioxo-1λ$^6$-thiomorpholine-4-carboxylic acid tert-butyl ester (441 mg) as a pale yellow foam. $^1$H NMR (400 MHz, CHLOROFORM-d) δ ppm 1.49 (s, 9H) 3.14 (d, J=3.28 Hz, 2H) 3.43-3.78 (m, 2H) 3.83 (s, 3H) 4.04 (br. s., 1H) 4.57 (br. s., 2H) 6.92-7.05 (m, 3H) 7.29-7.39 (m, 1H).

Step f

In a 150 mL round-bottomed flask, 2-(3-methoxyphenyl)-1,1-dioxo-1λ$^6$-thiomorpholine-4-carboxylic acid tert-butyl ester (435 mg, 1.27 mmol) was combined with dichloromethane (15 ml) to give a light yellow solution. To that was added 4 mL TFA. The resultant reaction mixture was stirred at room temperature for 1 h. Reaction was complete by LCMS. Reaction mixture was concentrated in vacuo. The residue was dissolved in dichloromethane, poured onto 10% NaHCO$_3$ and extracted 3 times with dichloromethane. Combined organic layers were washed with water, dried over Na$_2$SO$_4$, filtered and filtrate concentrated in vacuo to afford 2-(3-methoxyphenyl)-thiomorpholine 1,1-dioxide (252 mg) which was used as is in the next step. (M+H)$^+$=242 m/e.

Step g

In a 25 mL round-bottomed flask was placed 2-(3-methoxyphenyl)-thiomorpholine-1,1-dioxide (252 mg, 1.04 mmol), followed by (S)-2-(trifluoromethyl)oxirane (129 mg, 1.15 mmol). The reaction mixture was stirred overnight. Reaction was not complete. An additional 100 mg of the (S)-2-(trifluoromethyl)oxirane was added followed by a small amount of dichloromethane. Reaction mixture was stirred at room temperature for an additional 2 h. The crude material was purified by flash chromatography (silica gel, 40 g, 10% to 40% EtOAc in hexanes) afforded (S)-1,1,1-trifluoro-3-[2-(3-methoxyphenyl)-1,1-dioxo-1λ$^6$-thiomorpholin-4-yl]-propan-2-ol (240 mg) as a white foam. (M+H)$^+$=354 m/e.

Step h

In a 25 mL round-bottom flask, (S)-1,1,1-trifluoro-3-[2-(3-methoxyphenyl)-1,1-dioxo-1λ$^6$-thiomorpholin-4-yl]-propan-2-ol (234 mg, 662 µmol) was combined with acetonitrile (5.00 ml) to give a colorless solution. 1-chloro-4-isocyanatobenzene (102 mg, 662 µmol) was added. The reaction mixture was warmed at 85° C. for 3 h, resulting in only a trace of product. Heating was continued at reflux overnight. The reaction was 50% complete by LCMS. An additional 60 mg of 1-chloro-4-isocyanatobenzene was added and the reaction mixture was heated at reflux for overnight. Reaction was not complete. Another 50 mg starting 1-chloro-4-isocyanatobenzene was added and the reaction mixture was stirred at reflux for 10 h. Reaction was complete by LCMS. The reaction mixture was concentrated in vacuo. The crude material was purified by flash chromatography (silica gel, 40 g, 5% to 30% EtOAc in hexanes gradient). The front end fractions of the product peak that was isolated from the column, that contained mostly one pure epimer (as determined by LCMS) were pooled to afford (4-chlorophenyl)-carbamic acid (S)-2,2,2-trifluoro-1-[(R)-2-(3-methoxyphenyl)-1,1-dioxo-1λ$^6$-thiomorpholin-4-ylmethyl]-ethyl ester (46 mg) as a white foam. The absolute configuration was assigned based on analogy to Examples 1, 2, 11 and 12. (M+H)$^+$=507 m/e.

Example 17

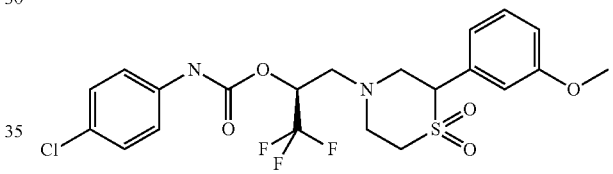

(4-Chlorophenyl)-carbamic acid (S)-2,2,2-trifluoro-1-[2-(3-methoxyphenyl)-1,1-dioxo-1λ$^6$-thiomorpholin-4-ylmethyl]-ethyl ester (4-Chlorophenyl)-carbamic acid (S)-2,2,2-trifluoro-1-[2-(3-methoxyphenyl)-1,1-dioxo-1λ$^6$-thiomorpholin-4-ylmethyl]-ethyl ester was prepared according to the methods described for Example 16 except pooling all the fractions from the product peak except the first few fractions from the flash chromatography to afford (4-chlorophenyl)-carbamic acid (S)-2,2,2-trifluoro-1-[2-(3-methoxyphenyl)-1,1-dioxo-1λ$^6$-thiomorpholin-4-ylmethyl]-ethyl ester (188 mg) as a white foam. Product was two peaks by LCMS in a 32:62 ratio, each with (M+H)$^+$=507 m/e.

Example 18

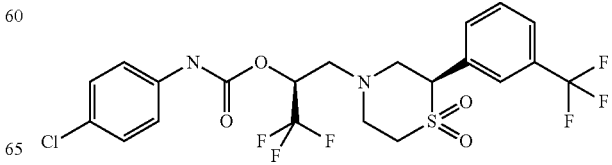

(4-Chlorophenyl)-carbamic acid (S)-1-[(R)-1,1-dioxo-2-(3-trifluoromethylphenyl)-1λ⁶-thiomorpholin-4-ylmethyl]-2,2,2-trifluoroethyl ester (S)-3-[1,1-Dioxo-2-(3-trifluoromethylphenyl)-1λ⁶-thiomorpholin-4-yl]-1,1,1-trifluoro-propan-2-ol was prepared according to the methods described in Example 16 (steps a-g) except substituting methyl(3-trifluoromethylphenyl)acetate for methyl(3-methoxyphenyl)acetate.

In a 25 mL round-bottom flask, (S)-3-[1,1-dioxo-2-(3-trifluoromethylphenyl)-1λ⁶-thiomorpholin-4-yl]-1,1,1-trifluoro-propan-2-ol (600 mg, 1.53 mmol) was combined with dichloromethane (10 ml) to give a colorless solution. triethylamine (214 µL, 1.53 mmol) was added. 1-chloro-4-isocyanatobenzene (235 mg, 1.53 mmol) was added. The reaction mixture was warmed at 50° C. overnight. The solvent was evaporated. Two major close-running spots of similar intensity could be seen by TLC (silica 25% EtOAc in hexanes eluent), a front-running spot and a later-running spot. The crude residue was purified by flash chromatography (silica gel, 24 g, 5% to 20% EtOAc in hexanes gradient) to afford the front-running peak, assigned as (4-chlorophenyl)-carbamic acid (S)-1-[(R)-1,1-dioxo-2-(3-trifluoromethylphenyl)-1λ⁶-thiomorpholin-4-ylmethyl]-2,2,2-trifluoroethyl ester as a white foam (93 mg). (M+H)⁺=545 m/e.

Example 19

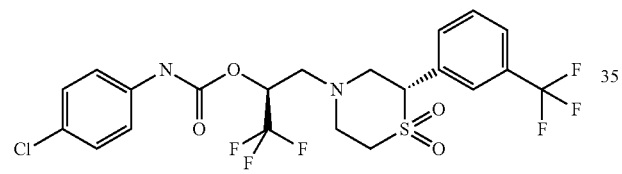

(4-Chlorophenyl)-carbamic acid (S)-1-[(S)-1,1-dioxo-2-(3-trifluoromethylphenyl)-1λ⁶-thiomorpholin-4-ylmethyl]-2,2,2-trifluoroethyl ester (4-Chlorophenyl)-carbamic acid (S)-1-[(S)-1,1-dioxo-2-(3-trifluoromethylphenyl)-1λ⁶-thiomorpholin-4-ylmethyl]-2,2,2-trifluoroethyl ester was prepared according to the methods described for Example 18 except isolating product enriched in the late-running peak from the flash chromatography as a white foam (180 mg, containing 86% of the titled epimer). (M+H)⁺=545 m/e.

Example 20

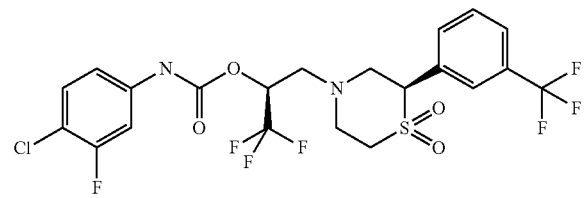 [SMILES: O=C(Nc1ccc(Cl)c(F)c1)O[C@@H](CN1CCS(=O)(=O)[C@H](c2cccc(C(F)(F)F)c2)C1)C(F)(F)F]

(4-Chloro-3-fluorophenyl)-carbamic acid (S)-1-[(R)-1,1-dioxo-2-(3-trifluoromethylphenyl)-1λ⁶-thiomorpholin-4-ylmethyl]-2,2,2-trifluoroethyl ester Prepared by a similar procedure to Example 18 except substituting 1-chloro-2-fluoro-4-isocyanatobenzene for 1-chloro-4-isocyanatobenzene (step h) afforded 109 mg of the title compound as a white foam. (M+H)⁺=563 m/e.

Example 21

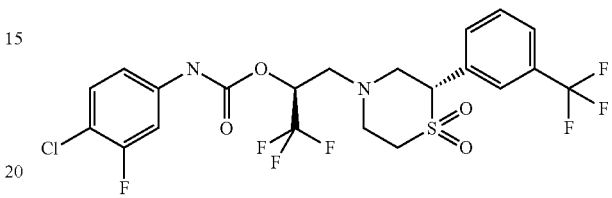

(4-Chloro-3-fluorophenyl)-carbamic acid (S)-1-[(S)-1,1-dioxo-2-(3-trifluoromethylphenyl)-1λ⁶-thiomorpholin-4-ylmethyl]-2,2,2-trifluoroethyl ester (4-Chloro-3-fluorophenyl)-carbamic acid (S)-1-[(S)-1,1-dioxo-2-(3-trifluoromethylphenyl)-1λ⁶-thiomorpholin-4-ylmethyl]-2,2,2-trifluoroethyl ester was prepared according to the methods described for Example 20 except isolating the late-running peak from the flash chromatography as a white foam (117 mg). (M+H)⁺=563 m/e.

Example 22

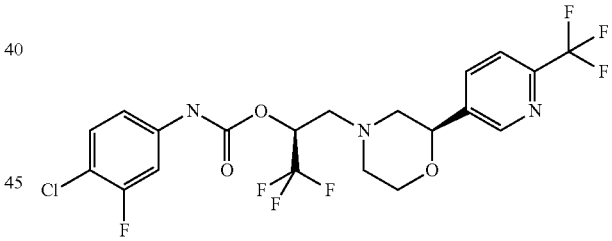

(4-Chloro-3-fluorophenyl)-carbamic acid (S)-2,2,2-trifluoro-1-[(R)-2-(6-trifluoromethyl-pyridin-3-yl)-morpholin-4-ylmethyl]-ethyl ester Step a In a 100 mL round-bottomed flask, 6-(trifluoromethyl)nicotinaldehyde (2.61 g, 14.9 mmol) was combined with nitromethane (20 ml) to give a light yellow solution. triethylamine (1.51 g, 2.08 ml, 14.9 mmol) was added. The reaction mixture was stirred at room temperature for 1.5 h and concentrated in vacuo. The resultant residue was purified by flash chromatography (silica gel, 80 g, 0.2% to 1.2% MeOH in dichloromethane gradient) to afford 2-nitro-1-(6-(trifluoromethyl)pyridin-3-yl)ethanol (2.4 g) as an off-white solid.

In a 250 mL round-bottomed flask, 2-nitro-1-(6-(trifluoromethyl)pyridin-3-yl)ethanol (2.4 g, 10.2 mmol) was combined with THF (40 ml) and methanol (40.0 ml) to give a colorless solution and placed under N₂ atmosphere. 360 mg of 10% Pd/C was added. Ammonium formate (3.2 g, 50.8 mmol) was added. The reaction mixture was stirred at room temperature overnight. Complete by LCMS. The reaction mixture was purged with $N_2$ and then filtered through Celite. The Celite filtercake was washed several times with methanol. The combined washes and filtrate was concentrated in vacuo. The residue was taken up in dichloromethane/0.01% NaOH and extracted 5 times with dichloromethane. The organic layers were dried over $Na_2SO_4$ and concentrated in vacuo. Product was still present in the aqueous phase so saturated NaCl was added to the aqueous phase and the aqueous phase was extracted 3 times with dichloromethane. The organic layers were dried over $Na_2SO_4$ and concentrated in vacuo. The combine product as a pale yellow solid was triturated with ether to get an off-white powder which was washed twice with ether/hexanes to afford 2-amino-1-(6-(trifluoromethyl)pyridin-3-yl)ethanol (1.05 g). $(M+H)^+=207$ m/e. $^1H$ NMR (300 MHz, CHLOROFORM-d) δ ppm 2.76 (dd, J=12.84, 7.93 Hz, 1H) 3.15 (dd, J=12.84, 3.78 Hz, 1H) 4.75 (dd, J=8.12, 3.97 Hz, 1H) 7.69 (d, J=8.31 Hz, 1H) 7.93 (dd, J=8.12, 1.70 Hz, 1H) 8.71 (d, J=1.51 Hz, 1H).

Step b 2-amino-1-(6-(trifluoromethyl)pyridin-3-yl)ethanol (1.05 g, 5.09 mmol) and triethylamine (567 mg, 781 μl, 5.6 mmol) were combined with dichloromethane (50 ml) to give a yellow solution. To this chloroacetyl chloride (633 mg, 449 μl, 5.6 mmol) in 20 mL dichloromethane was added by dropwise addition at 0° C. After 1 h at 0° C. the reaction mixture was complete by LCMS. The reaction mixture was poured onto water. The pH adjusted to 8 with saturated $NaHCO_3$. The resultant aqueous phase was extracted 4 times with dichloromethane. The combined organic extracts were washed with brine. Brine and aqueous phase were combined and further extracted with dichloromethane (2×). The combined organic layers were dried over $Na_2SO_4$ and concentrated in vacuo. The resulting residue, 2-chloro-N-(2-hydroxy-2-(6-(trifluoromethyl)pyridin-3-yl)ethyl)acetamide (1.5 g, 5.31 mmol) was combined with methanol (100 ml) to give a light yellow solution. KOH (357 mg, 6.37 mmol) was added. Reaction was checked by LCMS after and showed only starting material. A solvent exchange was done with isopropanol as follows: 50 mL of isopropanol was added to the reaction mixture and it was concentrated to ¼ volume under reduced pressure at 40° C. Another 50 mL of isopropanol was added and the mixture was concentrated under reduced pressure to 50 mL. Another 50 mL of isopropanol was added. LCMS showed a ratio of 81:19 starting material:product. The reaction mixture was stirred at room temperature overnight. LCMS showed a ratio of 15:52 starting material: product. Warming at 50° C. for 1 h did not lead to any more product formation, so reaction was stopped. The reaction mixture was concentrated to reduced volume (5 mL). The resultant solution was diluted with ethyl acetate and water and the aqueous phase adjusted to pH=6 (with 1N HCl). The layers were separated and the aqueous phase was extracted with ethyl acetate (2×). The aqueous phase was made basic with NaOH and extracted again with ethyl acetate (2×). The combined ethyl acetate extracts were washed with brine and dried over $MgSO_4$, and concentrated in vacuo. The crude residue was purified by flash chromatography (silica gel, 40 g, 0% to 2% MeOH in dichloromethane) to afford a white solid, which was triturated with ether to afford 6-(6-(trifluoromethyl)pyridin-3-yl)morpholin-3-one as an off-white powder (659 mg). $^1H$ NMR (300 MHz, CHLOROFORM-d) δ ppm 3.45-3.69 (m, 2H) 4.25-4.61 (m, 2H) 4.93 (dd, J=10.01, 3.59 Hz, 1H) 6.62 (br. s., 1H) 7.74 (d, J=8.31 Hz, 1H) 7.96 (dd, J=8.31, 1.89 Hz, 1H) 8.75 (d, J=1.89 Hz, 1H).

Step c

In a 500 mL round-bottomed flask, 6-(6-(trifluoromethyl)pyridin-3-yl)morpholin-3-one (0.65 g, 2.64 mmol) was combined with THF (35 ml) to give a light yellow solution. The reaction mixture was cooled to 0° C. $LiAlH_4$ (3.3 ml of a 2M solution in THF, 6.6 mmol) was added by dropwise addition. The reaction mixture was allowed to warm to room temperature and then stirred for 12 h. The reaction mixture was cooled to 0° C. and quenched carefully by sequential addition of $H_2O$ (0.27 mL), 2M NaOH (0.54 mL) and then $H_2O$ (0.54 mL). The mixture was stirred for 10 min., filtered through Celite and the Celite washed 1 time with THF and several times with ethyl acetate. The combined filtrate and washes were concentrated. The crude residue was purified by flash chromatography (silica gel, 40 g, 0.5% to 5% MeOH in dichloromethane) to afford 2-(6-(trifluoromethyl)pyridin-3-yl)morpholine (272 mg) as a colorless oil. $^1H$ NMR (400 MHz, CHLOROFORM-d) δ ppm 1.92 (br. s., 1H) 2.76 (dd, J=12.38, 10.36 Hz, 1H) 2.88-3.07 (m, 2H) 3.13 (dd, J=12.25, 2.65 Hz, 1H) 3.81 (td, J=11.37, 2.78 Hz, 1H) 4.01-4.15 (m, 1H) 4.63 (dd, J=10.36, 2.53 Hz, 1H) 7.69 (d, J=8.08 Hz, 1H) 7.84-7.96 (m, 1H) 8.63-8.77 (m, 1H).

Step d

In a 50 mL round-bottomed flask, 2-(6-(trifluoromethyl)pyridin-3-yl)morpholine (266 mg, 1.15 mmol) and (S)-2-(trifluoromethyl)oxirane (154 mg, 1.37 mmol) were combined with acetonitrile (2 ml). The reaction mixture was stirred at room temperature overnight and concentrated in vacuo. The crude product, (S)-1,1,1-trifluoro-3-[(R)-2-(6-trifluoromethyl-pyridin-3-yl)-morpholin-4-yl]-propan-2-ol (384 mg, 97%), was used as is in next reaction. $(M+H)^+=345$ m/e.

Step e

In a 25 mL round-bottom flask, (2S)-1,1,1-trifluoro-3-(2-(6-(trifluoromethyl)pyridin-3-yl)morpholino)propan-2-ol (384 mg, 1.12 mmol) was combined with dichloromethane (12 ml) to give a colorless solution. Triethylamine (113 mg, 155 μl, 1.12 mmol) was added. 1-chloro-2-fluoro-4-isocyanatobenzene (211 mg, 1.23 mmol) was added. The reaction mixture was warmed at 50° C. overnight. Reaction was complete by LCMS. Two major close-running spots of similar intensity could be seen by TLC (silica 25% EtOAc in hexanes eluent), a front-running spot and a later-running spot. The crude material was purified by flash chromatography (silica gel, 80 g, 5% to 20% EtOAc in hexanes gradient). Mixed fractions were purified by flash chromatography (silica gel, 80 g, 5% to 20% EtOAc in hexanes gradient). Fractions from both columns that contained pure front-running product were concentrated, dissolved in ether and treated with 1M HCl in ether to form the HCl salt. The salt came out as a sticky semisolid, which turned yellow. The resulting residue was taken up in dichloromethane and free-based by washing with saturated $NaHCO_3$. The aqueous phase was extracted 3 times with dichloromethane. The combined organic layers were dried over $Na_2SO_4$ and concentrated in vacuo. The crude material was purified by flash chromatography (silica gel, 40 g, 20% to 30% EtOAc in hexanes gradient) to afford (4-chloro-3-fluorophenyl)-carbamic acid (S)-2,2,2-trifluoro-1-[(R)-2-(6-trifluoromethyl-pyridin-3-yl)-morpholin-4-ylmethyl]-ethyl ester (146 mg) as a white foam. $(M+H)^+=516$ m/e.

Example 23

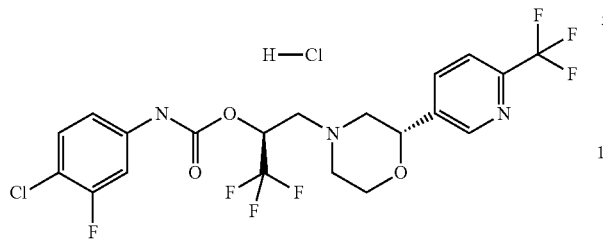

(4-Chloro-3-fluorophenyl)-carbamic acid (S)-2,2,2-trifluoro-1-[(S)-2-(6-trifluoromethyl-pyridin-3-yl)-morpholin-4-ylmethyl]-ethyl ester hydrochloride In a 25 mL round-bottom flask, (2S)-1,1,1-trifluoro-3-(2-(6-(trifluoromethyl)pyridin-3-yl)morpholino)propan-2-ol (384 mg, 1.12 mmol) was combined with dichloromethane (12 ml) to give a colorless solution. TEA (113 mg, 155 µl, 1.12 mmol) was added. 1-chloro-2-fluoro-4-isocyanatobenzene (211 mg, 1.23 mmol) was added. The reaction mixture was warmed at 50° C. overnight. Reaction was complete by LCMS. Two major close-running spots of similar intensity could be seen by TLC (silica 25% EtOAc in hexanes eluent), a front-running spot and a later-running spot. The crude material was purified by flash chromatography (silica gel, 80 g, 5% to 20% EtOAc in hexanes). Mixed fractions were purified by flash chromatography (silica gel, 80 g, 5% to 20% EtOAc in hexanes). Fractions from both columns that contained pure later-running product were concentrated, dissolved in ether and treated with 1M HCl in ether to form the HCl salt. The resultant salt formed a gummy solid, which was scraped on the sides of the flask to form an off-white solid. This solid was filtered and washed with ether. A portion of the product was lost during the transfer. The resultant solid was placed on the pump to afford (4-chloro-3-fluorophenyl)-carbamic acid (S)-2,2,2-trifluoro-1-[(S)-2-(6-trifluoromethyl-pyridin-3-yl)-morpholin-4-ylmethyl]-ethyl ester hydrochloride (60 mg) as an off-white solid. $(M+H)^+$=516 m/e.

Example 24

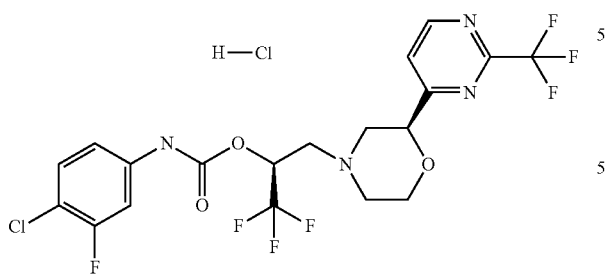

(4-Chloro-3-fluorophenyl)-carbamic acid (S)-2,2,2-trifluoro-1-[(S)-2-(2-trifluoromethylpyrimidin-4-yl)-morpholin-4-ylmethyl]-ethyl ester hydrochloride Prepared by a similar procedure to Example 4 except substituting 1-(2-(trifluoromethyl)pyrimidin-4-yl)ethanone for 1-(3-chloro-4-fluorophenyl)ethanone afforded 164 mg of the title compound as an off-white solid. $(M+H)^+$=517 m/e.

Example 25

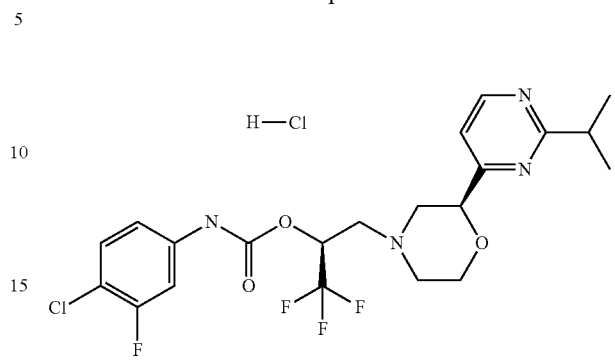

(4-Chloro-3-fluorophenyl)-carbamic acid (S)-2,2,2-trifluoro-1-[(S)-2-(2-isopropylpyrimidin-4-yl)-morpholin-4-ylmethyl]-ethyl ester hydrochloride Step a In a 100 mL round-bottomed flask, 2-isopropylpyrimidine-4-carbaldehyde (865 mg, 5.76 mmol) was combined with nitromethane (7.00 ml) to give a colorless solution. TEA (583 mg, 803 µl, 5.76 mmol) was added. The reaction mixture was stirred at room temperature for 1 h. Complete by LCMS. The reaction mixture was concentrated in vacuo, kept on the vacuum pump for 30 min. and used as is immediately. The resulting yellow oil was taken up in 20 mL of THF and 20 mL of methanol and placed under a nitrogen atmosphere. To that was added 240 mg of 10% Pd/C (pre-wet with ethanol). Ammonium formate (1.82 g, 28.8 mmol) was added. The reaction mixture was stirred at room temperature for 2 days. Complete by LCMS. The reaction mixture was purged with argon, filtered through Celite and the filtercake washed several times with methanol. The combined filtrate and washes were concentrated in vacuo and loaded onto column in dichloromethane/methanol approx. 95:5. The crude material was purified by flash chromatography (silica gel, 40 g, 10% to 50% [(60:10:1 dichloromethane:MeOH:NH$_4$OH) in dichloromethane gradient] to afford 2-amino-1-(2-isopropylpyrimidin-4-yl)ethanol (0.54 g) as a white solid. $(M+H)^+$=182 m/e.

Step b

In a 250 mL round-bottomed flask, 2-amino-1-(2-isopropylpyrimidin-4-yl)ethanol (504 mg, 2.78 mmol) and TEA (466 µl, 3.34 mmol) were combined with THF (20 ml) to give a colorless solution. The reaction mixture was cooled in an ice bath. 2-Bromoethanol (207 µl, 2.92 mmol) in 5 mL THF was added dropwise. The reaction was allowed to warm to room temperature and stirred at that temperature for 23 days monitoring by LCMS. Reaction had progressed to 50% completion. Reaction mixture was filtered, washed with THF (2×10 mL), washed with EtOAc and the combined filtrate and washes concentrated in vacuo. The crude mixture, which contained 60% 2-(2-hydroxy-ethylamino)-1-(2-isopropylpyrimidin-4-yl)-ethanol and 40% starting 2-amino-1-(2-isopropylpyrimidin-4-yl)ethanol by NMR, was used as is in the next step.

The crude mixture from above which contained about 60% of 2-(2-hydroxyethylamino)-1-(2-isopropylpyrimidin-4-yl) ethanol (1.08 g, 2.88 mmol, Eq: 1.00) and 40% starting 2-amino-1-(2-isopropylpyrimidin-4-yl)ethanol was dissolved in 50 mL of dichloromethane. To this stirred solution was added di-tert-butyl dicarbonate (628 mg, 2.88 mmol, Eq: 1.00). The solution was stirred at room temperature overnight. Solvents were evaporated and the residue was purified by Analogix flash column chromatography (0% to 60% ethyl acetate in hexanes gradient) to afford (2-hydroxyethyl)-[2-hydroxy-2-(2-isopropyl-pyrimidin-4-yl)-ethyl]-carbamic acid tert-butyl ester (396 mg). (M+H)$^+$=326 m/e. $^1$H NMR (300 MHz, CHLOROFORM-d) δ ppm 1.30-1.56 (m, 16H) 3.08-4.01 (m, 8H) 4.87-5.12 (m, 1H) 7.16-7.40 (m, 2H) 8.68 (br. s., 1H).

Step c (2-Hydroxyethyl)-[2-hydroxy-2-(2-isopropyl-pyrimidin-4-yl)-ethyl]-carbamic acid tert-butyl ester (396 mg, 1.22 mmol) was dissolved in methyl-t-butylether (MTBE) (15 ml). Triphenylphosphine (383 mg, 1.46 mmol) was added. To this mixture was added diisopropyl azodicarboxylate (295 mg, 288 µl, 1.46 mmol) dropwise. The solution was stirred at room temperature overnight. A white solid was filtered off, washed with MTBE (2×10 mL). The combined filtrate and washes were concentrated and the resulting residue was purified by Analogix flash column chromatography (40 g silica gel, 0% to 20% ethyl acetate in hexanes gradient) to afford 2-(2-isopropyl-pyrimidin-4-yl)-morpholine-4-carboxylic acid tert-butyl ester (256 mg) as a white solid. (M+H)$^l$=308 m/e. $^1$H NMR (400 MHz, CHLOROFORM-d) δ ppm 1.35 (d, J=6.82 Hz, 6H) 1.52 (s, 9H) 2.80 (br. s., 1H) 3.06 (d, J=10.61 Hz, 1H) 3.22 (dt, J=13.71, 6.92 Hz, 1H) 3.72 (td, J=11.62, 2.53 Hz, 1H) 3.98 (br. s., 1H) 4.07 (d, J=9.60 Hz, 1H) 4.48 (dd, J=10.48, 2.15 Hz, 2H) 7.31 (d, J=5.05 Hz, 1H) 8.69 (d, J=5.05 Hz, 1H).

Step d 2-(2-Isopropylpyrimidin-4-yl)-morpholine-4-carboxylic acid tert-butyl ester (256 mg, 833 µmol) was dissolved in 5 mL of dichloromethane and TFA (2 mL) was added. The solution was stirred at room temperature for 2 h. The solvents were evaporated. The residue was extracted with dichloromethane and 1N NaOH solution. The organic layer was dried over Na$_2$SO$_4$ and concentrated. The residue was dried under vacuum to afford 2-(2-isopropylpyrimidin-4-yl)-morpholine (175 mg) as a colorless oil. (M+H)$^+$=208 m/e.

Step e

In a 50 mL round-bottomed flask, 2-(2-isopropylpyrimidin-4-yl)morpholine (181 mg, 873 µmol) and (S)-2-(trifluoromethyl)oxirane (147 mg, 1.31 mmol) were combined in acetonitrile (3 ml) to give a colorless solution. The reaction mixture was stirred at room temperature for 3 days. Reaction was concentrated in vacuo and used as is in the next reaction. (M+H)$^+$=208 m/e.

Step f

In a 50 mL round-bottom flask, (2S)-1,1,1-trifluoro-3-(2-(2-isopropylpyrimidin-4-yl)morpholino)propan-2-ol (278 mg, 0.87 mmol) was combined with dichloromethane (12 ml) to give a colorless solution. TEA (88.0 mg, 121 µl, 870 µmol) was added. 1-chloro-2-fluoro-4-isocyanatobenzene (164 mg, 957 µmol) was added. The reaction mixture was stirred at room temperature overnight. Additional 1-chloro-2-fluoro-4-isocyanatobenzene (164 mg, 957 µmol) was added. Reaction mixture was stirred at room temperature 30 min. Complete by LCMS. The crude reaction mixture was diluted with an equal volume of hexanes and filtered. The solid was washed with dichloromethane/hexanes (1:1) twice. The combined filtrate and washes were concentrated in vacuo and the resulting residue was purified by flash chromatography (silica gel, 40 g, 5% to 30% EtOAc in hexanes). The pooled material containing product as a mixture of epimers was re-purified by flash chromatography (silica gel, 40 g, 5% to 15% EtOAc in (2:1 hexanes:dichloromethane) gradient) to afford the pure product from the front-running peak. The front-eluting product was assigned as (4-chloro-3-fluoro-phenyl)-carbamic acid (S)-2,2,2-trifluoro-1-[(S)-2-(2-isopropyl-pyrimidin-4-yl)-morpholin-4-ylmethyl]-ethyl ester. This epimer was taken up in 15 mL ether and treated with 1.5 mL of HCl in ether (1M). Upon addition a white precipitate formed, which when filtered, turned into a yellow gum. Material was recovered by free-basing with dichloromethane/10% NaHCO$_3$. Mixture was extracted 3 times with dichloromethane. The organic layers were dried over Na$_2$SO$_4$ and concentrated in vacuo. The resultant colorless oil was pure by LCMS. The oil was taken up in ether (2 mL) and transferred into a vial. The solution was treated with 1M HCl in ether (1 mL) to give a suspended white solid. The ether was removed by careful stream of N2. The resulting fluffy white solid were dried under vacuum to give (4-chloro-3-fluoro-phenyl)-carbamic acid (S)-2,2,2-trifluoro-1-[(S)-2-(2-isopropyl-pyrimidin-4-yl)-morpholin-4-ylmethyl]-ethyl ester as HCl salt as an off-white powder (141 mg). (M+H)$^+$=491 m/e.

Example 26

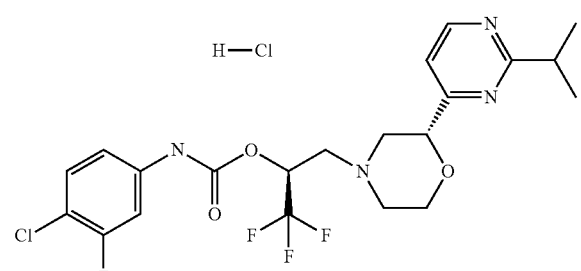

(4-Chloro-3-fluorophenyl)-carbamic acid (S)-2,2,2-trifluoro-1-[(R)-2-(2-isopropylpyrimidin-4-yl)-morpholin-4-ylmethyl]-ethyl ester hydrochloride (4-Chloro-3-fluoro-phenyl)-carbamic acid (S)-2,2,2-trifluoro-1-[(R)-2-(2-isopropyl-pyrimidin-4-yl)-morpholin-4-ylmethyl]-ethyl ester hydrochloride was prepared according to the methods described for Example 25 except isolating the late-running peak from the flash chromatography as an off-white powder (117 mg). (M+H)$^+$=491 m/e.

Example 27

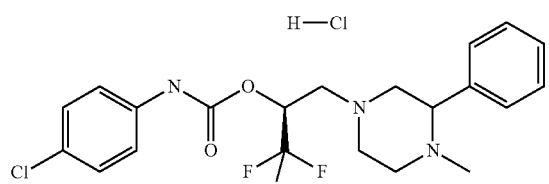

(4-Chlorophenyl)-carbamic acid (S)-2,2,2-trifluoro-1-(4-methyl-3-phenylpiperazin-1-ylmethyl)-ethyl ester hydrochloride Step a To a mixture of tert-butyl 3-phenylpiperazine-1-carboxylate (288 mg, 1.1 mmol), and formaldehyde (185 mg, 6.16 mmol) in methanol (7 mL) was added sodium triacetoxyborohydride (949 mg, 4.48 mmol) at 0° C. After stirring for 3 h at room temperature, the reaction mixture was diluted with 10% sodium bicarbonate solution and ethyl acetate. The aqueous part was extracted with ethyl acetate and the combined organic part was dried over sodium sulfate, filtered, concentrated in vacuo. The residue was purified by flash chromatography (20/1 dichloromethane/methanol) to provide 4-methyl-3-phenyl-piperazine-1-carboxylic acid tert-butyl ester (307 mg, 101%). (M+H)$^+$=277 m/e. To a solution of 4-methyl-3-phenyl-piperazine-1-carboxylic acid tert-butyl ester (307 mg, 1.11 mmol) in THF (3 mL) at 0° C. was added 4M HCl in dioxane (0.9 mL). The reaction mixture was stirred overnight and concentrated in vacuo. The residue was triturated with dichloromethane and filtered to provide 1-methyl-2-phenyl-piperazine dihydrochloride (290 mg), which was used as is for the next step.

Step b

To a mixture of 1-methyl-2-phenylpiperazine dihydrochloride (150 mg, 0.60 mmol) and DIPEA (315 µL, 1.81 mmol) in acetonitrile was added (S)-2-(trifluoromethyl)oxirane (188 µL, 1.81 mmol). The mixture was stirred at room temperature for 3.5 h and evaporated. The residue was purified by flash chromatography (15/1 dichloromethane/MeOH) to afford the desired product, (S)-1,1,1-trifluoro-3-(4-methyl-3-phenyl-piperazin-1-yl)-propan-2-ol, as an oil (180 mg, 104%). (M+H)$^+$=289 m/e.

Step c (S)-1,1,1-Trifluoro-3-(4-methyl-3-phenyl-piperazin-1-yl)-propan-2-ol (180 mg, 0.62 mmol) and 1-chloro-4-isocyanatobenzene (115 mg, 0.75 mmol) were combined in acetonitrile (5 mL). The reaction mixture was stirred overnight and evaporated. The residue was purified by flash chromatography (20/1 dichloromethane/EtOAc then 20/1 dichloromethane/MeOH) to provide the desired product. To the free-base product was added 1M HCl/ether solution to provide HCl salt form, (4-chlorophenyl)-carbamic acid (S)-2,2,2-trifluoro-1-(4-methyl-3-phenyl-piperazin-1-ylmethyl)-ethyl ester hydrochloride (150 mg) as a white solid. (M+H)$^+$=442 m/e.

Example 28

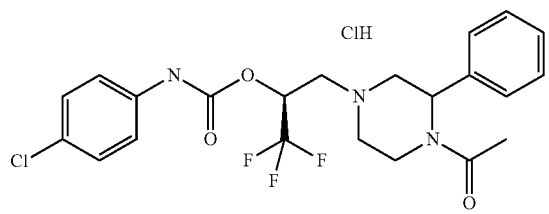 [SMILES: CC(=O)N1CCN(C[C@H](OC(=O)Nc2ccc(Cl)cc2)C(F)(F)F)CC1c1ccccc1 ; Cl]

(4-Chlorophenyl)-carbamic acid (S)-1-(4-acetyl-3-phenylpiperazin-1-ylmethyl)-2,2,2-trifluoroethyl ester hydrochloride To a mixture of tert-butyl 3-phenylpiperazine-1-carboxylate (400 mg, 1.52 mmol) and triethyl amine (309 mg, 3.05 mmol) in dichloromethane (5 mL) was added acetyl chloride (156 mg, 1.98 mmol) at 0° C. After stirring for 3 h at room temperature, the reaction mixture was diluted with saturated sodium bicarbonate solution and dichloromethane. The aqueous part was extracted with dichloromethane and the combined organic part was dried over sodium sulfate, filtered, and concentrated in vacuo. The residue was purified by flash chromatography (20/1 dichloromethane/methanol) to afford 4-acetyl-3-phenyl-piperazine-1-carboxylic acid tert-butyl ester (250 mg, 54%). [M-BOC]H+=205.

To a solution of 4-acetyl-3-phenyl-piperazine-1-carboxylic acid tert-butyl ester (250 mg, 0.82 mmol) in THF (3 mL) at 0° C. was added 50% TFA/dichloromethane (1 mL). After stirred for 2 h, the reaction mixture was concentrated in vacuo. The residue was diluted with dichloromethane and silica-bound carbonate (2 g, 0.77 mmol/g, Silicycle, Inc.) was added. The reaction mixture was stirred overnight, filtered, and concentrated in vacuo. The residue was purified by flash chromatography (10/1 dichloromethane/methanol with 1% triethyl amine) to provide 1-(2-phenyl-piperazin-1-yl)-ethanone (200 mg, 119%). (M+H)$^+$=205 m/e.

(4-Chlorophenyl)-carbamic acid (S)-1-(4-acetyl-3-phenyl-piperazin-1-ylmethyl)-2,2,2-trifluoro-ethyl ester hydrochloride was prepared by a similar procedure to Example 27 (steps b and c) except substituting 1-(2-phenyl-piperazin-1-yl)-ethanone for 1-methyl-2-phenylpiperazine dihydrochloride to afford 110 mg of the title compound as a white solid. (M+H)$^+$=470 m/e.

Example 29

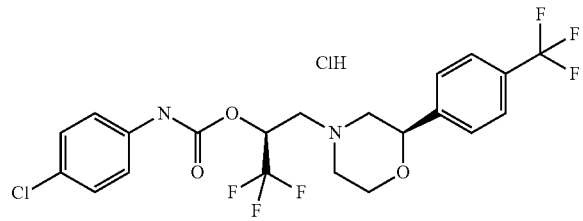 [SMILES: O=C(Nc1ccc(Cl)cc1)O[C@@H](CN1CCO[C@H](c2ccc(C(F)(F)F)cc2)C1)C(F)(F)F ; Cl]

(4-Chlorophenyl)-carbamic acid (S)-2,2,2-trifluoro-1-[(R)-2-(4-trifluoromethylphenyl)-morpholin-4-ylmethyl]-ethyl ester hydrochloride From 2-(4-(trifluoromethyl)phenyl)morpholine oxalate and (S)-2-(trifluoromethyl)oxirane, (S)-1,1,1-trifluoro-3-[2-(4-trifluoromethyl-phenyl)-morpholin-4-yl]-propan-2-ol was obtained as an oil (110 mg, 70%) by a similar procedure to that described in Example 27 (step b). (M+H)$^+$=344 m/e.

(S)-1,1,1-Trifluoro-3-[2-(4-trifluoromethyl-phenyl)-morpholin-4-yl]-propan-2-ol (52 mg, 151 µmol) and 1-chloro-4-isocyanatobenzene (25.6 mg, 167 µmol) were combined in acetonitrile (2 mL). The mixture was stirred at room temperature overnight and evaporated. The residue was purified by flash chromatography (20% EtOAc/hexanes) to provide the front-running isomer, which was converted to the HCl salt to afford (4-chloro-phenyl)-carbamic acid (S)-2,2,2-trifluoro-1-[(R)-2-(4-trifluoromethyl-phenyl)-morpholin-4-ylmethyl]-ethyl ester hydrochloride as a white solid (30 mg). (M+H)$^+$=497 m/e.

Example 30

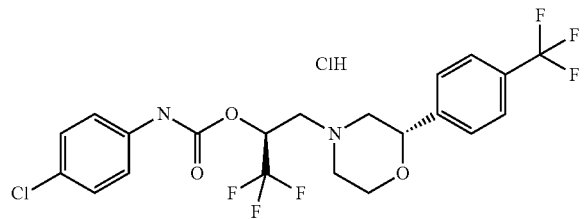 [SMILES: O=C(Nc1ccc(Cl)cc1)O[C@@H](CN1CCO[C@@H](c2ccc(C(F)(F)F)cc2)C1)C(F)(F)F ; Cl]

(4-Chlorophenyl)-carbamic acid (S)-2,2,2-trifluoro-1-[(S)-2-(4-trifluoromethylphenyl)-morpholin-4-ylmethyl]-ethyl ester hydrochloride From 2-(4-(Trifluoromethyl)phenyl)morpholine oxalate and (S)-2-(trifluoromethyl)oxirane, (S)-1,1,1-Trifluoro-3-[2-(4-trifluoromethyl-phenyl)-morpholin-4-yl]-propan-2-ol was obtained as an oil (110 mg, 70%) by a similar procedure to that described in Example 27 (step b). (M+H)$^+$=344 m/e.

(S)-1,1,1-Trifluoro-3-[2-(4-trifluoromethyl-phenyl)-morpholin-4-yl]-propan-2-ol (52 mg, 151 µmol) and 1-chloro-4-isocyanatobenzene (25.6 mg, 167 µmol) were combined in acetonitrile (2 mL). The mixture was stirred at room temperature overnight and evaporated. The residue was purified by flash chromatography (20% EtOAc/hexanes) to provide the later-running isomer, which was converted to the HCl salt to afford (4-chloro-phenyl)-carbamic acid (S)-2,2,2-trifluoro-1-[(S)-2-(4-trifluoromethyl-phenyl)-morpholin-4-ylmethyl]-ethyl ester hydrochloride as a white solid (30 mg). (M+H)$^+$=497 m/e.

Example 31

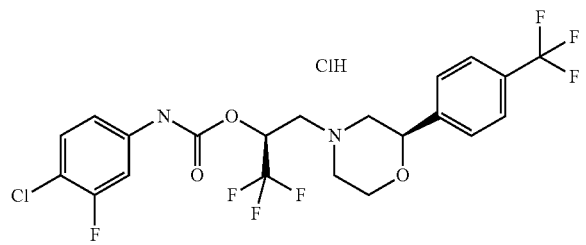 [SMILES: O=C(Nc1ccc(Cl)c(F)c1)O[C@@H](CN1CCO[C@H](c2ccc(C(F)(F)F)cc2)C1)C(F)(F)F ; Cl]

(4-Chloro-3-fluorophenyl)carbamic acid (S)-2,2,2-trifluoro-1-[(R)-2-(4-trifluoromethylphenyl)-morpholin-4-ylmethyl]-ethyl ester hydrochloride Preparing by a similar procedure to Example 29 except substituting 1-chloro-2-fluoro-4-isocyanatobenzene for 1-chloro-4-isocyanatobenzene afforded 24 mg of the title compound as a white solid. M+=514 m/e.

Example 32

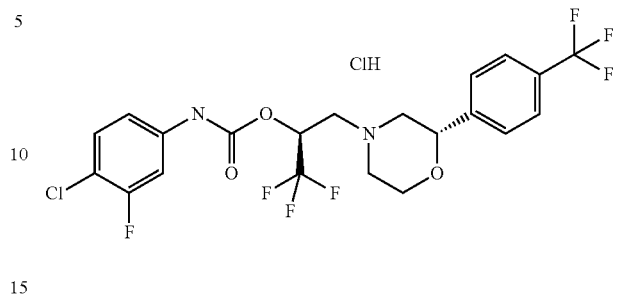

(4-Chloro-3-fluorophenyl)-carbamic acid (S)-2,2,2-trifluoro-1-[(S)-2-(4-trifluoromethylphenyl)-morpholin-4-ylmethyl]-ethyl ester hydrochloride Preparing by a similar procedure to Example 30 except substituting 1-chloro-2-fluoro-4-isocyanatobenzene for 1-chloro-4-isocyanatobenzene afforded 15 mg of the title compound as a white solid. M+=514.

Example 33

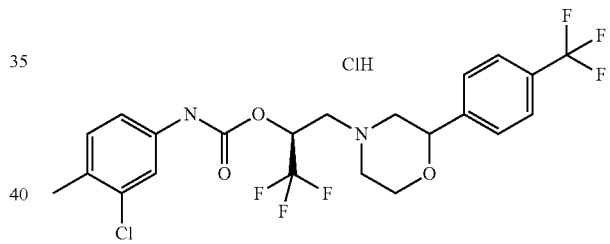

(3-Chloro-4-methylphenyl)-carbamic acid (S)-2,2,2-trifluoro-1-[2-(4-trifluoromethylphenyl)-morpholin-4-ylmethyl]-ethyl ester hydrochloride (S)-1,1,1-Trifluoro-3-[2-(4-trifluoromethyl-phenyl)-morpholin-4-yl]-propan-2-ol (50 mg, 146 µmol) and 2-chloro-4-isocyanato-1-methylbenzene (prepared by a similar procedure as for intermediate A, 24.4 mg, 146 µmol) were combined in acetonitrile (1 mL). A mixture was stirred at room temperature overnight and evaporated. The residue was purified by flash chromatography (20% EtOAc/hexanes) to provide (3-chloro-4-methylphenyl)-carbamic acid (S)-2,2,2-trifluoro-1-[2-(4-trifluoromethyl-phenyl)-morpholin-4-ylmethyl]-ethyl ester, which was converted to the HCl salt to afford (3-chloro-4-methylphenyl)-carbamic acid (S)-2,2,2-trifluoro-1-[2-(4-trifluoromethyl-phenyl)-morpholin-4-ylmethyl]-ethyl ester hydrochloride as a white solid (15 mg). (M+H)$^+$=511 m/e.

Example 34

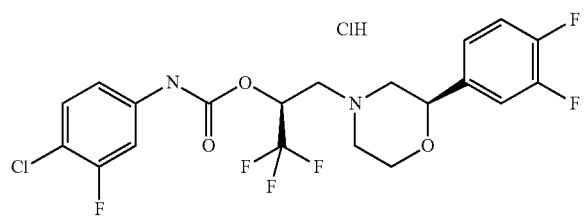 [SMILES: O=C(Nc1ccc(Cl)c(F)c1)O[C@@H](CN1CCO[C@H](c2ccc(F)c(F)c2)C1)C(F)(F)F ; Cl]

(4-Chloro-3-fluorophenyl)-carbamic acid (S)-1-[(R)-2-(3,4-difluorophenyl)-morpholin-4-ylmethyl]-2,2,2-trifluoroethyl ester hydrochloride To a mixture of 2-(3,4-difluorophenyl)-morpholine (250 mg, 1.26 mmol) and acetonitrile (3 mL) was added (S)-2-(trifluoromethyl)oxirane (196 µL, 1.88 mmol). The mixture was stirred at room temperature for 3 h and evaporated. The residue was purified by flash chromatography (40% ethyl acetate in hexane) to afford the desired product, (S)-3-[(R)-2-(3,4-difluoro-phenyl)-morpholin-4-yl]-1,1,1-trifluoro-propan-2-ol, as an oil (224 mg, 57%) which was used as is for the next step.

(S)-3-[2-(3,4-Difluorophenyl)-morpholin-4-yl]-1,1,1-trifluoro-propan-2-ol (100 mg, 321 µmol) and 1-chloro-2-fluoro-4-isocyanatobenzene (57.9 mg, 337 µmol) were combined in acetonitrile (2 mL). The mixture was stirred at room temperature overnight. Reaction had not progressed. DIPEA (61 µL, 350 µmol) was added and the reaction mixture was warmed at 80° C. for 3 h. The solvent was evaporated. The residue was purified by flash chromatrography (30% EtOAc/hexanes) to provide the front-running isomer, which was converted to the HCl salt to afford (4-chloro-3-fluoro-phenyl)-carbamic acid (S)-1-[(R)-2-(3,4-difluoro-phenyl)-morpholin-4-ylmethyl]-2,2,2-trifluoro-ethyl ester hydrochloride (55 mg, 36%). (M+H)$^+$=483 m/e. $^1$H NMR (400 MHz, DMSO-d$_6$) δ ppm 2.18 (t, J=10.79 Hz, 1H) 2.22-2.32 (m, 1H) 2.73-2.87 (m, 2H) 2.94 (d, J=11.29 Hz, 2H) 3.48-3.61 (m, 1H) 3.95 (d, J=10.04 Hz, 1H) 4.43 (d, J=8.28 Hz, 1H) 5.58-5.73 (m, 1H) 7.15-7.25 (m, 1H) 7.27-7.47 (m, 3H) 7.49-7.65 (m, 2H) 10.53 (s, 1H).

Example 35

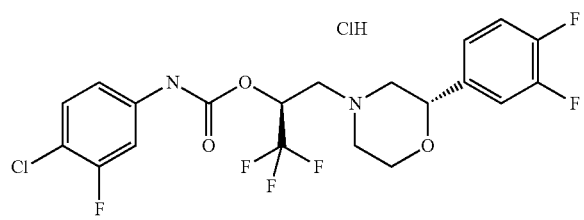 [SMILES: O=C(Nc1ccc(Cl)c(F)c1)O[C@@H](CN1CCO[C@@H](c2ccc(F)c(F)c2)C1)C(F)(F)F ; Cl]

(4-Chloro-3-fluorophenyl)-carbamic acid (S)-1-[(S)-2-(3,4-difluorophenyl)-morpholin-4-ylmethyl]-2,2,2-trifluoroethyl ester hydrochloride (4-Chloro-3-fluoro-phenyl)-carbamic acid (S)-1-[(S)-2-(3,4-difluoro-phenyl)-morpholin-4-ylmethyl]-2,2,2-trifluoro-ethyl ester hydrochloride was prepared according to the methods described for Example 34 except isolating the late-running peak from the flash chromatography (40 mg, 26%). (M+H)$^+$=483 m/e. $^1$H NMR (400 MHz, DMSO-d$_6$) δ ppm 2.07 (t, J=10.54 Hz, 1H) 2.36-2.47 (m, 1H) 2.76 (d, J=11.54 Hz, 1H) 2.82 (d, J=6.27 Hz, 2H) 3.15 (d, J=11.04 Hz, 1H) 3.54-3.64 (m, 1H) 3.92 (d, J=11.54 Hz, 1H) 4.39 (d, J=8.28 Hz, 1H) 5.67 (q, J=6.69 Hz, 1H) 7.16-7.24 (m, 1H) 7.27-7.47 (m, 3H) 7.50-7.62 (m, 2H) 10.52 (s, 1H).

Example 36

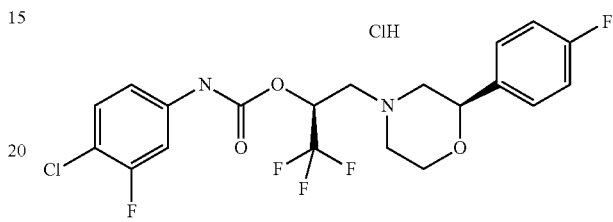

(4-Chloro-3-fluorophenyl)carbamic acid (S)-1-[(R)-2-(4-fluorophenyl)-morpholin-4-ylmethyl]-2,2,2-trifluoroethyl ester hydrochloride A mixture of 2-(4-fluorophenyl)-morpholine (300 mg, 1.66 mmol) and (S)-2-(trifluoromethyl)oxirane (173 µL, 1.66 mmol) in acetonitrile (3 mL) was stirred in a sealed tube at room temperature overnight and evaporated. The residue was purified by flash chromatography (40% ethyl acetate in hexane) to afford the desired product, (S)-3-[2-(4-fluorophenyl)-morpholin-4-yl]-1,1,1-trifluoro-propan-2-ol, as an oil (490 mg, 100%) which was used as is for the next step.

(S)-3-[2-(4-fluorophenyl)-morpholin-4-yl]-1,1,1-trifluoro-propan-2-ol (100 mg, 341 µmol), DIPEA (71.3 µL, 409 µmol) and 1-chloro-2-fluoro-4-isocyanatobenzene (70.2 mg, 409 µmol) were combined in dichloromethane (5 mL). The mixture was stirred at 70° C. overnight. The solvent was evaporated. The residue was purified by flash chromatography (30% EtOAc/hexanes) to provide the front-running isomer, which was converted to the HCl salt to afford (4-Chloro-3-fluoro-phenyl)-carbamic acid (S)-1-[(R)-2-(4-fluorophenyl)-morpholin-4-ylmethyl]-2,2,2-trifluoro-ethyl ester hydrochloride (48 mg, 30%). (M+H)$^+$=465 m/e. $^1$H NMR (400 MHz, DMSO-d$_6$) δ ppm 2.13-2.32 (m, 2H) 2.73-2.85 (m, 2H) 2.93 (t, J=13.68 Hz, 2H) 3.49-3.60 (m, 1H) 3.94 (d, J=10.04 Hz, 1H) 4.41 (d, J=8.28 Hz, 1H) 5.66 (d, J=4.02 Hz, 1H) 7.16 (t, J=8.91 Hz, 2H) 7.28-7.42 (m, 3H) 7.50-7.63 (m, 2H) 10.54 (s, 1H).

Example 37

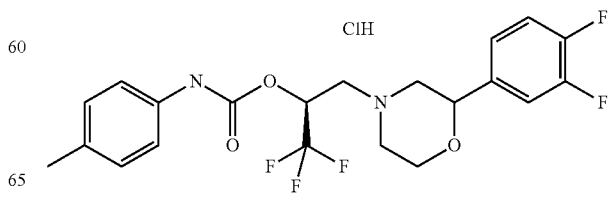

p-Tolylcarbamic acid (S)-1-[2-(3,4-difluorophenyl)-morpholin-4-ylmethyl]-2,2,2-trifluoroethyl ester hydrochloride (S)-3-[2-(3,4-Difluorophenyl)-morpholin-4-yl]-1,1,1-trifluoro-propan-2-ol (86 mg, 276 µmol), TEA (46 µL, 332 µmol) and 1-isocyanato-4-methyl-benzene (44.1 mg, 332 µmol) were combined in acetonitrile (3 mL). The mixture was stirred at 85° C. for 2 h. The solvent was evaporated. The residue was purified by flash chromatography (30% EtOAc/hexanes) to afford the desired product, which was converted to the HCl salt to afford p-tolylcarbamic acid (S)-1-[2-(3,4-difluoro-phenyl)-morpholin-4-ylmethyl]-2,2,2-trifluoroethyl ester hydrochloride as a white solid (105 mg, 79%). MS=444 m/e. $^1$H NMR (400 MHz, DMSO-d$_6$) δ ppm 2.02-2.21 (m, 1H) 2.71-3.18 (m, 4H) 3.58 (dtd, J=16.47, 11.34, 11.34, 2.26 Hz, 1H) 3.94 (t, J=8.41 Hz, 1H) 4.34-4.48 (m, 1H) 5.56-5.68 (m, 1H) 7.13 (d, J=8.53 Hz, 2H) 7.16-7.23 (m, 1H) 7.27-7.47 (m, 4H) 10.02 (br. s., 1H).

Example 38

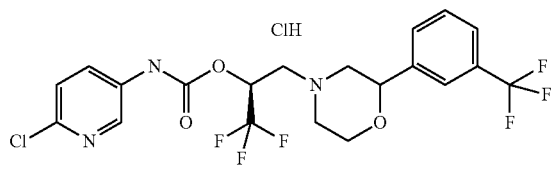 [SMILES: O=C(Nc1ccc(Cl)nc1)O[C@@H](CN1CCOC(c2cccc(C(F)(F)F)c2)C1)C(F)(F)F ; Cl]

(6-Chloropyridin-3-yl)carbamic acid (S)-2,2,2-trifluoro-1-[2-3-trifluoromethylphenyl]-morpholin-4-ylmethyl]-ethyl ester hydrochloride To a mixture of 6-chloronicotinic acid (79.4 mg, 0.5 mmol), (S)-1,1,1-trifluoro-3-[2-(3-trifluoromethyl-phenyl)-morpholin-4-yl]-propan-2-ol (173 mg, 0.5 mmol) and triethylamine (51 mg, 0.5 mmol) in toluene (3 mL) was added diphenylphosphoryl azide (139 mg, 0.5 mmol). The mixture was stirred for 30 min and then heated at 80° C. for 4 h. The solvent was concentrated in vacuo and the residue was diluted with ethyl acetate. The organic solution was washed with saturated sodium bicarbonate solution and then concentrated in vacuo. The residue was purified by flash chromatography (25% EtOAc/hexane) and converted to the HCl salt to afford (6-chloro-pyridin-3-yl)-carbamic acid (S)-2,2,2-trifluoro-1-[2-3-trifluoromethyl-phenyl]-morpholin-4-ylmethyl]-ethyl ester as a sticky oil. (M+H)$^+$=498 m/e. 1M HCl in ethyl ether was added to provide the corresponding HCl salt as a white solid (12 mg, 5%). (M+H)$^+$=498 m/e.

Example 39

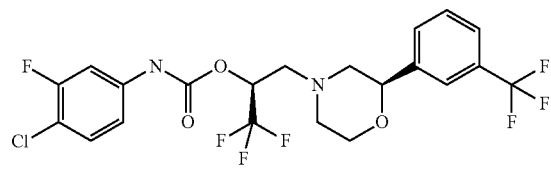 [SMILES: O=C(Nc1ccc(Cl)c(F)c1)O[C@@H](CN1CCO[C@H](c2cccc(C(F)(F)F)c2)C1)C(F)(F)F]

(S)—N-(4-chloro-3-fluorophenyl)-4,4,4-trifluoro-3-[(R)-2-(3-trifluoromethylphenyl)-morpholin-4-ylmethyl]-butyramide Step a A mixture of 4.203 g (25 mmol) of ethyl 4,4,4-trifluoro-crotonate, 20 mL of nitromethane and ca. 0.576 g (5 mmol) of tetramethyl guanidine was stirred for 13 h at room temperature, and then diluted with water and acidified by the addition of 0.5 M sulfuric acid. The mixture was extracted three times with diethyl ether. The combined ether extracts were washed with water, and then brine, dried over anhydrous sodium sulfate, filtered and concentrated under reduced pressure. to give 5.601 g (98%) of 4,4,4-trifluoro-3-nitromethyl-butyric acid ethyl ester as an amber oil. $^1$H NMR (400 MHz, DMSO-d$_6$) δ ppm 1.21 (t, J=7.15 Hz, 3H) 2.76 (dd, J=6.53, 1.76 Hz, 2H) 3.61-3.84 (m, 1H) 4.13 (q, J=7.11 Hz, 2H) 4.83-5.01 (m, 2H).

Step b

A mixture of 0.617 g (11 mmol) of potassium hydroxide and 100 mL of water was cooled in an ice bath and 2.292 g (10 mmol) of racemic 4,4,4-trifluoro-3-nitromethyl-butyric acid ethyl ester in 20 mL of tetrahydrofuran was added over 7 min. The mixture was stirred for 30 min, then 1.384 (11.5 mmol) g of magnesium sulfate in 20 mL of water was added, followed by 1.343 g (8.5 mmol) of potassium permanganate in 100 mL of water was added over 12.5 min. The mixture was stirred for 25 min, then filtered through Celite, washing with dichloromethane. The dichloromethane layer of the filtrate was washed with brine, dried over anhydrous sodium sulfate, filtered and concentrated under reduced pressure (200 mm Hg) to give 1.423 g of an oil which, by NMR analysis, contained ca. 0.427 g (22%) of 4,4,4-trifluoro-3-formyl-butyric acid ethyl ester. Used as is in the next step.

Step c

A mixture of the unpurified racemic 4,4,4-trifluoro-3-formyl-butyric acid ethyl ester from above (step b), 0.498 g (2.15 mmol) of (R)-2-(3-trifluoromethyl-phenyl)-morpholine [prepared from (R)-2-(3-trifluoromethyl-phenyl)oxirane in a similar manner to that described in Example 4 (steps b-e)], 0.162 g (2.7 mmol) of acetic acid and 8 mL of dichloromethane was stirred at room temperature. After 30 min, 0.913 g (4.3 mmol) of sodium triacetoxyborohydride was added. The mixture was stirred overnight at room temperature and then diluted with ethyl acetate and washed successively with 0.5 M sodium carbonate solution, water and then brine. The organic layer was dried over anhydrous sodium sulfate, filtered and concentrated under reduced pressure. The residue was purified by chromatography on silica gel, eluting with hexanes-ethyl acetate (90:10) to give 0.592 g (66%) of 4,4,4-trifluoro-3-[(R)-2-(3-trifluoromethyl-phenyl)-morpholin-4-ylmethyl]-butyric acid ethyl ester as an oil. Used as is in the next step Step d A mixture of 0.589 g (1.4 mmol) of 4,4,4-trifluoro-3-[(R)-2-(3-trifluoromethyl-phenyl)-morpholin-4-ylmethyl]-butyric acid ethyl ester, ca. 1.07 mL of 2 M sodium hydroxide solution and 14 mL of ethanol was heated at reflux and stirred under an atmosphere of argon. After 25 min, volatiles were removed under reduced pressure. The mixture was treated with 40 mL of saturated sodium dihydrogen phosphate solution, and extracted twice with ethyl acetate. The combined ethyl acetate layers were washed with brine, dried over anhydrous sodium sulfate, filtered and concentrated under reduced pressure to give 0.543 g (99%) of 4,4,4-trifluoro-3-[(R)-2-(3-trifluoromethylphenyl)-morpholin-4-ylmethyl]-butyric acid as a glass. $^1$H NMR (400 MHz, DMSO-d$_6$) δ ppm 2.10-2.21

(m, 1H) 2.31-2.66 (m, 3H overlapping DMSO) 2.79 (dd, J=16.81, 11.54 Hz, 1H) 2.95-3.21 (m, 2H) 3.34 (s, 2H) 3.65 (dtd, J=18.23, 11.34, 11.34, 2.26 Hz, 1H) 3.91-4.02 (m, 1H) 4.45-4.64 (m, 1H) 7.53-7.75 (m, 4H) 12.49 (br. s., 1H).

Step e

To a solution of 0.540 g (1.4 mmol) of 4,4,4-trifluoro-3-[(R)-2-(3-trifluoromethyl-phenyl)-morpholin-4-ylmethyl]-butyric acid, 0.003 g of dimethylformamide and 6 mL of dichloromethane was added a solution of 0.534 g (4.2 mmol) of oxalyl chloride. After 2 h the mixture was concentrated under reduced pressure to give the corresponding acid chloride as a light yellow foam. To this residue, was added 0.255 g (1.75 mmol) of 4-chloro-3-fluoro-aniline and 5 mL of dichloromethane, followed by a solution of ca. 0.887 g (11.2 mmol) of pyridine in 3 mL of dichloromethane. The mixture was stirred at room temperature for 5 h, and then diluted with ethyl acetate, washed successively with saturated sodium bicarbonate, water, brine, dried over anhydrous sodium sulfate, filtered and concentrated under reduced pressure. The crude material was purified by chromatography on silica gel, eluting with hexanes-ethyl acetate (80:20), followed by chromatography on silica gel, eluting with hexanes-dichloromethane-ethyl acetate (60:35:5) to give 0.116 g (16%) of (S)—N-(4-chloro-3-fluoro-phenyl)-4,4,4-trifluoro-3-[(R)-2-(3-trifluoromethyl-phenyl)-morpholin-4-ylmethyl]-butyramide as the front-running peak as a light yellow foam. (M+H)$^+$=513 m/e.

Example 40

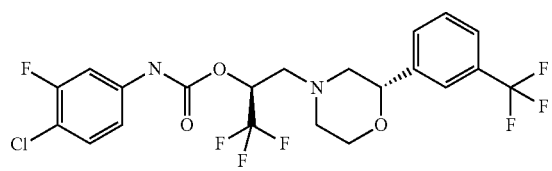 [SMILES: O=C(Nc1ccc(Cl)c(F)c1)O[C@@H](CN1CCO[C@@H](c2cccc(C(F)(F)F)c2)C1)C(F)(F)F]

(S)—N-(4-chloro-3-fluorophenyl)-4,4,4-trifluoro-3-[(S)-2-(3-trifluoromethylphenyl)-morpholin-4-ylmethyl]-butyramide (S)—N-(4-chloro-3-fluoro-phenyl)-4,4,4-trifluoro-3-[(S)-2-(3-trifluoromethyl-phenyl)-morpholin-4-ylmethyl]-butyramide was prepared according to the methods described for Example 39 except isolating the late-running peak from the flash chromatography (0.181 g, 25%). (M+H)$^+$=513 m/e.

Example 41

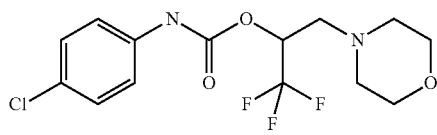 [SMILES: O=C(Nc1ccc(Cl)cc1)OC(CN1CCOCC1)C(F)(F)F]

(4-Chlorophenyl)-carbamic acid 2,2,2-trifluoro-1-morpholin-4-ylmethyl-ethyl ester To a round bottomed flask containing 3.136 g (36 mmol) of morpholine was added 3.362 g (30 mmol) of racemic 1,1,1-trifluoro-2,3-epoxypropane dropwise over 10 min (exothermic). The mixture was stirred at room temperature. After 90 min, the volatiles were removed under reduced pressure to give 5.837 g (98%) of 1,1,1-trifluoro-3-morpholin-4-yl-propan-2-ol as an oil.

In a round bottomed reaction vessel, under argon, was placed 0.239 g (1.2 mmol) of 1,1,1-trifluoro-3-morpholin-4-yl-propan-2-ol and 0.203 g (1.3 mmol) of 4-chlorophenyl isocyanate. The vessel was capped, set in a bath at 85° C. and stirred. After 90 min, the mixture was cooled. The crude material was purified by chromatography on silica gel, eluting with hexanes-ethyl acetate (90:10), to give 0.250 g (59%) of (4-chloro-phenyl)-carbamic acid 2,2,2-trifluoro-1-morpholin-4-ylmethyl-ethyl ester as a white crystalline solid. (M+H)$^+$=353 m/e.

Example 42

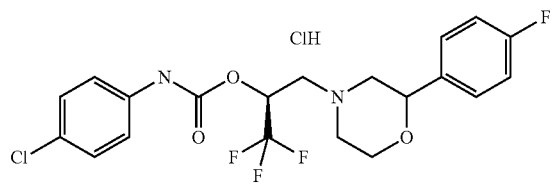 [SMILES: O=C(Nc1ccc(Cl)cc1)O[C@@H](CN1CCOC(c2ccc(F)cc2)C1)C(F)(F)F ; Cl]

(4-Chlorophenyl)carbamic acid (S)-2,2,2-trifluoro-1-[2-(4-fluorophenyl)-morpholin-4-ylmethyl]-ethyl ester hydrochloride To a solution of 2-(4-fluorophenyl)morpholine oxalate (50 mg, 184 μmol) and triethylamine (128 μL, 922 μmole) in 2.5 mL of acetonitrile was added (S)-2-(trifluoromethyl)oxirane (82.6 mg, 737 μmol) at room temperature. The mixture was stirred at this temperature for 4 days. The solution was purified by reverse phase column chromatography (30-100% acetonitrile in water). The desired fractions were pooled and lyophilized to give (2S)-1,1,1-trifluoro-3-(2-(4-fluorophenyl)morpholino)propan-2-ol (39 mg, 73%). Used as is in the next step.

(2S)-1,1,1-trifluoro-3-(2-(4-fluorophenyl)morpholino)propan-2-ol (39 mg, 133 μmol), TEA (92.7 μL, 665 μmol) and 1-chloro-4-isocyanatobenzene (20.4 mg, 133 μmol) were combined in 2 mL of acetonitrile and stirred at room temperature overnight. Several drops of DMSO were added to the mixture to make a clear solution. The solution was separated by reverse phase column chromatography (50-100% acetonitrile in water). The desired fractions were pooled, treated with 5 drops of conc. HCl and the solution lyophilized to afford the title compound (38 mg, 59%) as a white solid. (M+H)$^+$=447 m/e.

Example 43

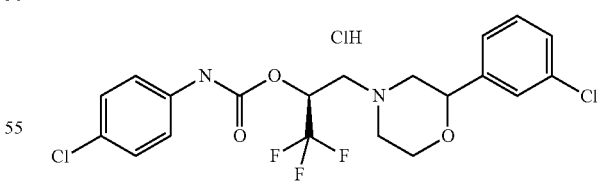

(4-Chlorophenyl)-carbamic acid (S)-2,2,2-trifluoro-1-[2-(3-chlorophenyl)-morpholin-4-ylmethyl]-ethyl ester hydrochloride Prepared by a similar procedure to Example 42 except substituting 2-(3-chlorophenyl)morpholine hydrochloride for 2-(4-fluorophenyl)morpholine oxalate afforded 34.5 mg of the title compound as a white solid. (M+H)$^+$=463, 465 m/e.

Example 44

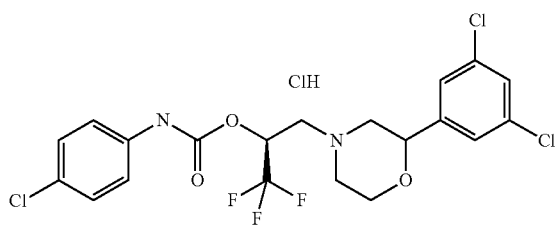 [SMILES: O=C(Nc1ccc(Cl)cc1)O[C@@H](CN1CCOC(c2cc(Cl)cc(Cl)c2)C1)C(F)(F)F ; Cl]

(4-Chlorophenyl)-carbamic acid (S)-2,2,2-trifluoro-1-[2-(3,5-dichlorophenyl)-morpholin-4-ylmethyl]-ethyl ester hydrochloride Prepared by a similar procedure to Example 42 except substituting 2-(3,5-dichlorophenyl)morpholine hydrochloride for 2-(4-fluorophenyl)morpholine oxalate afforded 22.6 mg of the title compound as a white solid. $(M+H)^+=497$ m/e.

Example 45

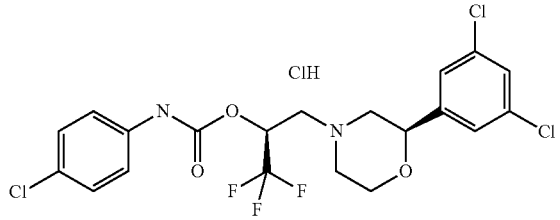 [SMILES: O=C(Nc1ccc(Cl)cc1)O[C@@H](CN1CCO[C@H](c2cc(Cl)cc(Cl)c2)C1)C(F)(F)F ; Cl]

(4-Chlorophenyl)carbamic acid (S)-1-[(R)-2-(3,5-dichlorophenyl)-morpholin-4-ylmethyl]-2,2,2-trifluoroethyl ester hydrochloride 2-(3,5-Dichlorophenyl)morpholine oxalate (1 g) from Chem-Impex was added to 5% aq NaOH and dichloromethane and extracted (3×100 mL dichloromethane). Combined extracts were dried over $Na_2SO_4$, filtered and concentrated to afford 728 mg of 2-(3,5-dichlorophenyl)morpholine as the free-base. In a 100 mL round-bottom flask, 2-(3,5-dichlorophenyl)morpholine (728 mg, 3.14 mmol) and (S)-2-(trifluoromethyl)oxirane (527 mg, 4.7 mmol) were combined with acetonitrile (10.0 ml) to give a yellow solution. Stirring was continued at room temperature for 3 days. Reaction mixture was concentrated in vacuo. The crude material was purified by flash chromatography (silica gel, 40 g, 5% to 20% EtOAc in hexanes) to afford (2S)-3-(2-(3,5-dichlorophenyl)morpholino)-1,1,1-trifluoropropan-2-ol (1.06 g, 98%) as a colorless oil. $(M+H)^+=344$, 346 m/e. Used as is.

In a 50 mL round-bottom flask, (2S)-3-(2-(3,5-dichlorophenyl)morpholino)-1,1,1-trifluoropropan-2-ol (665 mg, 1.93 mmol) was combined with dichloromethane (12 ml) to give a colorless solution. TEA (196 mg, 269 µl, 1.93 mmol) was added. 1-chloro-4-isocyanatobenzene (326 mg, 2.13 mmol) was added. The reaction mixture was stirred at room temperature overnight. Two major close-running spots of similar intensity could be seen by TLC (silica 10% EtOAc in hexanes eluent), a front-running spot and a later-running spot. The crude material was purified by flash chromatography (silica gel, 40 g, 5% to 20% EtOAc in hexanes gradient). The fractions that contained mostly front peak were pooled, concentrated and purified again by chromatography (silica, 40 g, 5-15% (3:1 dichloromethane:EtOAc) in hexane gradient) affording pure front peak product, assigned as (4-chlorophenyl)-carbamic acid (S)-1-[(R)-2-(3,5-dichloro-phenyl)-morpholin-4-ylmethyl]-2,2,2-trifluoro-ethyl ester. This product was taken up in ether (30 mL) and treated with 1M HCl in ether (2.5 mL). Hexanes was added and the mixture was concentrated in vacuo to afford (4-chloro-phenyl)-carbamic acid (S)-1-[(R)-2-(3,5-dichloro-phenyl)-morpholin-4-ylmethyl]-2,2,2-trifluoro-ethyl ester hydrochloride (185 mg) as an off-white powder. $(M+H)^+=497$, 499 m/e.

Example 46

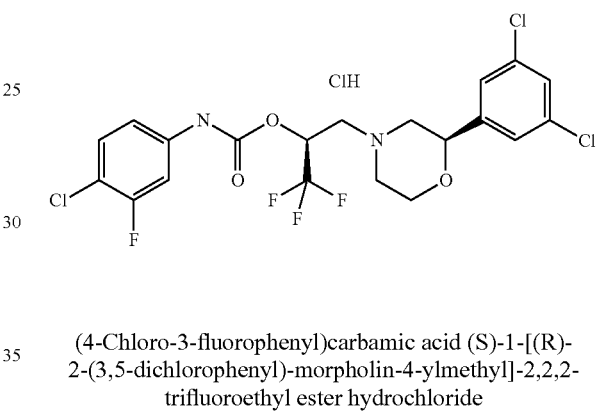

(4-Chloro-3-fluorophenyl)carbamic acid (S)-1-[(R)-2-(3,5-dichlorophenyl)-morpholin-4-ylmethyl]-2,2,2-trifluoroethyl ester hydrochloride In a 50 mL round-bottom flask, (2S)-3-(2-(3,5-dichlorophenyl)morpholino)-1,1,1-trifluoropropan-2-ol (prepared in Example 45, 400 mg, 1.16 mmol) was combined in dichloromethane (12 ml) to give a colorless solution. TEA (118 mg, 162 µl, 1.16 mmol) was added. 1-chloro-2-fluoro-4-isocyanatobenzene (219 mg, 1.28 mmol) was added. The reaction mixture was stirred at room temperature overnight. Reaction was not complete by LCMS. Additional 1-chloro-2-fluoro-4-isocyanatobenzene (219 mg, 1.28 mmol) was added. Reaction was stirred at room temperature for 30 min. Complete by LCMS. The reaction mixture was diluted with an equal volume of hexanes and filtered. The precipitate was washed with dichloromethane/hexanes (1:1) twice. The crystalline solid was pure symmetrical urea. The combined filtrate and washes were concentrated. Two major close-running spots of similar intensity could be seen by TLC (silica 10% EtOAc in hexanes eluent), a front-running spot and a later-running spot. The resulting residue was purified by flash chromatography (silica gel, 40 g, 5% to 10% EtOAc in hexanes). The front spot was isolated to provide pure product, assigned as epimer (4-chloro-3-fluoro-phenyl)-carbamic acid (S)-1-[(R)-2-(3,5-dichloro-phenyl)-morpholin-4-ylmethyl]-2,2,2-trifluoro-ethyl ester. This product was taken up in ether, treated with 1M HCl in ether (2 mL). Hexane was added and the mixture was concentrated in vacuo to afford (4-chloro-3-fluorophenyl)-carbamic acid (S)-1-[(R)-2-(3,5-dichloro-phenyl)-morpholin-4-ylmethyl]-2,2,2-trifluoro-ethyl ester hydrochloride as a white powder (193 mg). $(M+H)^+=515$, 517 m/e.

Example 47

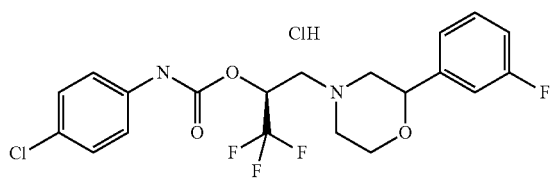 [SMILES: O=C(Nc1ccc(Cl)cc1)O[C@@H](CN1CCOC(c2cccc(F)c2)C1)C(F)(F)F ; Cl]

(4-Chlorophenyl)-carbamic acid (S)-2,2,2-trifluoro-1-[2-(3-fluorophenyl)-morpholin-4-ylmethyl]-ethyl ester hydrochloride Prepared by a similar procedure to Example 42 except substituting 2-(3-fluorophenyl)morpholine hydrochloride for 2-(4-fluorophenyl)morpholine oxalate afforded 22.6 mg of the title compound as an white solid. (M+H)$^+$=447 m/e.

Example 48

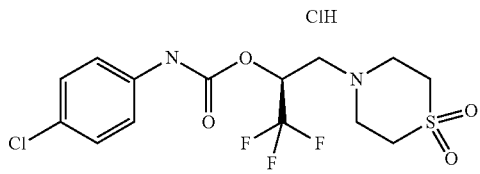 [SMILES: Cl ; O=C(Nc1ccc(Cl)cc1)O[C@@H](CN1CCS(=O)(=O)CC1)C(F)(F)F]

(4-Chlorophenyl)-carbamic acid (S)-1-(1,1-dioxo-1λ$^6$-thiomorpholin-4-ylmethyl)-2,2,2-trifluoroethyl ester hydrochloride In a 2 ml vial, thiomorpholine 1,1-dioxide (200 mg, 1.48 mmol) was combined with acetonitrile (5.33 ml) to give a colorless solution. (S)-2-(trifluoromethyl)oxirane (332 mg, 257 µl, 2.96 mmol) was added and the resultant mixture was stirred at room temperature for 2 h. The crude reaction mixture was concentrated in vacuo to afford 120 mg of (S)-3-(1,1-dioxo-1λ$^6$-thiomorpholin-4-yl)-1,1,1-trifluoro-propan-2-ol as an oil, which was used without further purification.

In a 10 mL round-bottomed flask, (S)-3-(1,1-dioxo-1λ$^6$-thiomorpholin-4-yl)-1,1,1-trifluoro-propan-2-ol (120 mg, 485 µmol) was combined with acetonitrile (5.00 ml) to give a colorless solution. 1-Chloro-4-isocyanatobenzene (74.5 mg, 485 µmol) was added and the resulting mixture was stirred at room temperature overnight. The crude reaction mixture was concentrated in vacuo and purified on a silica column (hexane to 60% EtOAc/hexane gradient) to afford an oil. This oil was dissolved in ether and hexane and a 4N HCl solution (0.2 ml) was added and the mixture concentrated to afford 50 mg of (4-chlorophenyl)-carbamic acid (S)-1-(1,1-dioxo-1λ$^6$-thiomorpholin-4-ylmethyl)-2,2,2-trifluoroethyl ester hydrochloride as a white solid. (M+H)$^+$=401 m/e.

Example 49

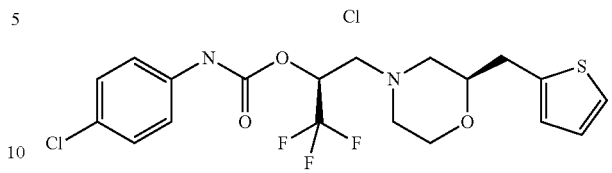

(4-Chlorophenyl)-carbamic acid (S)-2,2,2-trifluoro-1-((R)-2-thiophen-2-ylmethyl-morpholin-4-ylmethyl)-ethyl ester hydrochloride Step a To a solution of 2-bromothiophene (0.95 mL, 9 mmol) in ether (60 mL) cooled to −100° C. was added t-butyl lithium (5.41 mL of 1.7 M in pentane, 9 mmol) by dropwise addition. The reaction mixture was stirred at this temperature for 30 min. (R)-Epichlorohydrin (1.08 mL, 14 mmol) was added and the −100° C. bath was replaced with an ice/ethanol bath. The reaction was stirred at this temperature for 1.5 h and then stirred in an ice-bath for an additional 1.5 h. The reaction mixture was poured onto water and extracted with EtOAc (3 times). The combined organic phases were washed with brine, dried over MgSO$_4$ and concentrated. The residue was purified by flash chromatography (50% EtOAc in heptane eluent) to afford (R)-1-chloro-3-thiophen-2-yl-propan-2-ol (410 mg, 25%) as a brown oil. $^1$H NMR (300 MHz, CHLOROFORM-d) δ ppm 2.28 (d, J=4.14 Hz, 1H) 3.06-3.21 (m, 2H) 3.46-3.73 (m, 2H) 4.08 (d, J=5.65 Hz, 1H) 6.91 (dd, J=3.39, 0.94 Hz, 1H) 6.98 (dd, J=5.09, 3.39 Hz, 1H) 7.21 (dd, J=5.18, 1.22 Hz, 1H).

Step b (R)-1-chloro-3-thiophen-2-yl-propan-2-ol (410 mg, 2 mmol) was dissolved in methanol (1 mL) and treated with a solution of sodium hydroxide (557 mg, 14 mmol) in water (0.5 mL). The reaction mixture was stirred at room temperature for 5 min. Then 2-aminoethylhydrogen sulfate (1.31 g, 9 mmol) was added and the reaction mixture was stirred at 45° C. for 2.75 h. Solid sodium hydroxide (600 mg) and toluene (5 mL) were added and the reaction was heated at 65° C. overnight. The reaction mixture was poured onto water and extracted 3 times with EtOAc. The combined organic phase was washed with brine, dried over MgSO$_4$, filtered and evaporated. Purification by flash chromatography (9:1:0.1 dichloromethane:methanol:ammonia) afforded (R)-2-(thiophen-2-ylmethyl)-morpholine (205 mg, 48%). $^1$H NMR (300 MHz, CHLOROFORM-d) δ ppm 2.59 (dd, J=12.15, 10.06 Hz, 1H) 2.72-2.96 (m, 4H) 2.97-3.11 (m, 1H) 3.55-3.74 (m, 2H) 3.81-3.98 (m, 1H) 6.84 (dd, J=3.32, 0.85 Hz, 1H) 6.93 (dd, J=5.12, 3.42 Hz, 1H) 7.15 (dd, J=5.22, 1.23 Hz, 1H).

Step c

In a 25 mL round-bottom flask was placed (R)-2-(thiophen-2-ylmethyl)morpholine (121 mg, 1.08 mmol), followed by (S)-2-(trifluoromethyl)oxirane (180 mg, 0.98 mmol) and 0.3 mL of dichloromethane. The resultant mixture was stirred at room temperature for 3 days. LCMS showed mostly desired product. (M+H)$^+$=296 m/e. Reaction mixture was concentrated under a stream of nitrogen and used as is in the next step.

Step d

In 50 mL round-bottom flask (S)-1,1,1-trifluoro-3-((R)-2-(thiophen-2-ylmethyl)morpholino)propan-2-ol (289 mg, 0.98 mmol) was combined with acetonitrile (6 ml) to give a colorless solution. 1-chloro-4-isocyanatobenzene (150 mg, 980 µmol) was added. The resultant reaction mixture was warmed at 85° C. for 2 h. Complete by LCMS. The reaction mixture was concentrated in vacuo. The crude material was purified by flash chromatography (silica gel, 40 g, 5% then 5% to 10% EtOAc in hexanes eluent). Fractions from the product peak were combined and concentrated. (Total yield was 322 mg). This product was taken up in 30 mL of ether. To that was added 1.5 mL of 1 M HCl in ether. The resultant salt oiled out. Hexane was added to give a 1:3 ratio of hexanes/ ether. The solid that resulted was scraped down and suspended in the solvent, filtered and washed with 1:1 ether/hexanes to afford a white solid, which was dried under high vacuum to afford (4-chlorophenyl)carbamic acid (S)-2,2,2-trifluoro-1-((R)-2-thiophen-2-ylmethyl-morpholin-4-ylmethyl)-ethyl ester hydrochloride (289 mg) as a white powder. $(M+H)^+=449$ m/e.

Example 50

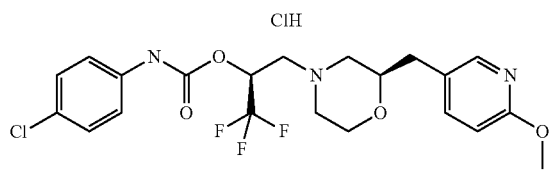 [SMILES: Cl ; COc1ccc(C[C@@H]2CN(C[C@H](OC(=O)Nc3ccc(Cl)cc3)C(F)(F)F)CCO2)cn1]

(4-Chloro-phenyl)-carbamic acid (S)-2,2,2-trifluoro-1-[(R)-2-(6-methoxy-pyridin-3-ylmethyl)-morpholin-4-ylmethyl]ethyl ester Step a 5-Bromo-2-methoxypyridine (247 mg, 1.31 mmol) was dissolved in toluene (6 mL) and cooled to −75° C. t-Butyl lithium (0.77 mL of 1.7 M in pentane, 1.3 mmol) was added dropwise. Stirring was continued at the same temperature for 15 min and then in an ice bath for 5 min. The reaction was cooled to −75° C. and a solution of (S)-2-(methoxy-methyl-carbamoyl)-morpholine-4-carboxylic acid tert-butyl ester (300 mg, 1.09 mmol) in toluene (3 mL) was added dropwise over 5 min. The reaction was stirred at 0° C. for 1.25 h and then poured onto water. The mixture was extracted 3 times with ethyl acetate. The combined organic phase was washed with brine, dried over MgSO$_4$ and concentrated. The crude product was purified by flash chromatography (1:1 EtOAc/heptane eluent) to afford (S)-2-(6-methoxy-pyridine-3-carbonyl)-morpholine-4-carboxylic acid tert-butyl ester (315 mg, 89%) as a colorless oil. $^1$H NMR (400 MHz, CHLOROFORM-d) δ ppm 1.49 (s, 9H) 2.97-3.25 (m, 2H) 3.63-3.76 (m, 1H) 3.85-3.97 (m, 1H) 4.02 (s and overlapping m, 4H) 4.10-4.32 (m, 1H) 4.50-4.66 (m, 1H) 6.80 (dd, J=8.87, 0.54 Hz, 1H) 8.17 (dd, J=8.87, 2.42 Hz, 1H) 8.91 (d, J=2.42 Hz, 1H).

Step b (S)-2-(6-Methoxy-pyridine-3-carbonyl)-morpholine-4-carboxylic acid tert-butyl ester (305 mg, 0.95 mmol) was dissolved in methanol (5 mL) and cooled to 0° C. Sodium borohydride (36 mg, 0.95 mmol) was added and the resulting reaction mixture was stirred for 2 h at room temperature before pouring onto NaHCO$_3$ and extracting 3 times with ethyl acetate. The combined organic phase was washed with brine, dried over MgSO$_4$, filtered and concentrated to afford (S)-2-[hydroxy-(6-methoxy-pyridin-3-yl)-methyl]-morpholine-4-carboxylic acid tert-butyl ester (295 mg, 96%) as a colorless solid.

Mixture of diastereomers by NMR: $^1$H NMR (400 MHz, CHLOROFORM-d) δ ppm 1.35-1.48 (2 s, 9H) 2.61-3.05 (m, 3H) 3.38-3.68 (m, 3H) 3.76-4.04 (m, 6H) 4.51 (dd, J=7.25, 2.69 Hz, 0.6H) 4.70-4.81 (m, 0.4H) 6.74 (dd, J=8.46, 2.55 Hz, 1H) 7.61 (dt, J=8.40, 2.79 Hz, 1H) 8.06-8.17 (m, 1H)

Step c (S)-2-[Hydroxy-(6-methoxy-pyridin-3-yl)-methyl]-morpholine-4-carboxylic acid tert-butyl ester (290 mg, 0.90 mmol) was dissolved in dichloromethane (5 mL) and cooled to 0° C. Tetrabromomethane (593 mg, 1.79 mmol) was added. Triphenylphosphine (305 mg, 1.16 mmol) was then added portionwise and the resulting reaction mixture was stirred at 0° C. for 10 min., then at room temperature for 1.25 h. Reaction was not complete so additional triphenylphosphine (45 mg) was added and the reaction was stirred at room temperature for 2.5 h. The reaction mixture was concentrated and purified by flash chromatography (1:2 EtOAc/heptane eluent) to afford (S)-2-[bromo-(6-methoxy-pyridin-3-yl)-methyl]-morpholine-4-carboxylic acid tert-butyl ester (295 mg, 85%) as a colorless liquid. The product was a mixture of diastereomers by NMR: $^1$H NMR (400 MHz, CHLOROFORM-d) δ ppm 1.42 (s, 3.5H) 1.48 (s, 5.5H) 2.54-3.06 (m, 2H) 3.47 (d, J=2.69 Hz, 0.65H) 3.54-3.64 (m, 0.45H) 3.66-3.88 (m, 3H) 3.93 (s, 3H) 3.97-4.06 (m, 0.45H) 4.23-4.48 (m, 0.55H) 4.83 (d, J=7.25 Hz, 1H) 6.70-6.78 (m, 1H) 7.69 (dd, J=8.60, 2.69 Hz, 1H) 8.13 (d, J=2.42 Hz, 1H).

Step d (S)-2-[bromo-(6-methoxy-pyridin-3-yl)-methyl]-morpholine-4-carboxylic acid tert-butyl ester (290 mg, 0.75 mmol) was dissolved in methanol (5 mL) and hydrogenated at 0.25 bar in the presence of 50 mg 10% Pd/C. Reaction mixture was diluted with ethyl acetate and filtered through Dicalite. The filtrate was washed with 1M sodium hydroxide. The aqueous phase was extract 2 times with ethyl acetate. The combined organic phase was washed with brine, dried over MgSO$_4$, filtered and concentrated to afford (R)-2-(6-Methoxy-pyridin-3-ylmethyl)-morpholine-4-carboxylic acid tert-butyl ester (205 mg, 88%) as a light yellow oil. Chiral HPLC (Chiralpak-AD) indicated that product was 98.3% pure. $^1$H NMR (400 MHz, CHLOROFORM-d) δ ppm 1.45 (s, 9H) 2.53-2.79 (m, 3H) 2.86-3.00 (m, 1H) 3.38-3.58 (m, 2H) 3.73-3.89 (m, 3H) 3.91 (s, 3H) 6.68 (d, J=8.33 Hz, 1H) 7.39-7.49 (m, 1H) 8.00 (d, J=2.15 Hz, 1H).

(R)-2-(6-Methoxy-pyridin-3-ylmethyl)-morpholine-4-carboxylic acid tert-butyl ester (194 mg, 0.63 mmol) was dissolved in dichloromethane (2 mL), cooled to 0° C. and treated with TFA (1 mL). The reaction was stirred at room temperature for 2 h. The reaction mixture was concentrated. The residue was taken up in dichloromethane and extracted with 1M NaOH. The mixture was extracted 3 times with dichloromethane. The combined organic phase was washed with brine, dried over MgSO$_4$ and concentrated to afford (R)-2-(6-methoxy-pyridin-3-ylmethyl)-morpholine (130 mg, 99%) as a light yellow oil. $^1$H NMR (400 MHz, CHLOROFORM-d) δ ppm 2.52-2.63 (m, 2H) 2.65-2.75 (m, 1H) 2.75-2.81 (m, 1H) 2.81-2.91 (m, 2H) 3.49-3.63 (m, 2H) 3.85 (ddd, J=11.28, 3.22, 1.34 Hz, 1H) 3.91 (s, 3H) 6.68 (d, J=8.33 Hz, 1H) 7.44 (dd, J=8.60, 2.42 Hz, 1H) 7.99 (d, J=2.15 Hz, 1H).

Step e

In a 25 mL round-bottom flask was placed (R)-2-(6-methoxy-pyridin-3-ylmethyl)-morpholine (100 mg, 480 µmol), followed by (S)-2-(trifluoromethyl)oxirane (59.2 mg, 528 µmol) and 0.3 mL of dichloromethane. The resultant mixture was stirred at room temperature for 3 days. LCMS showed mostly desired product. $(M+H)^+=321$ m/e. Reaction mixture was concentrated under a stream of nitrogen and used as is in the next step.

Step f

In 4 dram vial, (S)-1,1,1-trifluoro-3-R)-2-((6-methoxypyridin-3-yl)methyl)morpholino)propan-2-ol (154 mg, 480 μmol) was combined with acetonitrile (3 ml) to give a colorless solution. 1-chloro-4-isocyanatobenzene (73.7 mg, 480 μmol) was added. The reaction mixture was warmed at 85° C. for 3 h. Complete by LCMS. The reaction mixture was concentrated in vacuo. The crude material was purified by flash chromatography (silica gel, 24 g, 10% to 25% EtOAc in hexanes gradient). The resulting product was foamed with ether and dried on the pump to afford (4-chloro-phenyl)-carbamic acid (S)-2,2,2-trifluoro-1-[(R)-2-(6-methoxy-pyridin-3-ylmethyl)-morpholin-4-ylmethyl]ethyl ester (85 mg) as a white foam. $(M+H)^+=474$ m/e.

Example 51

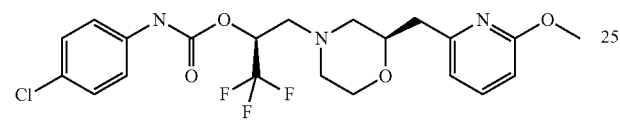

(4-Chlorophenyl)-carbamic acid (S)-2,2,2-trifluoro-1-[(R)-2-(6-methoxy-pyridin-2-ylmethyl)-morpholin-4-ylmethyl]ethyl ester Prepared by a similar procedure to Example 50 except substituting 2-bromo-6-methoxypyridine for 5-bromo-2-methoxypyridine afforded 61 mg of the title compound as a white foam. $(M+H)^+=474$ m/e.

Example 52

IC$_{50}$ Determination of Exemplified Compounds

Dose Response Assay: ChanTest hTRPA1-CHO Stably Transfected Cell Line
  Cell Culture and Assay Reagents:
  Ham's F12 (GIBCO #11765-047)
  Tetracycline-free Fetal Bovine Serum (ClonTech #631106, Lot A301097018)
  Blasticidin (10 mg/ml stock) (GIBCO #A11139-02)
  Zeocin (100 mg/ml stock) (GIBCO #R250-01)
  Doxycycline (SIGMA #D9891)
  Penicillin-Spreptomycin solution (100×) (GIBCO #15140-122)
  GlutaMAX (100×) (GIBCO #35050)
  Trypsin-EDTA (GIBCO #25200-056)
  PBS (without Calcium and Magnesium) (GIBCO #14190)
  HBSS (GIBCO #14025)
  Hepes (GIBCO #15630)
  BSA (fatty acid free, low endotoxin) (SIGMA #A8806-5G)
  DMSO (SIGMA #D2650)
  AP-18 (SIGMA #A7232)
  Cinnamaldehyde (SIGMA #W228613)
  ATP (SIGMA #A-6419)
  2-Aminoethyl diphenylborinate (SIGMA #D9754)
  Menthol (Sigma #M2772)
  FLIPR Calcium 3 Assay Kit (Molecular Devices #R8108)
  Probenecid (INVITROGEN #36400)
  Plates (BD #35-3962)
CHO-K1 Tet-On_HOMSA_TRPA1_Clone_20
  Chinese Hamster Ovary Cells, Inducible Expression Clone #20, received at passage #26
Channel expression in this cell line has been shown to be stable for at least 80 passages
Verified Mycoplasma free with MycoAlert Kit
Cell line expanded and banked
Growth Conditions:
  Growth Media for CHO-K1 Tet-On_HOMSA_TRPA1_Clone_20
  Ham's F-12 with 10% tetracycline-free FBS
  1× penicillin-streptomycin
  1× glutamax
  0.01 mg/ml Blasticidin
  0.40 mg/ml Zeocin
The cell line doubling rate was ~15 h. The culture plates did not exceed 80% confluency.
To induce expression, tetracycline was added to blasticidin/zeocin-free media at a final concentration of 1 ug/ml. Experiments were run at 24 h post induction.
Plating Conditions CHOK1/TRPA1 Cells:
  Harvested cells with 0.025% trypsin/EDTA.
  Resuspended cells in growth media without selection antibiotics.
  Measured cell density and diluted to $2.4 \times 10^5$ cells/ml in media containing 1 ug/ml Doxycycline Plate 25 ul/well into 384 well black/clear tissue culture-treated plates.
  Incubated overnight at 37° C.
Calcium Flux Assay:
Day of Assay:
Reagents:
  Replacement Buffer: Hank's Balanced Salt Solution, 20 mM HEPES along with 0.005% BSA and 2× Probenecid
  Dye Loading Buffer: Cal-3 NW Calcium dye was prepared by dissolving the contents of one vial with 500 ml Hank's Balanced Salt Solution containing 20 mM HEPES.
  Control compounds for CHOK1/TRPA1 cells:
  AP-18, stock 10 mM, prepare 3.5× compound dilution in a Compound Buffer (HBSS/20 mM HEPES/0.005% BSA)—final concentration 10 uM.
  Preparation of Cinnamaldehyde (Agonist Addition): FW=132.16
  Specific gravity=1.046 gm/cc
  1.32 gm/1.046 gm/cc=1.26 ml of stock
  Add 1.74 ml DMSO=3.3 M stock
  Working solution 4.5× (final 100 uM in Compound Buffer: HBSS/20 mM HEPES/0.005% BSA)
  Compounds dilutions were prepared from 5 or 10 mM stock (100% DMSO):
  Adjustments of volumes and concentrations were made at time of titration to reflect desired final assay concentrations.
  Compounds were tested at either 20 μM three folds dilution 11 steps out or 30 μM two folds dilution 11 steps out.
  3 μl of diluted compound were transferred into Weidmann 384-well plate in duplicates side-by-side.
  Compound plates were resuspended with 100 ul of HBSS/20 mM HEPES/0.005% BSA buffer (Compound Buffer):
    column 1A-H: buffer/DMSO (bk)
    column 2A-H: AP-18 (control antagonist for CHOK1 TRPA1 cells)
    column 1I-P: ATP (control for CHOK1 teton cells)

column 2I-P: 2APB (control antagonist for CHOK1/TRPM8 cells).

Growth media was removed from the cell plates (20 ul) and 20 µl of the Replacement Buffer was added followed by addition of 25 µl of diluted dye. All three steps were performed using a Plate Washer BioTek 407. The plates were then incubated for 30' at RT.

After incubation, both the cell and compound plates were brought to the FLIPR and 20 µl of the diluted compounds/antagonist/bk were transferred to the cell plates by the FLIPR. Plates were then incubated for 30' at room temperature. After 30' incubation, plates were returned to the FLIPR and 20 µl of 4.5× Cinnamaldehyde was added to the cell plates. During the compound addition as well as agonist addition, fluorescence readings were taken simultaneously from all 384 wells of the cell plate every 1.5 seconds. Five readings were taken to establish a stable baseline, then 20 µl of sample was rapidly (30 ul/sec) and simultaneously added to each well of the cell plate. The fluorescence was continuously monitored before, during and after sample/agonist addition for a total elapsed time of 100 seconds (compound addition) and 120 seconds (agonist addition). Responses (increase in peak fluorescence) in each well following agonist addition was determined. The initial fluorescence reading from each well, prior to ligand stimulation, was used a zero baseline value for the data from that well. The responses were expressed as % inhibition of the inhibitor control as shown in Table 1 below:

TABLE 1

| Example No. | hTRPA1: IC50 uM |
| --- | --- |
| 1 | 0.0049125 |
| 2 | 0.008495 |
| 3 | 0.0143 |
| 4 | 0.0424 |
| 5 | 0.0307 |
| 6 | 0.0505 |
| 7 | 0.047 |
| 8 | 0.5967 |
| 9 | 0.121 |
| 10 | 3.577 |
| 11 | 0.00558 |
| 12 | 0.108 |
| 13 | 0.00635 |
| 14 | 0.03613 |
| 15 | 0.8035 |
| 16 | 0.1515 |
| 17 | 0.3905 |
| 18 | 0.04255 |
| 19 | 0.1905 |
| 20 | 0.0743 |
| 21 | 1.103 |
| 22 | 0.0643 |
| 23 | 0.781 |
| 24 | 0.0711 |
| 25 | 0.1027 |
| 26 | 0.8465 |
| 27 | 2.6175 |
| 28 | 4.534 |
| 29 | 0.007645 |
| 30 | 0.198 |
| 31 | 0.03455 |
| 32 | 0.451 |
| 33 | 1.632 |
| 34 | 0.03763 |
| 35 | 0.196 |
| 36 | 0.09225 |
| 37 | 0.4575 |
| 38 | 0.07797 |
| 39 | 0.073775 |
| 40 | 3.062 |
| 41 | 2.144 |
| 42 | 0.08345 |

TABLE 1-continued

| Example No. | hTRPA1: IC50 uM |
| --- | --- |
| 43 | 0.01785 |
| 44 | 0.010295 |
| 45 | 0.008085 |
| 46 | 0.0169 |
| 47 | 0.1295 |
| 48 | 3.5565 |
| 49 | 0.11505 |
| 50 | 0.2445 |
| 51 | 0.3985 |

It is to be understood that the invention is not limited to the particular embodiments of the invention described above, as variations of the particular embodiments may be made and still fall within the scope of the appended claims.

The invention claimed is:

1. A compound of formula (I):

$$\text{(I)}$$

wherein:
Y is —O—, —NH—, —SO$_2$—, —N(CH$_3$)— or —N(C(O)CH$_3$)—;
R1 is hydrogen;
R2 is hydrogen or —X-A;
X is —CH$_2$— or a single bond;
A is
   unsubstituted phenyl,
   phenyl mono- or bi-substituted independently with halogen, CF$_3$, alkoxy or lower alkyl,
   unsubstituted heteroaryl, or
   heteroaryl mono-substituted with CF$_3$, lower alkyl or alkoxy; and
R3 is
   unsubstituted phenyl,
   phenyl mono- or bi-substituted independently with halogen or lower alkyl,
   unsubstituted pyridinyl, or
   pyridinyl mono-substituted with halogen,
or a pharmaceutically acceptable salt thereof.

2. The compound according to claim 1, wherein Y is —O—.

3. The compound according to claim 1, wherein Y is —N(CH$_3$)— or —N(C(O)CH$_3$)—.

4. The compound according to claim 1, wherein Y is —SO$_2$—.

5. The compound according to claim 1, wherein Y is —NH—.

6. The compound according to claim 1, wherein R1 is hydrogen.

7. The compound according to claim 1, wherein R2 is hydrogen.

8. The compound according to claim 1, wherein R2 is —X-A.

9. The compound according to claim 1, wherein X is a single bond.

10. The compound according to claim 1, wherein A is unsubstituted phenyl or phenyl mono- or bi-substituted independently with halogen, CF$_3$, alkoxy or lower alkyl.

11. The compound according to claim 1, wherein A is unsubstituted heteroaryl or heteroaryl mono-substituted with CF$_3$, lower alkyl or alkoxy.

12. The compound according to claim 1, wherein said heteroaryl is unsubstituted pyridinyl, unsubstituted pyrimidinyl or unsubstituted thiophene.

13. The compound according to claim 1, wherein said heteroaryl is mono-substituted pyridinyl, mono-substituted pyrimidinyl or mono-substituted thiophene, wherein said mono-substituent is CF$_3$, lower alkyl or alkoxy.

14. The compound according to claim 1, wherein R3 is unsubstituted phenyl or phenyl mono- or bi-substituted independently with halogen or lower alkyl.

15. The compound according to claim 1, wherein R3 is unsubstituted pyridinyl or pyridinyl mono-substituted with halogen.

16. The compound according to claim 1, wherein said compound is:

(4-Chlorophenyl)-carbamic acid (S)-2,2,2-trifluoro-1-[(R)-2-(4-fluoro-3-trifluoromethylphenyl)-morpholin-4-ylmethyl]-ethyl ester hydrochloride;

(4-Chlorophenyl)-carbamic acid (S)-2,2,2-trifluoro-1-[2-(4-fluoro-3-trifluoromethylphenyl)-morpholin-4-ylmethyl]-ethyl ester hydrochloride;

(4-Chloro-3-fluorophenyl)-carbamic acid (S)-2,2,2-trifluoro-1-[(R)-2-(4-fluoro-3-trifluoromethylphenyl)-morpholin-4-ylmethyl]-ethyl ester hydrochloride;

(4-Chloro-3-fluorophenyl)-carbamic acid (S)-1-[(R)-2-(4-chloro-3-fluorophenyl)-morpholin-4-ylmethyl]-2,2,2-trifluoroethyl ester hydrochloride;

(4-Chloro-3-fluorophenyl)-carbamic acid (S)-1-[(R)-2-(3-chloro-4-fluorophenyl)-morpholin-4-ylmethyl]-2,2,2-trifluoroethyl ester hydrochloride;

(4-Chloro-3-fluorophenyl)-carbamic acid (S)-1-[(R)-2-(3-chlorophenyl)-morpholin-4-ylmethyl]-2,2,2-trifluoroethyl ester hydrochloride;

(4-Chloro-3-fluorophenyl)-carbamic acid (S)-1-[(S)-2-(3-chlorophenyl)-morpholin-4-ylmethyl]-2,2,2-trifluoroethyl ester hydrochloride;

(4-Chlorophenyl)-carbamic acid (S)-1-((R)-2-benzyl-morpholin-4-ylmethyl)-2,2,2-trifluoroethyl ester hydrochloride;

(4-Chlorophenyl)-carbamic acid (S)-1-((S)-2-benzyl-morpholin-4-ylmethyl)-2,2,2-trifluoroethyl ester hydrochloride;

(4-Chlorophenyl)-carbamic acid (S)-2,2,2-trifluoro-1-[(R)-2-(3-trifluoromethylphenyl)-morpholin-4-ylmethyl]-ethyl ester hydrochloride;

(4-Chlorophenyl)-carbamic acid (S)-2,2,2-trifluoro-1-[(S)-2-(3-trifluoromethylphenyl)-morpholin-4-ylmethyl]-ethyl ester hydrochloride;

(4-Chloro-3-fluorophenyl)-carbamic acid (S)-2,2,2-trifluoro-1-[(R)-2-(3-trifluoromethylphenyl)-morpholin-4-ylmethyl]-ethyl ester hydrochloride;

(4-Chlorophenyl)-carbamic acid (S)-2,2,2-trifluoro-1-[(R)-2-(3-methoxyphenyl)-morpholin-4-ylmethyl]-ethyl ester;

(4-Chlorophenyl)-carbamic acid (S)-2,2,2-trifluoro-1-[(S)-2-(3-methoxyphenyl)-morpholin-4-ylmethyl]-ethyl ester;

(4-Chlorophenyl)-carbamic acid (S)-2,2,2-trifluoro-1-[(R)-2-(3-methoxyphenyl)-1,1-dioxo-1$\lambda^6$-thiomorpholin-4-ylmethyl]-ethyl ester;

(4-Chlorophenyl)-carbamic acid (S)-2,2,2-trifluoro-1-[2-(3-methoxyphenyl)-1,1-dioxo-1$\lambda^6$-thiomorpholin-4-ylmethyl]-ethyl ester;

(4-Chlorophenyl)-carbamic acid (S)-1-[(R)-1,1-dioxo-2-(3-trifluoromethylphenyl)-1$\lambda^6$-thiomorpholin-4-ylmethyl]-2,2,2-trifluoroethyl ester;

(4-Chlorophenyl)-carbamic acid (S)-1-[(S)-1,1-dioxo-2-(3-trifluoromethylphenyl)-1$\lambda^6$-thiomorpholin-4-ylmethyl]-2,2,2-trifluoroethyl ester;

(4-Chloro-3-fluorophenyl)-carbamic acid (S)-1-[(R)-1,1-dioxo-2-(3-trifluoromethylphenyl)-1$\lambda^6$-thiomorpholin-4-ylmethyl]-2,2,2-trifluoroethyl ester;

(4-Chloro-3-fluorophenyl)-carbamic acid (S)-1-[(S)-1,1-dioxo-2-(3-trifluoromethylphenyl)-1$\lambda^6$-thiomorpholin-4-ylmethyl]-2,2,2-trifluoroethyl ester;

(4-Chloro-3-fluorophenyl)-carbamic acid (S)-2,2,2-trifluoro-1-[(R)-2-(6-trifluoromethylpyridin-3-yl)-morpholin-4-ylmethyl]-ethyl ester;

(4-Chloro-3-fluorophenyl)-carbamic acid (S)-2,2,2-trifluoro-1-[(S)-2-(6-trifluoromethylpyridin-3-yl)-morpholin-4-ylmethyl]-ethyl ester hydrochloride;

(4-Chloro-3-fluorophenyl)-carbamic acid (S)-2,2,2-trifluoro-1-[(S)-2-(2-trifluoromethylpyrimidin-4-yl)-morpholin-4-ylmethyl]-ethyl ester hydrochloride;

(4-Chloro-3-fluoro-phenyl)-carbamic acid (S)-2,2,2-trifluoro-1-[(S)-2-(2-isopropylpyrimidin-4-yl)-morpholin-4-ylmethyl]-ethyl ester hydrochloride;

(4-Chloro-3-fluorophenyl)-carbamic acid (S)-2,2,2-trifluoro-1-[(R)-2-(2-isopropylpyrimidin-4-yl)-morpholin-4-ylmethyl]-ethyl ester hydrochloride;

(4-Chlorophenyl)-carbamic acid (S)-2,2,2-trifluoro-1-(4-methyl-3-phenylpiperazin-1-ylmethyl)-ethyl ester hydrochloride;

(4-Chlorophenyl)-carbamic acid (S)-1-(4-acetyl-3-phenylpiperazin-1-ylmethyl)-2,2,2-trifluoroethyl ester hydrochloride;

(4-Chlorophenyl)-carbamic acid (S)-2,2,2-trifluoro-1-[(R)-2-(4-trifluoromethylphenyl)-morpholin-4-ylmethyl]-ethyl ester hydrochloride;

(4-Chlorophenyl)-carbamic acid (S)-2,2,2-trifluoro-1-[(S)-2-(4-trifluoromethylphenyl)-morpholin-4-ylmethyl]-ethyl ester hydrochloride;

(4-Chloro-3-fluorophenyl)carbamic acid (S)-2,2,2-trifluoro-1-[(R)-2-(4-trifluoromethylphenyl)-morpholin-4-ylmethyl]-ethyl ester hydrochloride;

(4-Chloro-3-fluorophenyl)-carbamic acid (S)-2,2,2-trifluoro-1-[(S)-2-(4-trifluoromethylphenyl)-morpholin-4-ylmethyl]-ethyl ester hydrochloride;

(3-Chloro-4-methylphenyl)-carbamic acid (S)-2,2,2-trifluoro-1-[2-(4-trifluoromethylphenyl)-morpholin-4-ylmethyl]-ethyl ester hydrochloride;

(4-Chloro-3-fluorophenyl)-carbamic acid (S)-1-[(R)-2-(3,4-difluorophenyl)-morpholin-4-ylmethyl]-2,2,2-trifluoroethyl ester hydrochloride;

(4-Chloro-3-fluorophenyl)-carbamic acid (S)-1-[(S)-2-(3,4-difluorophenyl)-morpholin-4-ylmethyl]-2,2,2-trifluoroethyl ester hydrochloride;

(4-Chloro-3-fluorophenyl)carbamic acid (S)-1-[(R)-2-(4-fluorophenyl)-morpholin-4-ylmethyl]-2,2,2-trifluoroethyl ester hydrochloride;

p-Tolylcarbamic acid (S)-1-[2-(3,4-difluorophenyl)-morpholin-4-ylmethyl]-2,2,2-trifluoroethyl ester hydrochloride;

(6-Chloropyridin-3-yl)carbamic acid (S)-2,2,2-trifluoro-1-[2-3-trifluoromethylphenyl]-morpholin-4-ylmethyl]-ethyl ester hydrochloride;

(S)—N-(4-chloro-3-fluorophenyl)-4,4,4-trifluoro-3-[(R)-2-(3-trifluoromethylphenyl)-morpholin-4-ylmethyl]-butyramide;

(S)—N-(4-chloro-3-fluorophenyl)-4,4,4-trifluoro-3-[(S)-2-(3-trifluoromethylphenyl)-morpholin-4-ylmethyl]-butyramide;

(4-Chlorophenyl)-carbamic acid 2,2,2-trifluoro-1-morpholin-4-ylmethyl-ethyl ester;

(4-Chlorophenyl)carbamic acid (S)-2,2,2-trifluoro-1-[2-(4-fluorophenyl)-morpholin-4-ylmethyl]-ethyl ester hydrochloride;

(4-Chlorophenyl)-carbamic acid (S)-2,2,2-trifluoro-1-[2-(3-chlorophenyl)-morpholin-4-ylmethyl]-ethyl ester hydrochloride;

(4-Chlorophenyl)-carbamic acid (S)-2,2,2-trifluoro-1-[2-(3,5-dichlorophenyl)-morpholin-4-ylmethyl]-ethyl ester hydrochloride;

(4-Chlorophenyl)carbamic acid (S)-1-[(R)-2-(3,5-dichlorophenyl)-morpholin-4-ylmethyl]-2,2,2-trifluoroethyl ester hydrochloride;

(4-Chloro-3-fluorophenyl)carbamic acid (S)-1-[(R)-2-(3,5-dichlorophenyl)-morpholin-4-ylmethyl]-2,2,2-trifluoroethyl ester hydrochloride;

(4-Chlorophenyl)-carbamic acid (S)-2,2,2-trifluoro-1-[2-(3-fluorophenyl)-morpholin-4-ylmethyl]-ethyl ester hydrochloride;

(4-Chlorophenyl)-carbamic acid (S)-1-(1,1-dioxo-1$\lambda^6$-thiomorpholin-4-ylmethyl)-2,2,2-trifluoroethyl ester hydrochloride;

(4-Chlorophenyl)-carbamic acid (S)-2,2,2-trifluoro-1-((R)-2-thiophen-2-ylmethyl-morpholin-4-ylmethyl)-ethyl ester hydrochloride;

(4-Chlorophenyl)-carbamic acid (S)-2,2,2-trifluoro-1-[(R)-2-(6-methoxypyridin-3-ylmethyl)-morpholin-4-ylmethyl]ethyl ester; or (4-Chlorophenyl)-carbamic acid (S)-2,2,2-trifluoro-1-[(R)-2-(6-methoxypyridin-2-ylmethyl)-morpholin-4-ylmethyl]ethyl ester.

17. A pharmaceutical composition, comprising a therapeutically effective amount of a compound according to claim 1 and a pharmaceutically acceptable carrier.

\* \* \* \* \*